(12) United States Patent
Hegde

(10) Patent No.: US 10,221,151 B2
(45) Date of Patent: *Mar. 5, 2019

(54) USE OF SMALL MOLECULE INHIBITORS TARGETING EYA TYROSINE PHOSPHATASE

(71) Applicant: Children's Hospital Medical Center, Cincinnati, OH (US)

(72) Inventor: Rashmi Hegde, Cincinnati, OH (US)

(73) Assignee: CHILDREN'S HOSPITAL MEDICAL CENTER, Cincinnati, OH (US)

(*) Notice: Subject to any disclaimer, the term of this patent is extended or adjusted under 35 U.S.C. 154(b) by 35 days.

This patent is subject to a terminal disclaimer.

(21) Appl. No.: 15/648,349

(22) Filed: Jul. 12, 2017

(65) Prior Publication Data

US 2017/0349562 A1 Dec. 7, 2017

Related U.S. Application Data

(62) Division of application No. 14/761,264, filed as application No. PCT/US2014/011539 on Jan. 14, 2014, now Pat. No. 9,725,430.

(60) Provisional application No. 61/753,345, filed on Jan. 16, 2013.

(51) Int. Cl.
C07D 307/80 (2006.01)

(52) U.S. Cl.
CPC .................. *C07D 307/80* (2013.01)

(58) Field of Classification Search
CPC ........................ C07D 307/80; A61K 31/343
See application file for complete search history.

(56) References Cited

U.S. PATENT DOCUMENTS

| 3,012,042 | A | 12/1961 | Hoi et al. |
| 6,166,069 | A | 12/2000 | Malamas et al. |
| 6,432,983 | B1 | 8/2002 | Cullinan |
| 9,725,430 | B2 | 8/2017 | Hegde |
| 2012/0129847 | A1 | 5/2012 | Peters et al. |
| 2014/0128460 | A1 | 5/2014 | Hegde |

FOREIGN PATENT DOCUMENTS

| FR | 1 260 578 | 4/1961 |
| GB | 836272 | 6/1960 |
| WO | WO 03/073987 A2 | 9/2003 |
| WO | WO 2008/002570 A2 | 1/2008 |
| WO | WO 2008/061308 A1 | 5/2008 |
| WO | WO 2011/111675 A1 | 9/2011 |
| WO | WO 2012/048058 A2 | 4/2012 |

OTHER PUBLICATIONS

Ushiroda et al (2011): STN International HCAPLUS database, (Columbus, Ohio), Accession No. 2011:1169959.*
Oka et al (2012): STN International HCAPLUS database, (Columbus, Ohio), Accession No. 2012:1338926.*
Wempe et al (2011): STN International HCAPLUS database, (Columbus, Ohio), Accession No. 2011:404430.*
Alonso, et al. 2004, "Protein Tyrosine Phosphatases in the Human Genome", Cell, vol. 117, 699-711.
Alpin, A. C., et al., (2008), "The Aortic Ring Model of Angiogenesis", Methods Enzymo., 443, 119-136.
Carlsson, et al., "Synthesis and Preliminary Characterization of a Novel Antiarrhythmic Compound (KB130015) with an Improved Toxicity Profile Compared with Amiodarone," *J. Med. Chem.*, 45(3): 623-630, 2002.
Cecchi, et al., (2004), "Role of oxidative stress as physiopathologic factor in the preterm infant", Minerva Pediatr., 56(4):381-394. Abstract.
Claeys, et al., "Recherches dans la série des benzo (b) thiopènes. 1.—(Dialkylaminoalkyloxy-4 halogéno-3,5 benzoyl)—2 ou 3 benzo (b) thiopènes," *Chimie Therapeutique: The European Journal of Medicinal Chemistry*, 7(5): 377-384, 1972.
Cook, P. J. et al., (2009), "Tyrosine dephosphorylation of H2AX modulates apoptosis and survival decisions", Nature, 458, 591-596.
Farabaugh et al., (2011), "Eya2 is required to mediate the pro-metastatic functions of Six1 via the induction of TGF-b signaling, epithelial—mesenchymal transition, and cancer stem cell properties", Oncogene, 259.
Fingl et al., (1975) in "The Pharmacological Basis of Therapeutics", Ch. 1, pp. 1-46.
Gerhardt, H., et al. (2005), "How do endothelial cells orientate?", EXS, Mechanics of Angiogenesis, 3-15.
Goldstein et al., (2005), "Redox Paradox: Insulin Action Is Facilitated by Insulin-Stimulated Reactive Oxygen Species With Multiple Potential Signaling Targets", Perspectives in Diabetes, vol. 54, pp. 311-321.
Grattagliano et al., (1998), "Oxidative Retinal Products and Ocular Damages in Diabetic Patients", Free Radical Biology & Medicine, 25(3):369-372.
Hu et al., (2006), "A Convergent Synthetic Study of Biologically Active Benzofuran Derivatives," Arch Pharm Res, 29(6):476-478.
Koch et al., (2011), "Signal transduction by vascular endothelial growth factor receptors", Biochem. J., 437:169-183.
Krishnan, N., et al., (2009), "Dephosphorulation of the C-terminal Tyrosyl Residue of the DNA Damage-related Histone H2A.X Is Mediated by the Protein Phosphatase Eyes Absent", J. Biol. Chem., 284:24 (16066-16070).
Lanahan et al., (2010), "VEGF Receptor 2 Endocytic Trafficking Regulates Arterial Morphogenesis", Developmental Cell, 78:713-724.

(Continued)

*Primary Examiner* — Golam M Shameem

(74) *Attorney, Agent, or Firm* — Knobbe, Martens, Olson & Bear, LLP

(57) ABSTRACT

Inhibitors of EYA tyrosine phosphatase are provided herein, as well as pharmaceutical compositions and methods relating thereto.

20 Claims, 12 Drawing Sheets

Specification includes a Sequence Listing.

(56) References Cited

OTHER PUBLICATIONS

Lanahan et al., (2014), "PTP1 b Is a Physiologic Regulator of Vascular Endothelial Growth Factor Signaling in Endothelial Cells", Molecular Cardiology, pp. 902-913. Downloaded from http://circ.ahajournals.org/ at Childrens Hosp on May 3, 2016.

Langheinrich, U., (2003), "Zebrafish: a new model on the pharmaceutical catwalk", BioEssays: News and Reviews in Molecular, Cellular and Developmental Biology 25, 904-912.

Locuson, et al., (2004) "Charge and Substituent Effects on Affinity and Metabolism of Benzbromarone-Based CYP2C19 Inhibitors," *J. Med. Chem.*, 47(27): 6768-6776.

McDonald et al., (2012), "Warfarin-Amiodarone Drug—Drug Interactions: Determination of $[I]_u/K_{I_u}$ for Amiodarone and Its Plasma Metabolites," Clin Pharmacol Ther, 91(4):709-717.

Moreno et al., (2004), "Retinal Oxidative Stress Induced by High Intraocular Pressure", Free Radical Biology & Medicine, 37(6):803-812.

Nakamura et al., (2008), "Role of Portein Tyrosine Phosphatase 1B in Vascular Endothelial Growth Factor Signaling and Cell—Cell Adhesions in Endothelial Cells", Molecular Medicine, pp. 1183-1191.

Nita et al., (2015), "The Role of the Reactive Oxygen Species and Oxidative Stress in the Pathomechanism of the Age-Related Ocular Diseases and Other Pathologies of the Anterior and Posterior Eye Segments in Adults", Oxidative medicine and Cellular Longevity, vol. 2016, Article ID 3164734, 23 pages.

Oshikawa et al., (2010), "Extracellular SOD-Derived $H_2O_2$ Promotes VEGF Signaling in Caveolae/Lipid Rafts and Post-Ischemic Angiogenesis in Mice", PloS ONE, 5(4):1-15.

Pandey, R. N. et al., (2010), "The Eyes Absent phosphatase-transactivator proteins promote proliferations, transformation, migration, and invasion of tumor cells", Oncogene 29:3715-3722.

Pemp et al., (2010), "Effects of Antioxidants (AREDS Medication) on Ocular Blood Flow and Endothelial Function in an Endotoxin-Induced Model of Oxidative Stress in Humans", IOVS, 51(1):2-6.

Rajala et al. (2009), Invest Ophthalmol Vis Sci, 50(3), pp. 1033-1040.

Rao et al., (2000), "Free Radical Mediated Photoreceptor Damage in Uveitis", Progress in Retinal and Eye Research, 19(1):41-68.

Rayapureddi, J. P. et al., (2003), "Eyes absent represents a class of protein tyrosine phosphatases", Nature, 426:295-298.

Rayapureddi, J. P. et al., (2006), "Branchio-oto-renal syndrome associated mutations in Eyes Absent 1 result in loss of phosphatase activity", *FEBS Lett* 580, 3853-3859.

Reed, M. J., et al., (2011), "Angiogenesis In Vitro Utilizing Murine Vascular Explants in Miniaturized 3-Dimensional Collagen Gels", Open Circ Vasc J. 4, 12-17.

Salmeen, et al., (2003), "Redox regulation of protein tyrosine phosphatase 1B involves a sulphenyl-amide intermediate", Nature, 429:769-773.

Spector, Abraham, (1995). "Oxidative stress-induced cataract: mechanism of action", Biochemistry and Molecular Biology Laboratory, vol. 9, pp. 1171-1182.

Staton, C. A., et al., (2009), "A critical analysis of current in vitro and in vivo angiogenesis assays", Int J of Exp Path. 90, 195-221.

STN International HCAPLUS database, (Columbus, Ohio), Accession No. 2011:1169959.

Van Reyk, et al., (2003), "The retina: Oxidative stress and diabetes", Redox Rep., 8(4):187-192. Abstract.

Wang et al., (2016), "PTP1B inhibitor promotes endothelial cell motility by activating the DOCK180/ZRac1 pathway", Nature: Scientific Reports, pp. 1-11.

Wempe, et al., (2011), "Developing Potent Human Uric Acid Transporter 1 (hURAT1) Inhibitors," J. Med. Chem., 2011, 54 (8), pp. 2701-2713.

Wempe, et al., (2011), "Human Uric Acid Transporter 1 (hURAT1): An Inhibitor Structure-Activity Relationship (SAR) Study," *Nucleosides Nucleotides and Nucleic Acids*, 30(12): 1312-1323.

Wiesmann et al., (2004), "Allosteric inhibition of protein tyrosine phosphatase 1 B", Nat Struct Mol Biol., 11(8):730-737.

Wrobel et al., (1999), "PTP1 B Inhibition and Antihyperglycemic Activity in the ob/ob Mouse Model of Novel 11-Arylbenzo[b]naphtha[2,3-d]furans and 11-Arylbenzo[b]naphtha[2,3-d]thiophenes," *J. Med. Chem.*, 42(18): 3199-3202.

Ye, et al., (2010), "Novel thiophene derivatives as PTP1B inhibitors with selectivity and cellular activity," *Bioorg. Med. Chem.*, 18(5): 1773-1781.

Office Action for U.S. Appl. No. 13/787,677 dated Feb. 26, 2015.

Response to Office Action filed May 26, 2015 in U.S. Appl. No. 13/787,677.

Office Action issued in the U.S. Appl. No. 13/787,677 dated Oct. 24, 2016.

Office Action issued in U.S. Appl. No. 14/761,264 dated May 9, 2016.

International Search Report and Written Opinion dated Jul. 11, 2014, issued in International Application No. PCT/US2014/011539, Filed Jan. 14, 2014.

Partial Search Report dated Apr. 2, 2014, issued in International Application No. PCT/US2014011539, filed Jan. 14, 2014.

International Preliminary Report on Patentability dated Jul. 21, 2015, issued in International Application No. PCT/US2014/011539, filed Jan. 14, 2014.

Response to Office Action filed Feb. 23, 2017 in U.S. Appl. No. 13/787,677.

Office Action issued in the U.S. Appl. No. 13/787,677 dated May 31, 2017.

Response to Office Action filed Jul. 14, 2017 in U.S. Appl. No. 13/787,677.

Response to Office Action filed Aug. 5, 2016 in U.S. Appl. No. 14/761,264.

\* cited by examiner

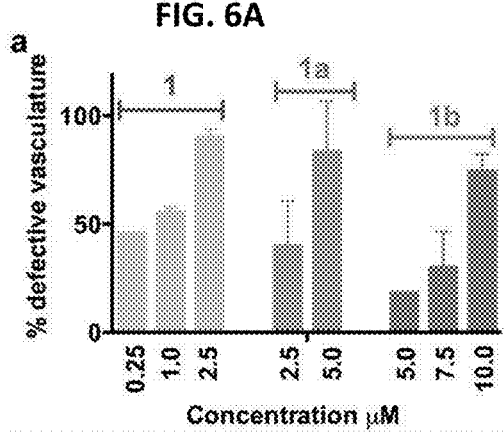
FIG. 6A
FIG. 6B
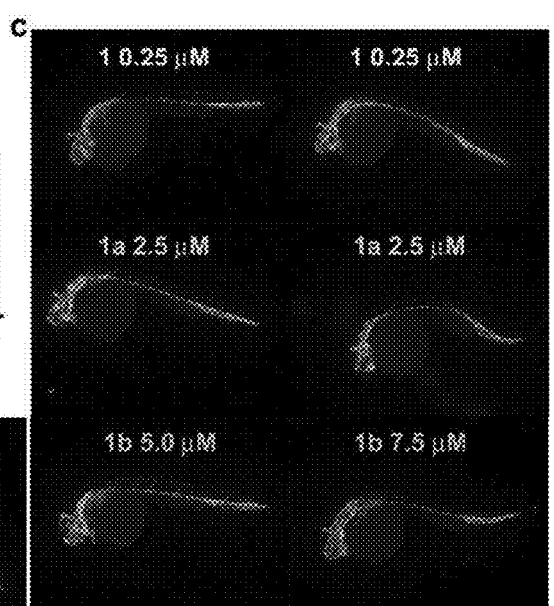
FIG. 6C

FIG. 8A
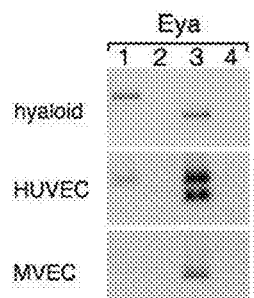
FIG. 8F
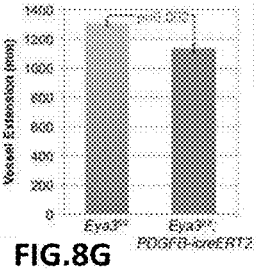
FIG. 8G
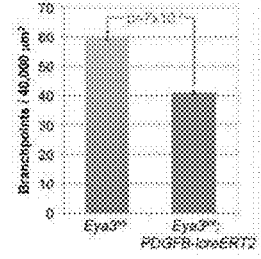
FIG. 8B
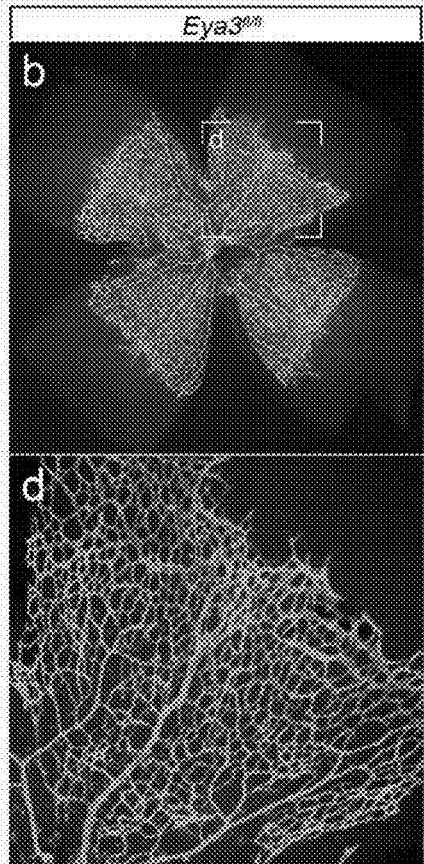
FIG. 8C
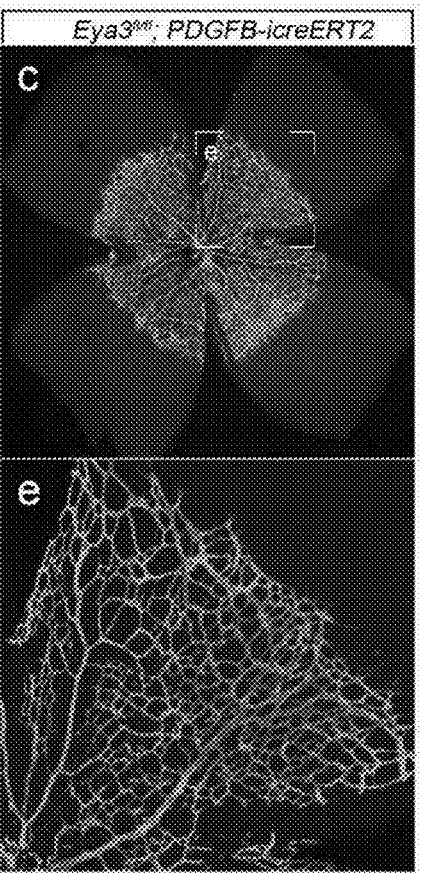
FIG. 8D  FIG. 8E

Figure 10

```
              *    **      **     * *
EYA1 320 dler vflwdl dET iiVfhsl ltgSYasRYg rdpptvslg lrmeemifnl
EYA2 266 eier vfvwdl dET iiIfhsl ltgTFasRYg kdtttsvrig lmmeemifnl
EYA3 301 eler vflwdl dET iiIfhsl ltgSYaqKYg kdptvvigsg ltmeemifev
EYA4 367 dler vfvwdl dET iiVfhsl ltgSYaqKYg kdppmavtlg lrmeemifnl
              Motif I EYA1 370 adthlffndl eecdqvhidd vssddngqdl stynfgtdgf paaatsanlc
EYA2 316 adthlffndl edcdqihvdd vssddngqdl stynfsadgf hssapganlc
EYA3 351 adthlffndl eecdqvhved vasddngqdl snysfstdgf sgsggsgshg
EYA4 417 adthlffndl eecdqvhidd vssddngqdl stysfatdgf haaassanlc EYA1 420 latqvrggvd wmrklafryr rvkeiyntyk nnvggllgpa kreawlqlra
EYA2 366 lgsgvhggvd wmrklafryr rvkemyntyk nnvggligtp kretwlqlra
EYA3 401 ssvgvgggvd wmrklafryr kvreiydkhk snvggllspq rkealqrlra
EYA4 467 lptgvrggvd wmrklafryr rvkelyntyk nnvggllgpa krdawlqlra

**
EYA1 470 elealtdsWl tlalkalsli hsrtncvnil vt tqlipal akvllyglgi
EYA2 416 elealtdlWl thslkalnli nsrpncvnvl vt tqlipal akvllyglgs
EYA3 451 eievltdsWl gtalksllli qsrkncvnvl it tqlvpal akvllyglge
EYA4 517 eiegltdsWl tnalkslsii strsncinvl vt tqlipal akvllyslgg
                                              Motif II
              *
EYA1 520 vfpieniysa tkig escfe riiqrfgrkv vyvvi gdgve eeqgakkham
EYA2 466 vfpieniysa tktg escfe rimqrfgrka vyvvi gdgve eeqgakkhnm
EYA3 501 ifpieniysa tkig escfe rivsrfgkkv tyvvi gdgrd eeiaakqhnm
EYA4 567 afpieniysa tkig escfe rimqrfgrkv vyvvi gdgve eeqgaakkhnm
                       Motif III EYA1 570 pfwrisshsd lmalhhalel eyl
EYA2 516 pfwrischad lealrhalel eyl
EYA3 551 pfwritnhgd lvslhqalel dfl
EYA4 617 pfwrisshsd llalhqalel eyl
```

USE OF SMALL MOLECULE INHIBITORS TARGETING EYA TYROSINE PHOSPHATASE

CROSS REFERENCE TO RELATED APPLICATIONS

Any and all priority claims identified in the Application Data Sheet, or any correction thereto, are hereby incorporated by reference under 37 CFR 1.57. For example, this application is a divisional of U.S. patent application Ser. No. 14/761,264, filed on Jul. 15, 2015, which is a U.S. National Phase of International Application No. PCT/US2014/011539, filed on Jan. 14, 2014 and published on Aug. 7, 2014 as WO 2014/113407, which claims the benefit of U.S. Provisional Application 61/753,345, filed on Jan. 16, 2013, which is incorporated herein by reference in its entirety.

STATEMENT REGARDING FEDERALLY SPONSORED R&D

The invention was made with government support under EY014648 and EY019125 awarded by the National Institutes of Health. The government has certain rights in the invention.

REFERENCE TO SEQUENCE LISTING

The present application is being filed along with a Sequence Listing in electronic format. The Sequence Listing is provided as a file entitled CHMC45-001WO2.txt created on Jan. 13, 2014, which is 10 Kb in size. The information in the electronic format of the Sequence Listing is incorporated herein by reference in its entirety.

BACKGROUND

Field

The subject matter provided herein relates to inhibition of EYA tyrosine phosphatase; in particular compounds, compositions and methods relating to inhibition of EYA tyrosine phosphatase.

Description of the Related Technology

Protein tyrosine phosphatases (PTPs) are a group of enzymes that remove phosphate groups from phosphorylated tyrosine residues on proteins. Protein tyrosine (pTyr) phosphorylation is a post-translational modification that can create recognition motifs for protein interactions and cellular localization, affect protein stability, and regulate enzyme activity. Maintaining an appropriate level of protein tyrosine phosphorylation activity plays a role in many cellular functions. Development of inhibitors of protein tyrosine phosphatases may be a promising new avenue for new therapeutic compounds.

SUMMARY

Provided are compounds, compositions and methods relating to the inhibition of EYA tyrosine phosphatase. In some embodiments, the compounds, compositions and methods provided herein include a compound having the structure of Formula I:

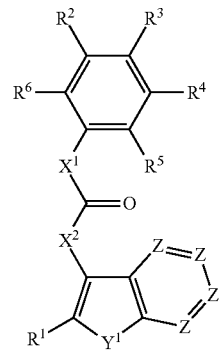

or a pharmaceutically acceptable salt thereof,
wherein:
$R^1$ is selected from the group consisting of $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, (cyclolalkyl)alkyl, and amino, said $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, and (cyclolalkyl)alkyl are each optionally substituted with one or more $R^{1A}$;

each $R^{1A}$ is independently selected from the group consisting of hydroxy, halo, cyano, nitro, $C_{1-6}$ alkyl optionally substituted with up to 5 fluoro, $C_{1-6}$ alkoxy optionally substituted with up to 5 fluoro;

$R^2$ is selected from the group consisting of H (hydrogen), halo, hydroxy, and $C_{1-6}$ alkyl substituted with one or more hydroxy;

$R^3$ is selected from the group consisting of halo, hydroxy, and $C_{1-6}$ alkyl substituted with one or more hydroxy;

$R^4$ is H (hydrogen) or halo;

$R^5$ and $R^6$ are each independently selected from the group consisting of H (hydrogen), halo, cyano, $C_{1-6}$ alkyl, aryl, heteroaryl, heterocyclyl, and amino, said $C_{1-6}$ alkyl, aryl, heteroaryl, and heterocyclyl each optionally substituted with one or more $R^{1A}$;

$X^1$ is $[C(R^{2A})_2]_n$, O (oxygen), or $NR^{2A}$, or $X^1$ is absent;
$X^2$ is $[C(R^{2A})_2]_n$, O (oxygen), or $NR^{2A}$, or $X^2$ is absent;
each $R^{2A}$ is independently selected from the group consisting of H (hydrogen), halo, hydroxy, O-carbamyl, N-carbamyl, C-amido, S-sulfonamido, N-sulfonamido, C-carboxy, amino, aryl, heteroaryl, heterocyclyl, arylalkyl, heteroarylalkyl, heterocyclylalkyl, cycloalkyl, cycloalkenyl, (cyclolalkyl)alkyl, $C_{1-6}$ alkyl substituted with one or more hydroxyl, and $C_{1-6}$ alkyl optionally substituted with up to 5 fluoro;
each n is independently 1 or 2;
$Y^1$ is O (oxygen), S (sulfur), or $NR^{2A}$; and
each Z is independently selected from the group consisting CR^{2A}, and N (nitrogen), with the proviso that the compound is not:

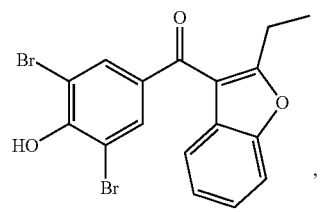

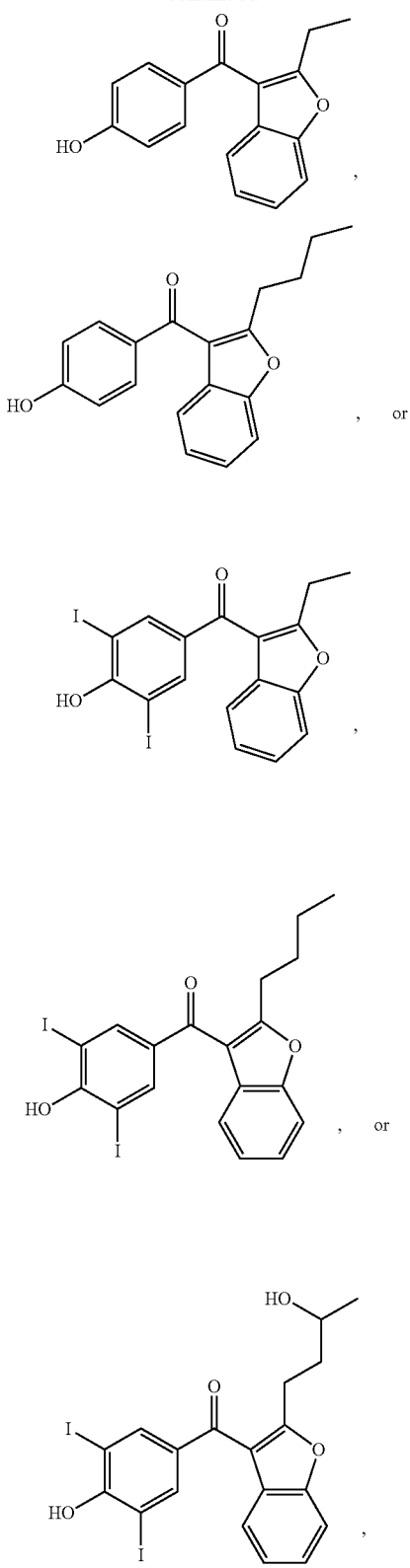

, or or a pharmaceutically acceptable salt thereof.

In some embodiments, the compounds, compositions and methods provided herein include a compound having the structure of Formula IV:

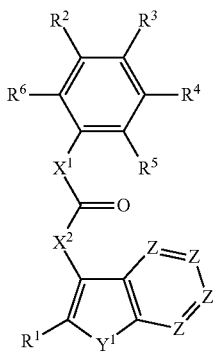

or a pharmaceutically acceptable salt thereof, wherein:

$R^1$ is selected from the group consisting of $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, (cyclolalkyl)alkyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, and amino, said $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, and (cyclolalkyl)alkyl are each optionally substituted with one or more $R^{14}$;

each $R^{14}$ is independently selected from the group consisting of hydroxy, halo, cyano, nitro, $C_{1-6}$ alkyl optionally substituted with up to 5 fluoro, $C_{1-6}$ alkoxy optionally substituted with up to 5 fluoro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, and amino;

$R^2$ is selected from the group consisting of H (hydrogen), halo, hydroxy, O-carbamyl, N-carbamyl, O-thiocarbamyl, N-thiocarbamyl, C-amido, N-amido, S-sulfonamido, N-sulfonamido, C-carboxy, O-carboxy, and $C_{1-6}$ alkyl substituted with one or more hydroxy;

$R^3$ is selected from the group consisting of halo, hydroxy, O-carbamyl, N-carbamyl, C-amido, S-sulfonamido, N-sulfonamido, C-carboxy, amino, and $C_{1-6}$ alkyl substituted with one or more hydroxy;

$R^4$ is selected from the group consisting of H (hydrogen), halo, and $C_{1-6}$ alkyl optionally substituted with up to 5 fluoro and $C_{1-6}$ alkoxy optionally substituted with up to 5 fluoro;

$R^5$ and $R^6$ are each independently selected from the group consisting of H (hydrogen), halo, cyano, $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, (cyclolalkyl)alkyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, and amino, said $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, and (cyclolalkyl)alkyl each optionally substituted with one or more $R^{14}$;

$X^1$ is $[C(R^{24})_2]_n$, O (oxygen), or $NR^{24}$, or $X^1$ is absent;
$X^2$ is $[C(R^{24})_2]_n$, O (oxygen), or $NR^{24}$, or $X^2$ is absent;

each $R^{2A}$ is independently selected from the group consisting of H (hydrogen), halo, hydroxy, O-carbamyl, N-carbamyl, C-amido, S-sulfonamido, N-sulfonamido, C-carboxy, amino, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, (cyclolalkyl)alkyl, $C_{1-6}$ alkyl substituted with one or more hydroxyl, and $C_{1-6}$ alkyl optionally substituted with up to 5 fluoro;

each n is independently 1 or 2;

$Y^1$ is O (oxygen), S (sulfur), or $NR^{2A}$; and each Z is independently selected from the group consisting $CR^{2A}$, and N (nitrogen);

with the proviso that the compound of Formula IV does not include a compound having the Formula IB:

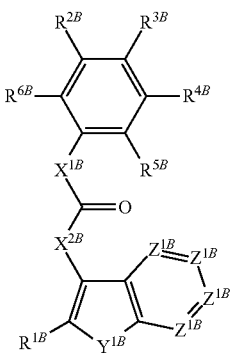

wherein:

(aa) $R^{1B}$ is selected from the group consisting of $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, (cyclolalkyl)alkyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, and amino, said $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, and (cyclolalkyl)alkyl are each optionally substituted with one or more $R^{1C}$;

(bb) each $R^{1C}$ is independently selected from the group consisting of hydroxy, halo, cyano, nitro, $C_{1-6}$ alkyl optionally substituted with up to 5 fluoro, $C_{1-6}$ alkoxy optionally substituted with up to 5 fluoro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, and amino;

(cc) $R^{2B}$ is selected from the group consisting of H (hydrogen), halo, hydroxy, O-carbamyl, N-carbamyl, O-thiocarbamyl, N-thiocarbamyl, C-amido, N-amido, S-sulfonamido, N-sulfonamido, C-carboxy, O-carboxy, and $C_{1-6}$ alkyl substituted with one or more hydroxy;

(dd) $R^{3B}$ is selected from the group consisting of halo, hydroxy, O-carbamyl, N-carbamyl, C-amido, S-sulfonamido, N-sulfonamido, C-carboxy, amino, and $C_{1-6}$ alkyl substituted with one or more hydroxy;

(ee) $R^{4B}$ is selected from the group consisting of H (hydrogen), halo, and $C_{1-6}$ alkyl optionally substituted with up to 5 fluoro and $C_{1-6}$ alkoxy optionally substituted with up to 5 fluoro;

(ff) $R^{5B}$ and $R^{6B}$ are each independently selected from the group consisting of H (hydrogen), halo, cyano, $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, (cyclolalkyl)alkyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, and amino, said $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, and (cyclolalkyl)alkyl each optionally substituted with one or more $R^{1C}$;

(gg) $X^{1B}$ is $[C(R^{2C})_2]r$, O (oxygen), or $NR^{2C}$, or $X^{1B}$ is absent;

(hh) $X^{2B}$ is $[C(R^{2C})_2]r$, O (oxygen), or $NR^{2C}$, or $X^{2B}$ is absent;

(ii) each $R^{2C}$ is independently selected from the group consisting of H (hydrogen), $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, (cyclolalkyl)alkyl, and $C_{1-6}$ alkyl optionally substituted with up to 5 fluoro;

(jj) each r is independently 1 or 2;

(kk) $Y^{1B}$ is O (oxygen), S (sulfur), or $NR^{2C}$; and (ll) each $Z^{1B}$ is independently selected from the group consisting $CR^{2C}$, and N (nitrogen).

Also presented herein is a compound having the structure of Formula I for use in treating proliferative retinopathy, retinopathy of prematurity, diabetic retinopathy, age related macular degeneration, retinal vasculitis, exudative vitreoretinopathy, tumor angiogenesis, hemangiomas or tumor metastasis in an individual. Also presented herein is a compound having the structure of Formula I for use in treating proliferative retinopathy, retinopathy of prematurity, diabetic retinopathy, age related macular degeneration, retinal vasculitis, exudative vitreoretinopathy, tumor angiogenesis, hemangiomas, tumor metastasis, treating breast cancer, ductal carcinoma lobule carcinoma, breast epithelial cancer, ovarian cancer, including epithelial ovarian cancer, desmoid tumor, malignant peripheral nerve sheath cancer, acute leukemia, rhabdomyosarcoma, Ewing's sarcoma, extra-skeletal myxoid chondrosarcoma, or endometrial cancer in an individual.

Also presented herein is a composition comprising a pharmaceutically acceptable excipient, and a compound having the structure of Formulae I, II, III or IV.

Also presented herein is a method for evaluating the inhibition of EYA tyrosine phosphatase comprising contacting a full-length EYA tyrosine phosphatase with a compound from a library of compounds and evaluating the results; wherein the compound has a user selected relative level of inhibitory activity compared to the inhibitory activity of the same compound when it contacts the catalytic domain (ED) of EYA tyrosine phosphatase.

Also presented herein is a method for evaluating the inhibition of EYA tyrosine phosphatase comprising: a) contacting the catalytic domain (ED) of EYA tyrosine phosphatase with a compound from a library of compounds and evaluating the results; and b) contacting a full-length EYA tyrosine phosphatase with the compound and evaluating the results. The method can further comprise: c) performing a) for each compound in the library of compounds; d) selecting one or more compounds from c) that inhibit the catalytic domain (ED) of EYA tyrosine phosphatase according to a user-selected level; e) performing b) for each compound selected in d); and f) selecting one or more compounds from e) that inhibit full-length EYA tyrosine phosphatase according to a user-selected level.

Also presented herein is a method for identifying a compound that specifically inhibits EYA tyrosine phosphatase comprising: a) contacting EYA tyrosine phosphatase with a compound and evaluating the results; and b) contacting a cysteine catalysis-based protein tyrosine phosphatase or an FCP/SCP family protein tyrosine phosphatase with a compound have the structure of Formulae I, II, III or IV and evaluating the results.

Also presented herein is a method of evaluating a compound for inhibition of cell migration, proliferative retinopathy, retinopathy of prematurity, diabetic retinopathy, age related macular degeneration, retinal vasculitis, exudative vitreoretinopathy, tumor angiogenesis, hemangiomas or tumor metastasis, comprising contacting an EYA tyrosine phosphatase with a compound and evaluating the results. In some embodiments, the compound comprises a compound having the structure of Formulae I, II, III or IV.

Also presented herein is a method of evaluating a compound for inhibition of cell migration, proliferative retinopathy, retinopathy of prematurity, diabetic retinopathy, age related macular degeneration, retinal vasculitis, exudative vitreoretinopathy, tumor angiogenesis, hemangiomas or tumor metastasis, comprising contacting an EYA tyrosine phosphatase with a compound and evaluating the results. In some embodiments, the compound comprises a compound having the structure of Formulae I, II, III or IV.

BRIEF DESCRIPTION OF THE DRAWINGS

FIG. 1A shows the structure of EYA inhibitor NSC85433, compound 1.

FIG. 1B Substrate titration shows that compound 1 is not a competitive inhibitor of EYA3. Increasing concentration of substrate does not overcome inhibition. Each point represents the mean and standard deviation of two independent readings.

FIG. 1C Plots of Vmax and Km as a function of inhibitor concentration.

FIG. 1D Compound 1 does not affect the interaction between EYA3 and SIX2. Recombinant purified EYA3 and His-SIX2 were mixed and treated with either the vehicle control (1% DMSO) (lane 1) or 50 µM compound 1 (lane 5) for 15 minutes at room temperature. The mixture was loaded on a Ni-NTA column. Beads were washed with 3 column volumes of load buffer (last washes, lanes 2 and 6). Proteins retained on the beads are shown in lanes 3 and 7. Lanes 4 and 8 are molecular weight markers.

FIG. 2A Trans-well migration of MCF10A cells transfected with either pcDNA 3.2N5-DEST (V5 vector control), V5-EYA2, or the phosphatase dead mutant V5-EYA2 (D250N).

FIG. 2B MCF10A-EYA2 cells were treated with 7.5 µM of compounds 1, 1a, 1b, or 1c. Percentage migration relative to cells treated with the vehicle (0.1% DMSO) is shown.

FIG. 2C Transwell migration of MCF10A-EYA2(D250N) cells in the presence of 7.5 µM of compounds 1, 1a, 1b, or 1c.

FIG. 2D Relative migration of MCF10A-EYA2 cell migration by compounds 1, 1a, and 1b when treated with the doses indicated on the x-axis.

FIG. 2E Change in cell density of MCF10A-V5 ctl, MCF10A-EYA2 and MCF10A-EYA2(D250N) cells after 48 hours measured using the MTT assay.

FIG. 2F Change in cell density of MCF10A-EYA2 cells after 48 hours in the presence of either vehicle control (0.1% DMSO) or 10 µM compounds 1, 1a, and 1b. For transwell migration experiments each bar represents the mean (and standard error) of five random fields per filter and two wells per experiment. For proliferation experiments each bar represents the mean (and standard error) of three experiments. ns is not significant, $*p<0.05$, $P<0.01$, $*P<0.001$. In each case the p value shown is relative to the V5-control or the vehicle-treated sample.

FIG. 3A Expression of Eya transcripts in HUVECs.

FIG. 3B Change in cell density of HUVECs-scramble control and HUVEC-shEYA3 after 24 hours.

FIG. 3C Transwell migration of HUVEC-scramble control and HUVEC-shEYA3 shows a significant reduction in motility when EYA3 levels are reduced.

FIG. 3D Capillary morphogenesis on matrigel was assayed using HUVECscramble control and HUVEC-shEYA3. In each case the bars represent the mean and standard error of three experiments. ns is not significant, $*p<0.05$, $P<0.01$, $*P<0.001$. In each case the p value shown is relative to the scramble-control.

FIGS. 4 A-D show that EYA inhibitors attenuate migration and tubulogenesis of HUVECs.

FIG. 4A Percent migration of HUVECs in the presence of 5 µM of each inhibitor relative to the vehicle control.

FIG. 4B Change in cell density after 24 hours in the presence of either vehicle control (0.1% DMSO) or 5 µM of each EYA inhibitor.

FIG. 4C Quantitation of the number of tube-like structures formed by HUVECs in the presence of either the vehicle control (0.1% DMSO) or the indicated concentrations of compounds 1, 1 a and 1 b. The number of tubes was measured using NeuroJ. Data are mean and standard error of three independent experiments. p-values from a one-way ANOVA are shown; ns is not significant, $*p<0.05$, $P<0.01$, $*P<0.001$.

FIG. 4D Representative images of HUVECs on Matrigel in the presence of the indicated doses of compound 1a.

FIG. 5A Representative images of aortic rings treated with either the vector control (0.1% DMSO) or 5 µM of compounds 1, 1a, or 1b. Rings were stained with isolectin. 1 c is used as a negative control.

FIG. 5B Quantitation of the number of sprouts per ring; ns is not significant, $*p<0.05$, $P<0.01$, $*P<0.001$.

FIG. 5C Compounds 1, 1a, and 1b in the indicated doses were used in aortic ring experiments. The number of sprouts per ring is plotted indicating that inhibition of aortic sprouting was dose-dependent.

FIGS. 6A-C show dose-dependent effects of EYA inhibitors on the developing zebrafish vasculature.

FIG. 6A Titration of compounds 1, 1a, 1b at the indicated doses.

FIG. 6B Images of representative control and vehicle (DMSO) treated embryos at 24 hpf.

FIG. 6C Representative images of EYA inhibitor treated embryos at 24 hpf.

FIGS. 8A-G show the effect of knockout of Eya3 on post-natal retinal angiogenesis.

FIG. 8A shows endpoint PCR assessment of expression of Eya1-4 in hyaloid vessels and MVECs.

FIG. 8B show isolectin labeled retinal blood vessels at postnatal day 5 in control mice.

FIG. 8C show isolectin labeled retinal blood vessels at postnatal day 5 in experimental mice.

FIG. 8D show isolectin labeled retinal blood vessels at postnatal day 5 in control mice (magnified).

FIG. 8E show isolectin labeled retinal blood vessels at postnatal day 5 in experimental mice (magnified).

FIG. 8F show quantitative analysis of angiogenic extension and vessel density.

FIG. 8G show quantitative analysis of angiogenic extension and vessel density.

FIG. 10 is a diagram showing sequence alignment of the ED domains of human EYA 1 (Accession No. Q99502; SEQ. ID 1), EYA2 (Accession No. CAA71310.1; SEQ. ID 2), EYA3 (Accession No. NP_001981.2; SEQ. ID 3), EYA4 (Accession No. CAA76636.1; SEQ. ID 4). The gray shaded box indicates the cap domain. Outlined are motifs I, II and II. Upper case, bold residues line the hydrophobic pocket for the dibromophenol group of compound 1. Asterisks indicate residues that form the phosphotyrosine binding site.

FIG. 11A shows quantitative analysis of inhibition of neovascularization of an EYA inhibitor.

DETAILED DESCRIPTION

Figure 1A:
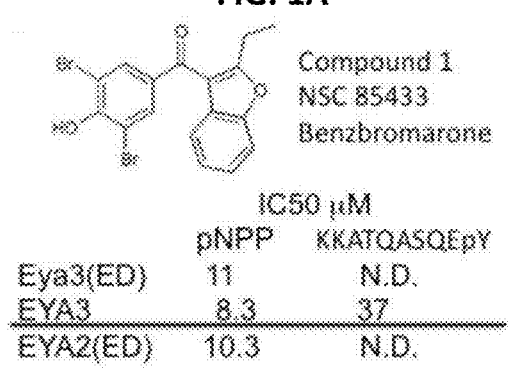
FIGS. 1A-D describe characterization of compound 1.

It is to be understood that both the foregoing general description and the following detailed description are exemplary and explanatory only and are not restrictive of the embodiments claimed. In this application, the use of the singular includes the plural unless specifically stated otherwise. In this application, the use of "or" means "and/or" unless stated otherwise. Furthermore, use of the term "including" as well as other forms, such as "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

Provided are compounds, compositions and methods relating to the inhibition of EYA tyrosine phosphatase.

In some embodiments, the compounds, compositions and methods provided herein include a compound having the structure of Formula I:

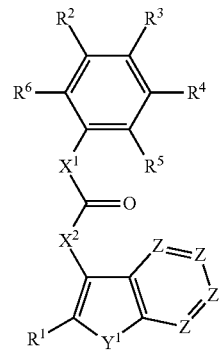

or a pharmaceutically acceptable salt thereof, wherein:
$R^1$ is selected from the group consisting of $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, (cyclolalkyl)alkyl, and amino, said $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, and (cyclolalkyl)alkyl are each optionally substituted with one or more $R^{1A}$;

each $R^{1A}$ is independently selected from the group consisting of hydroxy, halo, cyano, nitro, $C_{1-6}$ alkyl optionally substituted with up to 5 fluoro, $C_{1-6}$ alkoxy optionally substituted with up to 5 fluoro;

$R^2$ is selected from the group consisting of H (hydrogen), halo, hydroxy, and $C_{1-6}$ alkyl substituted with one or more hydroxy;

$R^3$ is selected from the group consisting of halo, hydroxy, and $C_{1-6}$ alkyl substituted with one or more hydroxy;

$R^4$ is H (hydrogen) or halo;

$R^5$ and $R^6$ are each independently selected from the group consisting of H (hydrogen), halo, cyano, $C_{1-6}$ alkyl, aryl, heteroaryl, heterocyclyl, and amino, said $C_{1-6}$ alkyl, aryl, heteroaryl, and heterocyclyl each optionally substituted with one or more $R^{1A}$;

$X^1$ is $[C(R^{2A})_2]_n$, O (oxygen), or $NR^{2A}$, or $X^1$ is absent;

$X^2$ is $[C(R^{2A})_2]_n$, O (oxygen), or $NR^{2A}$, or $X^2$ is absent;

each $R^{2A}$ is independently selected from the group consisting of H (hydrogen), halo, hydroxy, O-carbamyl, N-carbamyl, C-amido, S-sulfonamido, N-sulfonamido, C-carboxy, amino, aryl, heteroaryl, heterocyclyl, arylalkyl, heteroarylalkyl, heterocyclylalkyl, cycloalkyl, cycloalkenyl, (cyclolalkyl)alkyl, $C_{1-6}$ alkyl substituted with one or more hydroxyl, and $C_{1-6}$ alkyl optionally substituted with up to 5 fluoro;

each n is independently 1 or 2;

$Y^1$ is O (oxygen), S (sulfur), or $NR^{2A}$; and each Z is independently selected from the group consisting $CR^{2A}$, and N (nitrogen), with the proviso that the compound is not:

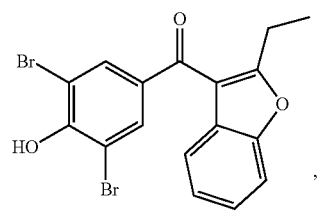

-continued

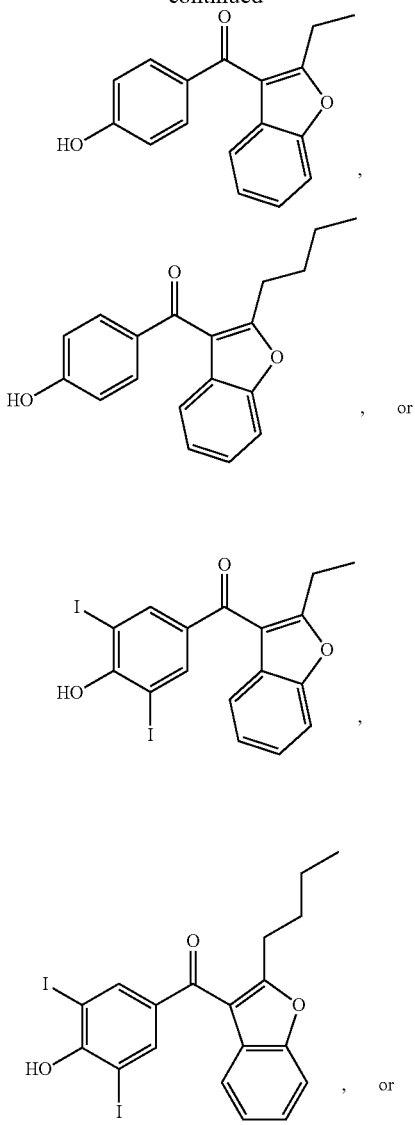

, or

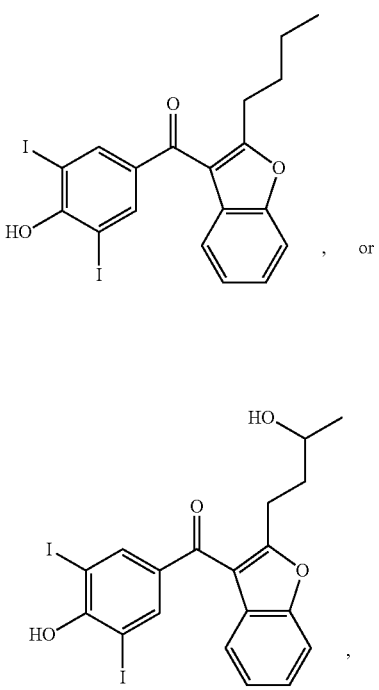

or a pharmaceutically acceptable salt thereof.

In some embodiments, $R^5$ and $R^6$ are H (hydrogen). In some embodiments, $R^2$ is iodo or bromo. In some embodiments, $R^4$ is iodo or bromo.

In some embodiments, the compound having the structure of Formula I may have the structure of Formula Ia, or Ib,

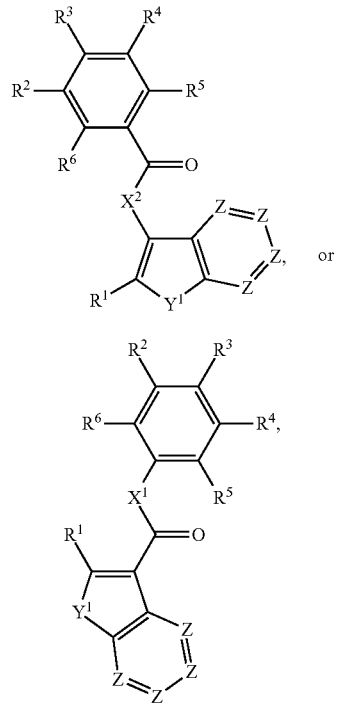

or a pharmaceutically acceptable salt thereof.

In some embodiments, $R^1$ is $C_{1-6}$ alkyl optionally substituted with one or more $R^{1A}$. In some embodiments, $X^1$ is $[C(R^{2A})_2]_n$ or $NR^{2A}$. In some embodiments, $X^2$ is $[C(R^{2A})_2]_n$ or $NR^{2A}$. In some embodiments, $Y^1$ is O (oxygen), or S (sulfur). In some embodiments, each Z is $CR^{2A}$, where each $R^{2A}$ is independently selected from the group consisting of H (hydrogen) and hydroxy. In some embodiments, $X^1$ or $X^2$ is $NR^{2A}$. In some embodiments, $X^2$ is $NR^{2A}$.

In some embodiments, each Z is CH.

In some embodiments, the compound having the structure of Formula I may have the structure of Formula II:

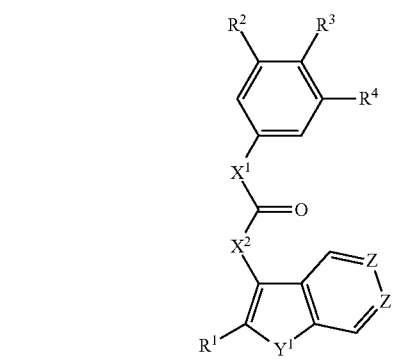

or a pharmaceutically acceptable salt thereof, wherein:
$X^1$ is O (oxygen), or $NR^{2A}$, or $X^1$ is absent;
$X^2$ is O (oxygen), or $NR^{2A}$, or $X^2$ is absent;
each $R^{2A}$ is independently selected from the group consisting of H (hydrogen), halo, hydroxy, $C_{1-6}$ alkyl substituted with one or more hydroxyl, and $C_{1-6}$ alkyl optionally substituted with up to 5 fluoro; and
$Y^1$ is O (oxygen), or S (sulfur).

In some embodiments, the compound having the structure of Formula II may have the structure of Formula IIa, or IIb,

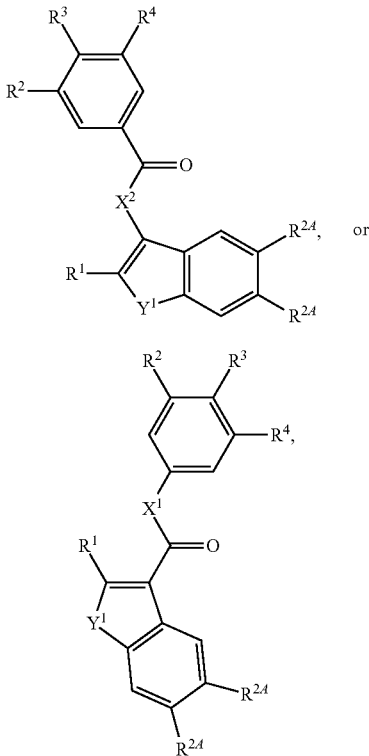

or a pharmaceutically acceptable salt thereof, wherein $R^2$ and $R^4$ are each independently H (hydrogen) or halo; and each $R^{2A}$ is independently hydrogen, halo or hydroxyl, wherein at least one $R^{2A}$ is hydroxyl.

In some embodiments, $R^1$ is $C_{1-6}$ alkyl optionally substituted with one or more hydroxy. In some embodiments, $X^1$ is or $NR^{2A}$. In some embodiments, $X^2$ is or $NR^{2A}$.

In some embodiments, the compound of Formula I may have the structure of Formula III:

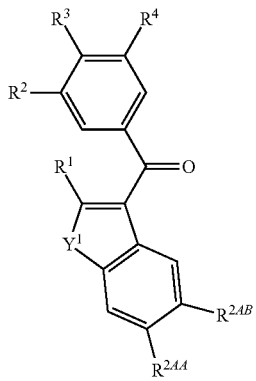

or a pharmaceutically acceptable salt thereof, wherein:
$R^3$ is halo or hydroxy;
$R^{2AA}$ is H (hydrogen) or hydroxyl;
$R^{2AB}$ is H (hydrogen) or hydroxyl; and $Y^1$ is O (oxygen), or S (sulfur). In some embodiments, $R^{2AA}$ is hydroxyl.

In some embodiments, $R^{2AB}$ is hydroxyl). In some embodiments, $R^{2AA}$ is H (hydrogen). In some embodiments, $R^{2AB}$ is H (hydrogen).

In some embodiments, $Y^1$ is O (oxygen). In some embodiments, R is selected from the group consisting of $C_{1-6}$ alkyl, cycloalkyl, (cycloalkyl)alkyl, each optionally substituted with one or more hydroxy. In some embodiments, $R^2$ is selected from the group consisting of halo, hydroxy, O-carbamyl, N-carbamyl, C-amido, N-amido, S-sulfonamido, N-sulfonamido, C-carboxy, O-carboxy, and $C_{1-3}$ alkyl substituted with one or more hydroxy. In some embodiments, $R^3$ is selected from the group consisting of hydroxy and $C_{1-3}$ alkyl substituted with one or more hydroxy. In some embodiments, $R^4$ is compound from the group consisting of halo, $C_{1-3}$ alkyl optionally substituted with up to 5 fluoro, and $C_{1-3}$ alkoxy optionally substituted with up to 5 fluoro.

In some embodiments, each $R^{2A}$ is independently selected from the group consisting of H (hydrogen), and $C_{1-6}$ alkyl optionally substituted with up to 5 fluoro. In some embodiments, each $R^{2A}$ is H (hydrogen). In some embodiments, $R^1$ is selected from the group consisting of $C_{1-3}$ alkyl, C-amido, and S-sulfonamido, said $C_{1-3}$ alkyl optionally substituted with one or more hydroxy. In some embodiments, $R^2$ is selected from the group consisting of hydroxy, C-amido, N-amido, S-sulfonamido, and $C_{1-3}$ alkyl substituted with hydroxy. In some embodiments, $R^3$ is selected from the group consisting of hydroxy, C-amido, and $C_{1-3}$ alkyl substituted with hydroxy. In some embodiments, $R^4$ is selected from the group consisting of fluoro, chloro, bromo, methyl, —$CF_3$, —$OCH_3$, and —$OCF_3$. In some embodiments, $R^2$ is selected from the group consisting of fluoro, chloro, bromo, and iodo. In some embodiments, $R^4$ is selected from the group consisting of fluoro, chloro, bromo, and iodo. In some embodiments, $R^1$ is substituted $C_{1-6}$ alkyl, and $R^{1A}$ is hydroxy. In some embodiments, $R^1$ is $C_{1-6}$ alkyl optionally substituted with one or more $R^{1A}$. In some embodiments, $R^1$ is ethyl. In some embodiments, $R^2$ is iodo or bromo. In some embodiments, $R^4$ is iodo or bromo.

In some embodiments, the compounds, compositions and methods provided herein include a compound having the structure of Formula IV

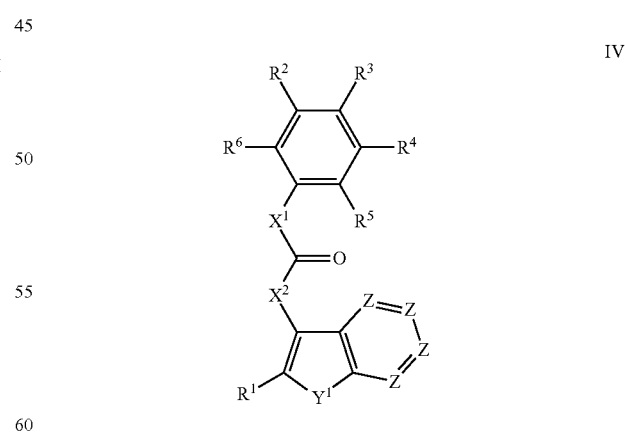

or a pharmaceutically acceptable salt thereof, wherein:
$R^1$ is selected from the group consisting of $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, (cycloalkyl)alkyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, and amino, said $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, and (cyclolalkyl)alkyl are each optionally substituted with one or more $R^{1A}$;

each $R^{1A}$ is independently selected from the group consisting of hydroxy, halo, cyano, nitro, $C_{1-6}$ alkyl optionally substituted with up to 5 fluoro, $C_{1-6}$ alkoxy optionally substituted with up to 5 fluoro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, and amino;

$R^2$ is selected from the group consisting of H (hydrogen), halo, hydroxy, O-carbamyl, N-carbamyl, O-thiocarbamyl, N-thiocarbamyl, C-amido, N-amido, S-sulfonamido, N-sulfonamido, C-carboxy, O-carboxy, and $C_{1-6}$ alkyl substituted with one or more hydroxy;

$R^3$ is selected from the group consisting of halo, hydroxy, O-carbamyl, N-carbamyl, C-amido, S-sulfonamido, N-sulfonamido, C-carboxy, amino, and $C_{1-6}$ alkyl substituted with one or more hydroxy;

$R^4$ is selected from the group consisting of H (hydrogen), halo, and $C_{1-6}$ alkyl optionally substituted with up to 5 fluoro and $C_{1-6}$ alkoxy optionally substituted with up to 5 fluoro;

$R^5$ and $R^6$ are each independently selected from the group consisting of H (hydrogen), halo, cyano, $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, (cyclolalkyl)alkyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, and amino, said $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, and (cyclolalkyl)alkyl each optionally substituted with one or more $R^{1A}$;

$X^1$ is $[C(R^{2A})_2]_n$, O (oxygen), or $NR^{2A}$, or $X^1$ is absent;

$X^2$ is $[C(R^{2A})_2]_n$, O (oxygen), or $NR^{2A}$, or $X^2$ is absent;

each $R^{2A}$ is independently selected from the group consisting of H (hydrogen), halo, hydroxy, O-carbamyl, N-carbamyl, C-amido, S-sulfonamido, N-sulfonamido, C-carboxy, amino, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, (cyclolalkyl) alkyl, $C_{1-6}$ alkyl substituted with one or more hydroxyl, and $C_{1-6}$ alkyl optionally substituted with up to 5 fluoro;

each n is independently 1 or 2;

$Y^1$ is O (oxygen), S (sulfur), or $NR^{2A}$; and each Z is independently selected from the group consisting $CR^{2A}$, and N (nitrogen).

In certain embodiments, a compound, composition or method as disclosed herein is provided, wherein the compound having the structure of Formula I has the structure of Formula Ia, or Ib,

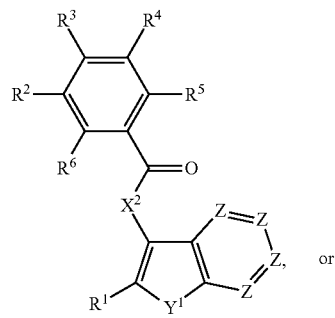

(Ia)

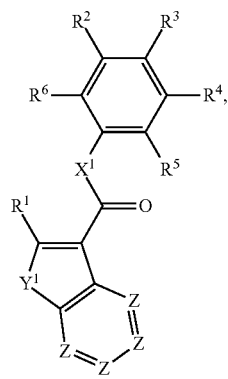

(Ib)

or a pharmaceutically acceptable salt thereof.

In certain embodiments, a compound, composition or method as disclosed herein is provided, wherein the compound having the structure of Formula I has the structure of Formula II:

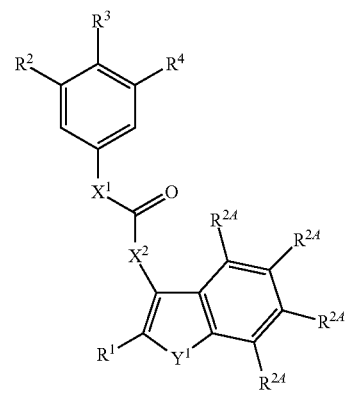

II or a pharmaceutically acceptable salt thereof, wherein:
$R^1$ is selected from the group consisting of $C_{1-6}$ alkyl, $C_{2-6}$ alkenyl, $C_{2-6}$ alkynyl, aryl, arylalkyl, cycloalkyl, cycloalkenyl, (cyclolalkyl)alkyl, C-amido, N-amido, S-sulfonamido, and N-sulfonamido, said $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, and (cyclolalkyl)alkyl are each optionally substituted with one or more $R^{1A}$;

$X^1$ is O (oxygen), or $NR^{2A}$, or $X^1$ is absent;
$X^2$ is O (oxygen), or $NR^{2A}$, or $X^2$ is absent;
each $R^{2A}$ is independently selected from the group consisting of H (hydrogen), halo, hydroxy, O-carbamyl, N-carbamyl, C-amido, S-sulfonamido, N-sulfonamido, C-carboxy, amino, $C_{2-6}$ alkenyl, $C_{2-6}$ alkynyl, aryl, arylalkyl, cycloalkyl, cycloalkenyl, (cyclolalkyl)alkyl, $C_{1-6}$ alkyl substituted with one or more hydroxyl, and $C_{1-6}$ alkyl optionally substituted with up to 5 fluoro; and $Y^1$ is O (oxygen), or S (sulfur).

In certain embodiments, a compound, composition or method as disclosed herein is provided, wherein the compound having the structure of Formula II has the structure of Formula IIa, or IIb:

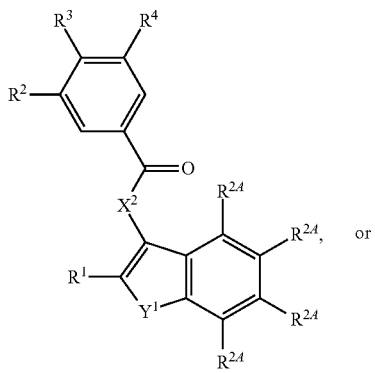

(IIa)

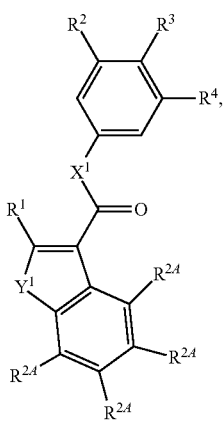

(IIb)

or a pharmaceutically acceptable salt thereof.

In certain embodiments, a compound, composition or method as disclosed herein is provided, wherein the compound having the structure of Formula I has the structure of Formula III:

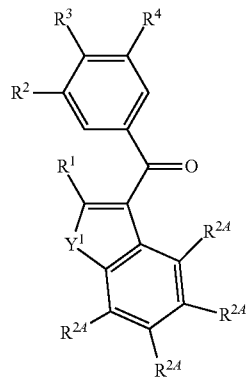

III or a pharmaceutically acceptable salt thereof, wherein:
$R^1$ is selected from the group consisting of $C_{1-6}$ alkyl, $C_{2-6}$ alkenyl, $C_{2-6}$ alkynyl, cycloalkyl, cycloalkenyl, (cyclolalkyl)alkyl, C-amido, N-amido, S-sulfonamido, N-sulfonamido, said $C_{1-6}$ alkyl, $C_{2-6}$ alkenyl, $C_{2-6}$ alkynyl, cycloalkyl, cycloalkenyl, (cyclolalkyl)alkyl are each optionally substituted with one or more $R^{1A}$;

each $R^{1A}$ is independently selected from the group consisting of hydroxy, halo, $C_{1-6}$ alkyl substituted with up to 5 fluoro, and $C_{1-6}$ alkoxy optionally substituted with up to 5 fluoro;

each $R^{2A}$ is independently selected from the group consisting of H (hydrogen), halo, hydroxy, O-carbamyl, N-carbamyl, C-amido, S-sulfonamido, N-sulfonamido, C-carboxy, amino, $C_{2-6}$ alkenyl, $C_{2-6}$ alkynyl, aryl, arylalkyl, cycloalkyl, cycloalkenyl, (cyclolalkyl)alkyl, $C_{1-6}$ alkyl substituted with one or more hydroxyl, and $C_{1-6}$ alkyl optionally substituted with up to 5 fluoro; and $Y^1$ is O (oxygen), or S (sulfur).

In certain embodiments, a compound, composition or method as disclosed herein is provided wherein $R^5$ and $R^6$ are H (hydrogen).

In certain embodiments, a compound, composition or method as disclosed herein is provided wherein $R^1$ is selected from the group consisting of $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, (cyclolalkyl)alkyl, O-carbamyl, N-carbamyl, O-thiocarbamyl, N-thiocarbamyl, C-amido, S-sulfonamido, and N-sulfonamido, said $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, and (cyclolalkyl)alkyl are each optionally substituted with one or more $R^{1A}$.

In certain embodiments, a compound, composition or method as disclosed herein is provided wherein $R^1$ is $C_{1-6}$ alkyl. In certain embodiments, a compound, composition or method as disclosed herein is provided wherein $R^1$ is substituted $C_{1-6}$ alkyl, and $R^{1A}$ is hydroxy.

In certain embodiments, a compound, composition or method as disclosed herein is provided wherein $X^1$ is $[C(R^{2A})_2]_n$ or $NR^{2A}$.

In certain embodiments, a compound, composition or method as disclosed herein is provided wherein $X^2$ is $[C(R^{2A})_2]_n$ or $NR^{2A}$.

In certain embodiments, a compound, composition or method as disclosed herein is provided wherein $Y^1$ is O (oxygen), or S (sulfur).

In certain embodiments, a compound, composition or method as disclosed herein is provided wherein each Z is $CR^{2A}$, where each $R^{2A}$ is independently selected from the group consisting of H (hydrogen), hydroxy, and $C_{1-6}$ alkyl optionally substituted with up to 5 fluoro.

In certain embodiments, a compound, composition or method as disclosed herein is provided wherein $R^1$ is selected from the group consisting of $C_{1-3}$ alkyl, C-amido, and S-sulfonamido, said $C_{1-3}$ alkyl optionally substituted with one or more hydroxy. In certain embodiments, a compound, composition or method as disclosed herein is provided wherein $R^1$ is $C_{1-6}$ alkyl. In certain embodiments, a compound, composition or method as disclosed herein is provided wherein $R^1$ is substituted $C_{1-6}$ alkyl, and $R^{1A}$ is hydroxy.

In certain embodiments, a compound, composition or method as disclosed herein is provided wherein $R^2$ is selected from the group consisting of hydroxy, C-amido, N-amido, S-sulfonamido, and $C_{1-3}$ alkyl substituted with hydroxy. In certain embodiments, a compound, composition or method as disclosed herein is provided wherein $R^2$ is bromo. In certain embodiments, a compound, composition or method as disclosed herein is provided wherein $R^2$ is iodo.

In certain embodiments, a compound, composition or method as disclosed herein is provided wherein $R^3$ is selected from the group consisting of hydroxy, C-amido, and $C_{1-3}$ alkyl substituted with hydroxy.

In certain embodiments, a compound, composition or method as disclosed herein is provided wherein each Z is CH.

In certain embodiments, a compound, composition or method as disclosed herein is provided wherein $R^1$ is selected from the group consisting of $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, (cyclolalkyl)alkyl, each optionally substituted with one or more $R^{1A}$ In certain embodiments, a compound, composition or method as disclosed herein is provided wherein $R^1$ is $C_{1-6}$ alkyl. In certain embodiments, a compound, composition or method as disclosed herein is provided wherein $R^1$ is substituted $C_{1-6}$ alkyl, and $R^{1A}$ is hydroxy.

In certain embodiments, a compound, composition or method as disclosed herein is provided wherein $X^1$ is or $NR^{2A}$.

In certain embodiments, a compound, composition or method as disclosed herein is provided wherein $X^2$ is or $NR^{2A}$.

In certain embodiments, a compound, composition or method as disclosed herein is provided wherein $Y^1$ is O (oxygen).

In certain embodiments, a compound, composition or method as disclosed herein is provided wherein $R^1$ is selected from the group consisting of $C_{1-6}$ alkyl, cycloalkyl, (cyclolalkyl)alkyl, each optionally substituted with one or more $R^{1A}$.

In certain embodiments, a compound, composition or method as disclosed herein is provided wherein $R^2$ is selected from the group consisting of halo, hydroxy, O-carbamyl, N-carbamyl, C-amido, N-amido, S-sulfonamido, N-sulfonamido, C-carboxy, O-carboxy, and $C_{1-3}$ alkyl substituted with one or more hydroxy. In certain embodiments, a compound, composition or method as disclosed herein is provided wherein $R^2$ is bromo. In certain embodiments, a compound, composition or method as disclosed herein is provided wherein $R^2$ is iodo.

In certain embodiments, a compound, composition or method as disclosed herein is provided wherein $R^3$ is selected from the group consisting of hydroxy, C-amido, S-sulfonamido, N-sulfonamido, and $C_{1-3}$ alkyl substituted with one or more hydroxy.

In certain embodiments, a compound, composition or method as disclosed herein is provided wherein $R^4$ is selected from the group consisting of halo, $C_{1-3}$ alkyl optionally substituted with up to 5 fluoro, and $C_{1-3}$ alkoxy optionally substituted with up to 5 fluoro. In certain embodiments, a compound, composition or method as disclosed herein is provided wherein $R^4$ is bromo. In certain embodiments, a compound, composition or method as disclosed herein is provided wherein $R^4$ is iodo.

In certain embodiments, a compound, composition or method as disclosed herein is provided wherein each $R^{2A}$ is independently selected from the group consisting of H (hydrogen), hydroxy, and $C_{1-6}$ alkyl optionally substituted with up to 5 fluoro.

In certain embodiments, a compound, composition or method as disclosed herein is provided wherein each $R^{2A}$ is H (hydrogen).

In certain embodiments, a compound, composition or method as disclosed herein is provided wherein $R^1$ is selected from the group consisting of $C_{1-3}$ alkyl, C-amido, and S-sulfonamido, said $C_{1-3}$ alkyl optionally substituted with one or more hydroxy.

In certain embodiments, a compound, composition or method as disclosed herein is provided wherein $R^2$ is selected from the group consisting of hydroxy, C-amido, N-amido, S-sulfonamido, and $C_{1-3}$ alkyl substituted with hydroxy.

In certain embodiments, a compound, composition or method as disclosed herein is provided wherein $R^3$ is selected from the group consisting of hydroxy, C-amido, and $C_{1-3}$ alkyl substituted with hydroxy.

In certain embodiments, a compound, composition or method as disclosed herein is provided wherein $R^4$ is selected from the group consisting of fluoro, chloro, bromo, methyl, —$CF_3$, —$OCH_3$, and —$OCF_3$.

In certain embodiments, a compound, composition or method as disclosed herein is provided wherein the compound is not:

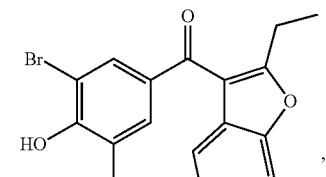

,

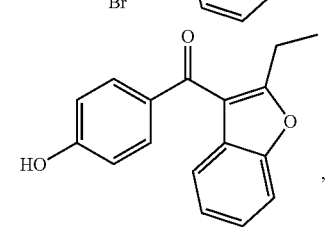

,

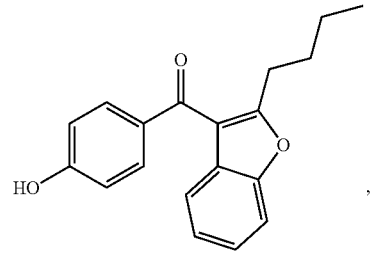

, or or a pharmaceutically acceptable salt thereof.

In certain embodiments, a compound, composition or method as disclosed herein is provided wherein the compound is not:

or a pharmaceutically acceptable salt thereof. In certain embodiments, a compound, composition or method as disclosed herein is provided wherein the compound is not:

-continued
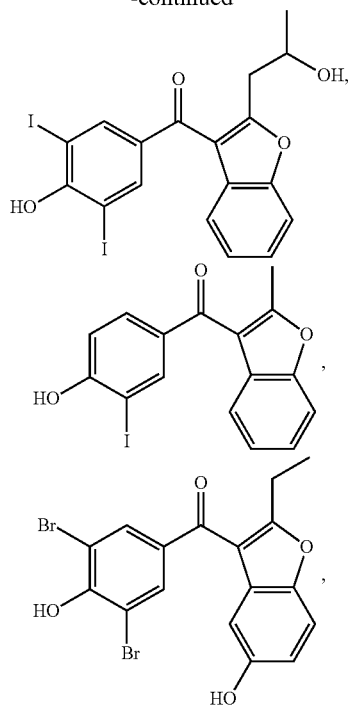
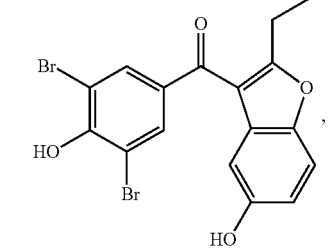
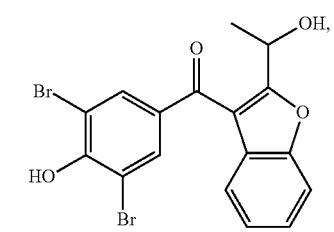
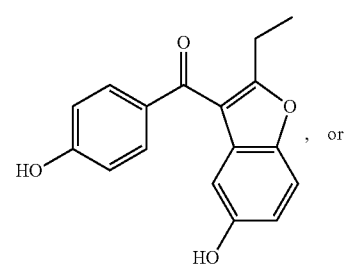
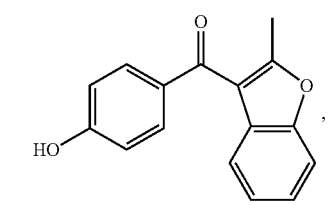
, or
or a pharmaceutically acceptable salt thereof. In certain embodiments, a compound, composition or method as disclosed herein is provided wherein the compound is not:
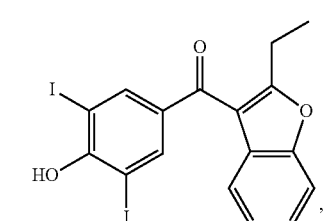
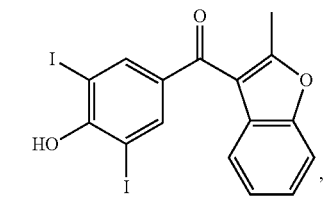
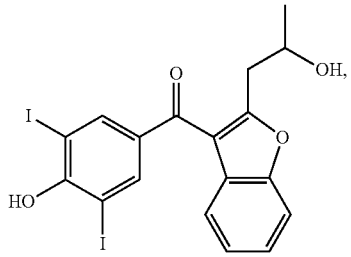
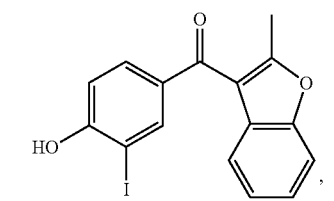
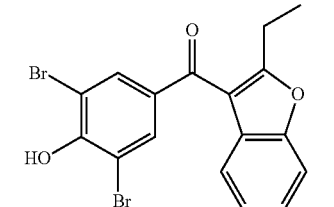
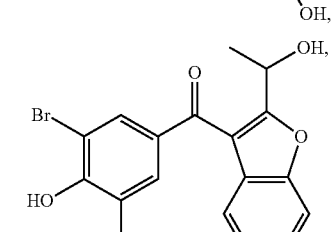
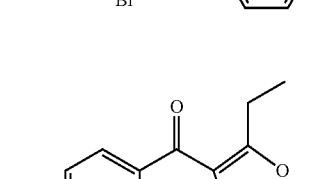
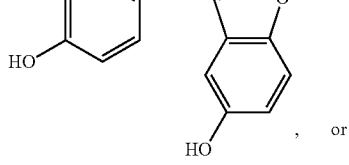
, or

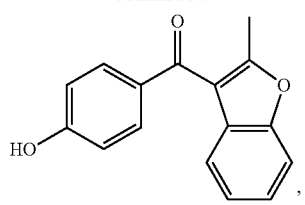
or a pharmaceutically acceptable salt thereof.
In certain embodiments, a compound, composition or method as disclosed herein is provided wherein the compound is:
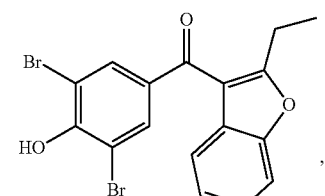
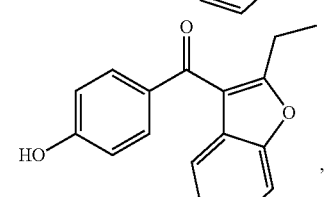
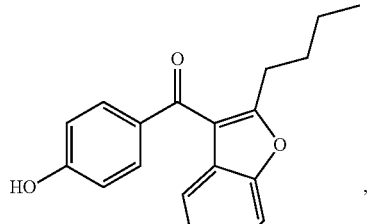
, or
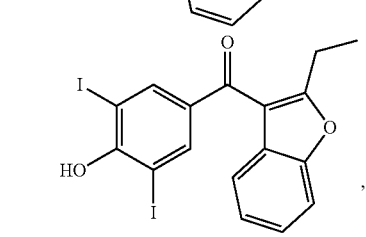
or a pharmaceutically acceptable salt thereof.
In certain embodiments, a compound, composition or method as disclosed herein is provided wherein the compound is:
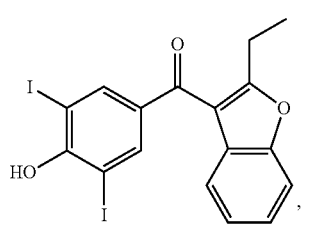
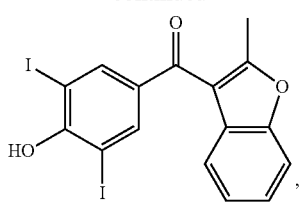
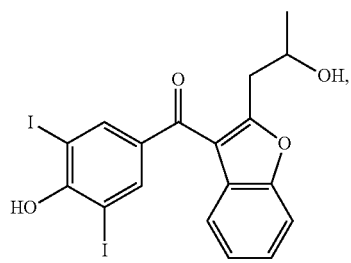
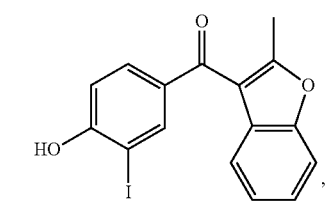
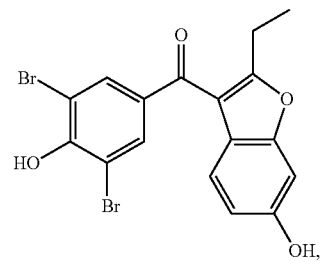
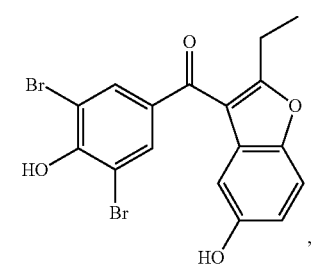
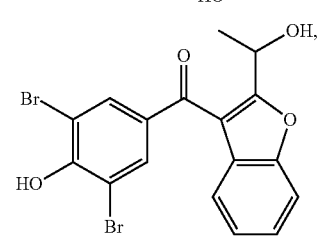
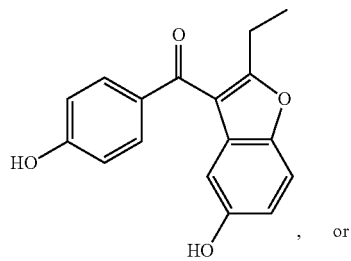
, or -continued

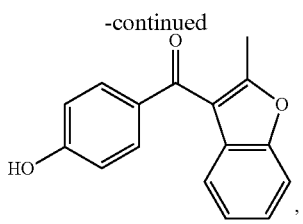

, or a pharmaceutically acceptable salt thereof.

In certain embodiments, a compound, composition or method as disclosed herein is provided wherein the compound is:

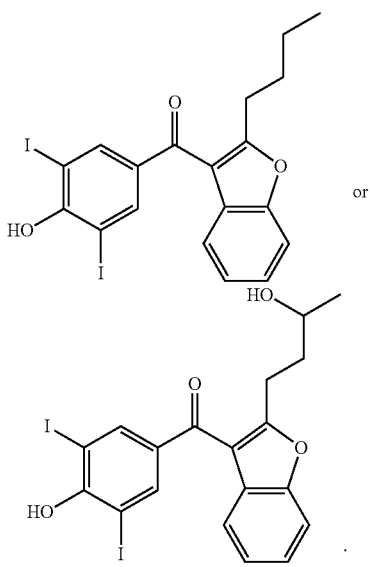

or

In certain embodiments, a compound, composition or method as disclosed herein is provided wherein the compound is not:

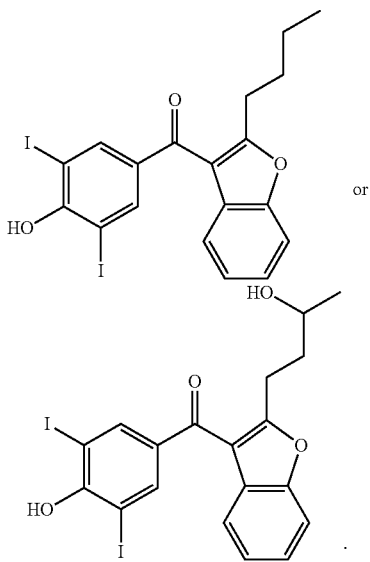

or

In certain embodiments, a compound, composition or method as disclosed herein is provided wherein the compound is:

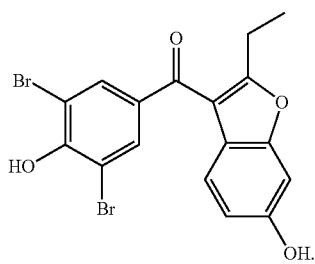 [SMILES: CCc1oc2cc(O)ccc2c1C(=O)c1cc(Br)c(O)c(Br)c1]

In certain embodiments, a compound, composition or method as disclosed herein is provided wherein $R^1$ is selected from the group consisting of $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, (cyclolalkyl)alkyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, and amino, said $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, and (cyclolalkyl)alkyl are each optionally substituted with one or more $R^{1A}$; each $R^{1A}$ is independently selected from the group consisting of hydroxy, halo, cyano, nitro, $C_{1-6}$ alkyl optionally substituted with up to 5 fluoro, $C_{1-6}$ alkoxy optionally substituted with up to 5 fluoro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, and amino; $R^2$ is selected from the group consisting of H (hydrogen), halo, hydroxy, O-carbamyl, N-carbamyl, O-thiocarbamyl, N-thiocarbamyl, C-amido, N-amido, S-sulfonamido, N-sulfonamido, C-carboxy, O-carboxy, and $C_{1-6}$ alkyl substituted with one or more hydroxy; $R^3$ is selected from the group consisting of halo, hydroxy, O-carbamyl, N-carbamyl, C-amido, S-sulfonamido, N-sulfonamido, C-carboxy, amino, and $C_{1-6}$ alkyl substituted with one or more hydroxy; $R^4$ is selected from the group consisting of H (hydrogen), halo, and $C_{1-6}$ alkyl optionally substituted with up to 5 fluoro and $C_{1-6}$ alkoxy optionally substituted with up to 5 fluoro; $R^5$ and $R^6$ are each independently selected from the group consisting of H (hydrogen), halo, cyano, $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, (cyclolalkyl)alkyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, and amino, said $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, and (cyclolalkyl)alkyl each optionally substituted with one or more $R^{1A}$; $X^1$ is $[C(R^{2A})_2]_n$, O (oxygen), or $NR^{2A}$, or $X^1$ is absent; $X^2$ is $[C(R^{2A})_2]_n$, O (oxygen), or $NR^{2A}$, or $X^2$ is absent; each $R^{2A}$ is independently selected from the group consisting of H (hydrogen), halo, hydroxy, O-carbamyl, N-carbamyl, C-amido, S-sulfonamido, N-sulfonamido, C-carboxy, amino, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, (cyclolalkyl)alkyl, $C_{1-6}$ alkyl substituted with one or more hydroxyl, and $C_{1-6}$ alkyl optionally substituted with up to 5 fluoro; each n is independently 1 or 2; $Y^1$ is O (oxygen), S (sulfur), or $NR^{24}$; and each Z is independently selected from the group consisting $CR^{24}$, and N (nitrogen), with the proviso that the compound is not:

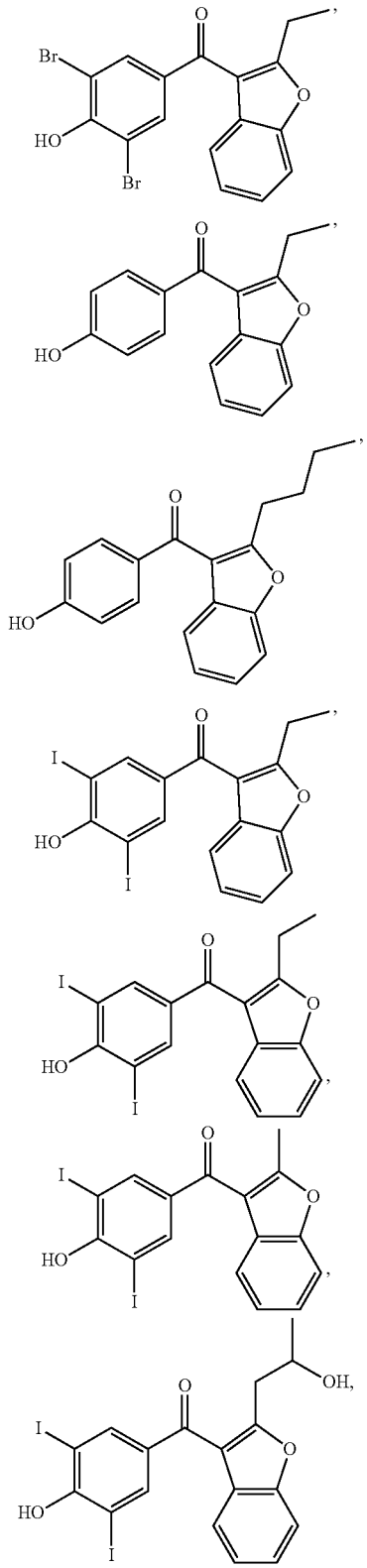

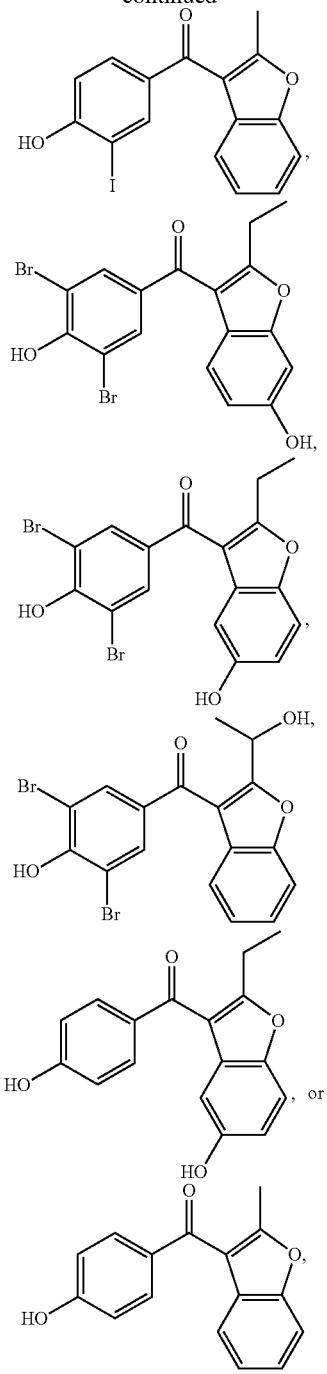

or a pharmaceutically acceptable salt thereof.

In certain embodiments, a compound, composition or method as disclosed herein is provided wherein $R^1$ is selected from the group consisting of $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, (cyclolalkyl)alkyl, O-carbamyl, N-carbamyl, O-thiocarbamyl, N-thiocarbamyl, C-amido, S-sulfonamido, and N-sulfonamido, said $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, and (cyclolalkyl) alkyl are each optionally substituted with one or more $R^{14}$.

In certain embodiments, a compound, composition or method as disclosed herein is provided wherein $X^1$ is $[C(R^{2A})_2]_n$ or $NR^{2A}$.

In certain embodiments, a compound, composition or method as disclosed herein is provided wherein $X^2$ is $[C(R^{2A})_2]_n$ or $NR^{2A}$.

In certain embodiments, a compound, composition or method as disclosed herein is provided wherein $Y^1$ is O (oxygen), or S (sulfur).

In certain embodiments, a compound, composition or method as disclosed herein is provided wherein each Z is $CR^{2A}$, where each $R^{2A}$ is independently selected from the group consisting of H (hydrogen), hydroxy, and $C_{1-6}$ alkyl optionally substituted with up to 5 fluoro.

In certain embodiments, a compound, composition or method as disclosed herein is provided wherein $X^1$ is $NR^{2A}$.

In certain embodiments, a compound, composition or method as disclosed herein is provided wherein $X^2$ is $NR^{2A}$.

In certain embodiments, a compound, composition or method as disclosed herein is provided wherein each Z is CH.

In certain embodiments, a compound, composition or method as disclosed herein is provided wherein $X^1$ is O (oxygen), or $NR^{2A}$, or $X^1$ is absent; $X^2$ is O (oxygen), or $NR^{2A}$, or $X^2$ is absent; each $R^{2A}$ is independently selected from the group consisting of H (hydrogen), halo, hydroxy, O-carbamyl, N-carbamyl, C-amido, S-sulfonamido, N-sulfonamido, C-carboxy, amino, $C_{2-6}$ alkenyl, $C_{2-6}$ alkynyl, aryl, arylalkyl, cycloalkyl, cycloalkenyl, (cyclolalkyl)alkyl, $C_{1-6}$ alkyl substituted with one or more hydroxyl, and $C_{1-6}$ alkyl optionally substituted with up to 5 fluoro; and $Y^1$ is O (oxygen), or S (sulfur).

In certain embodiments, a compound, composition or method as disclosed herein is provided wherein $R^1$ is selected from the group consisting of $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, (cyclolalkyl)alkyl, each optionally substituted with one or more $R^{1A}$.

In certain embodiments, a compound, composition or method as disclosed herein is provided wherein $R^1$ is selected from the group consisting of $C_{1-6}$ alkyl, $C_{2-6}$ alkenyl, $C_{2-6}$ alkynyl, cycloalkyl, cycloalkenyl, (cyclolalkyl) alkyl, C-amido, N-amido, S-sulfonamido, N-sulfonamido, said $C_{1-6}$ alkyl, $C_{2-6}$ alkenyl, $C_{2-6}$ alkynyl, cycloalkyl, cycloalkenyl, (cyclolalkyl)alkyl are each optionally substituted with one or more $R^{1A}$; each $R^{1A}$ is independently selected from the group consisting of hydroxy, halo, $C_{1-6}$ alkyl substituted with up to 5 fluoro, and $C_{1-6}$ alkoxy optionally substituted with up to 5 fluoro; $R^3$ is selected from the group consisting of halo, hydroxy, O-carbamyl, N-carbamyl, C-amido, S-sulfonamido, N-sulfonamido, C-carboxy, and $C_{1-6}$ alkyl substituted with one or more hydroxy; each $R^{2A}$ is independently selected from the group consisting of H (hydrogen), halo, hydroxy, O-carbamyl, N-carbamyl, C-amido, S-sulfonamido, N-sulfonamido, C-carboxy, amino, $C_{2-6}$ alkenyl, $C_{2-6}$ alkynyl, aryl, arylalkyl, cycloalkyl, cycloalkenyl, (cyclolalkyl)alkyl, $C_{1-6}$ alkyl substituted with one or more hydroxyl, and $C_{1-6}$ alkyl optionally substituted with up to 5 fluoro; and $Y^1$ is O (oxygen), or S (sulfur).

In certain embodiments, a compound, composition or method as disclosed herein is provided wherein $R^1$ is selected from the group consisting of $C_{1-6}$ alkyl, cycloalkyl, (cyclolalkyl)alkyl, each optionally substituted with one or more $R^{1A}$.

In certain embodiments, a compound, composition or method as disclosed herein is provided wherein $R^2$ is selected from the group consisting of halo, hydroxy, O-carbamyl, N-carbamyl, C-amido, N-amido, S-sulfonamido, N-sulfonamido, C-carboxy, O-carboxy, and $C_{1-3}$ alkyl substituted with one or more hydroxy.

In certain embodiments, a compound, composition or method as disclosed herein is provided wherein $R^3$ is selected from the group consisting of hydroxy, C-amido, S-sulfonamido, N-sulfonamido, and $C_{1-3}$ alkyl substituted with one or more hydroxy.

In certain embodiments, a compound, composition or method as disclosed herein is provided wherein $R^4$ is compound from the group consisting of halo, $C_{1-3}$ alkyl optionally substituted with up to 5 fluoro, and $C_{1-3}$ alkoxy optionally substituted with up to 5 fluoro.

In certain embodiments, a compound, composition or method as disclosed herein is provided wherein each $R^{2A}$ is independently selected from the group consisting of H (hydrogen), hydroxy, and $C_{1-6}$ alkyl optionally substituted with up to 5 fluoro.

In certain embodiments, a compound, composition or method as disclosed herein is provided wherein each $R^{2A}$ is H (hydrogen).

In certain embodiments, a compound, composition or method as disclosed herein is provided wherein $R^1$ is selected from the group consisting of $C_{1-3}$ alkyl, C-amido, and S-sulfonamido, said $C_{1-3}$ alkyl optionally substituted with one or more hydroxy.

In certain embodiments, a compound, composition or method as disclosed herein is provided wherein $R^2$ is selected from the group consisting of hydroxy, C-amido, N-amido, S-sulfonamido, and $C_{1-3}$ alkyl substituted with hydroxy.

In certain embodiments, a compound, composition or method as disclosed herein is provided wherein $R^3$ is selected from the group consisting of hydroxy, C-amido, and $C_{1-3}$ alkyl substituted with hydroxy.

In certain embodiments, a compound, composition or method as disclosed herein is provided wherein $R^4$ is selected from the group consisting of fluoro, chloro, bromo, methyl, —$CF_3$, —$OCH_3$, and —$OCF_3$. In certain embodiments, a compound, composition or method as disclosed herein is provided wherein $R^2$ is bromo and $R^4$ is bromo. In certain embodiments, a compound, composition or method as disclosed herein is provided wherein $R^2$ is iodo and $R^4$ is iodo.

Some embodiments provide a composition comprising a pharmaceutically acceptable excipient, and a compound of any of the embodiments as disclosed and described herein. In certain embodiments, the compound is:

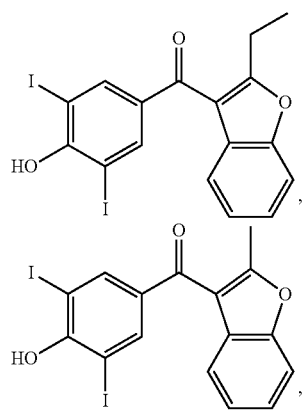

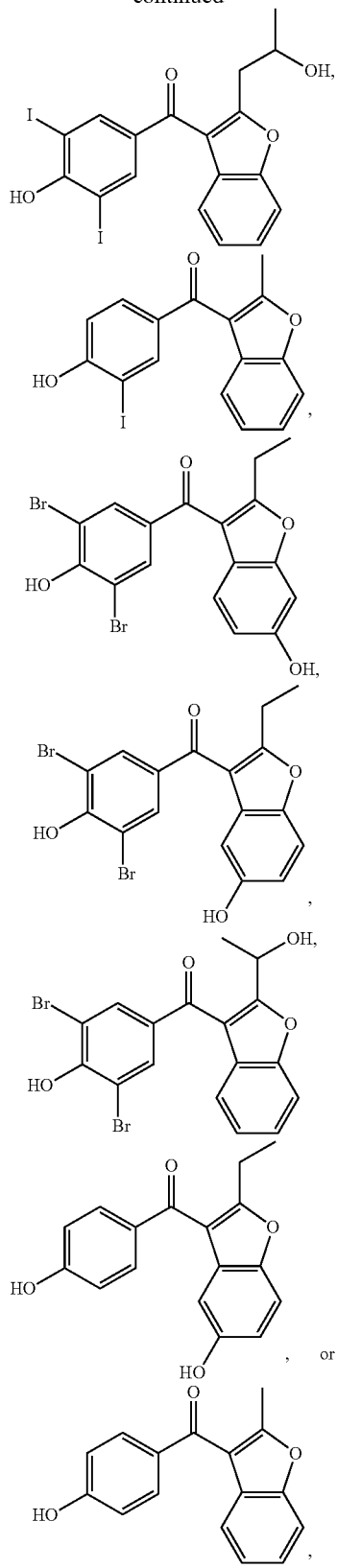

or a pharmaceutically acceptable salt thereof.

Some embodiments are directed to a method of treatment of an Eya-related disorder. One pathway implicated in proliferative disorders such as cancer is the evolutionarily conserved gene network termed the retinal determination gene network, or "RDGN." Indeed, the Six and Eya families of genes, members of the RDGN, are frequently found upregulated in cancers. The Eya protein has been shown to be a protein tyrosine phosphatase (PTP). PTPs in general are emerging as important new targets for cancer therapy. Antivascular therapy has emerged as an extremely promising option for the treatment of several major diseases including solid tumors and hematological cancers, and the vision-compromising ailments, such as diabetic retinopathy, age-related macular degeneration (AMD) and retinopathy of prematurity (ROP). Also presented herein is a compound of any of the embodiments as disclosed and described herein for use in treating proliferative retinopathy, retinopathy of prematurity, diabetic retinopathy, age related macular degeneration, retinal vasculitis, exudative vitreoretinopathy, tumor angiogenesis, hemangiomas, tumor metastasis, treating breast cancer, ductal carcinoma lobule carcinoma, breast epithelial cancer, ovarian cancer, including epithelial ovarian cancer, desmoid tumor, malignant peripheral nerve sheath cancer, acute leukemia, rhabdomyosarcoma, Ewing's sarcoma, extra-skeletal myxoid chondrosarcoma, or endometrial cancer in an individual. Also presented herein is a compound of any of the embodiments as disclosed and described herein for use in treating breast cancer, ductal carcinoma lobule carcinoma, breast epithelial cancer, ovarian cancer, including epithelial ovarian cancer, desmoid tumor, malignant peripheral nerve sheath cancer, acute leukemia, rhabdomyosarcoma, Ewing's sarcoma, extra-skeletal myxoid chondrosarcoma, or endometrial cancer in an individual. In certain embodiments, the compound is:

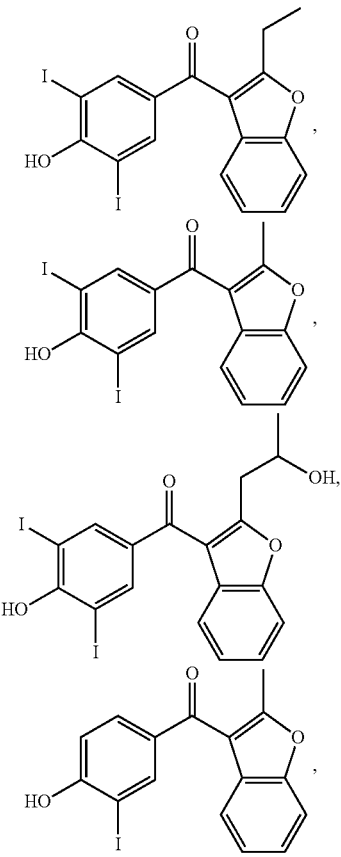

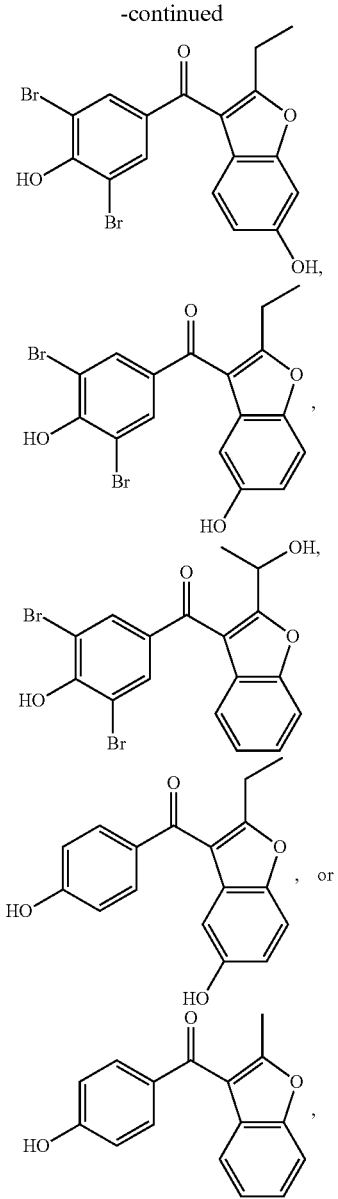

or a pharmaceutically acceptable salt thereof. In certain embodiments, the compound is:

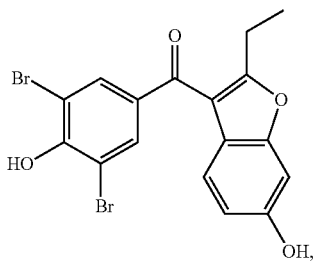 [SMILES: CCc1oc2cc(O)ccc2c1C(=O)c1cc(Br)c(O)c(Br)c1]

or a pharmaceutically acceptable salt thereof.

The protein tyrosine phosphatases (PTPs) of the Eyes Absent family are highly likely to be useful drug targets in anti-vascular therapy. Eyes Absent phosphatases are expressed in vascular endothelial cells (VECs) and the phosphatase activity enhances cell migration and the formation of vessel-like structures in culture. Agents that specifically target PTPs have enormous potential in the treatment of proliferative, invasive and/or metastatic, angiogenic and/or vascular disorders such as cancer, given the significant increase in PTP activity in many disease states. Though approximately 30% of cellular proteins are phospho-proteins, tyrosine phosphorylation accounts for only about 0.01% to about 0.05% of all phospho-proteins. In disease states such as oncogenic transformation, however, tyrosine phosphorylation is increased up to one to two hundred-fold to 1 to 2% of the total phospho-protein population. While protein tyrosine phosphatases have been extensively linked with disease states including proliferative diseases such as cancer, effective tyrosine phosphatase inhibitors have traditionally been confounded by a lack of specificity, and there remains a significant need in identifying PTP specific inhibitors for the treatment of disorders involving PTP dysregulation.

The inventors have characterized compounds that can inhibit the activity of the Eya protein, and, therefore, can have therapeutic effect.

Accordingly, in some embodiments, methods are provided for the treatment of proliferative retinopathy, retinopathy of prematurity, diabetic retinopathy, age related macular degeneration, retinal vasculitis, or exudative vitreoretinopathy.

In some embodiments, methods are provided for the treatment of tumor angiogenesis, hemangiomas or tumor metastasis.

In some embodiments, methods are provided for the treatment of breast cancer (including ductal carcinoma lobule carcinoma and breast epithelial cancer), ovarian cancer (including epithelial ovarian cancer), desmoid tumor, malignant peripheral nerve sheath cancer, acute leukemia, rhabdomyosarcoma, Ewing's sarcoma, extra-skeletal myxoid chondrosarcoma, or endometrial cancer.

In some embodiments, methods are provided for the treatment of Wilms' tumor, esophageal adenocarcinoma, colon cancer, colorectal cancer, esophageal squamous cell carcinoma, lung adenocarcinoma, Epstein-Barr virus-negative gastric cancer, or pancreatic ductal adenocarcinoma.

Some embodiments provide a method of evaluating the inhibition of EYA tyrosine phosphatase comprising contacting EYA tyrosine phosphatase with a compound of any of the embodiments as disclosed and described herein.

Some embodiments provide a method for evaluating the inhibition of EYA tyrosine phosphatase comprising: a) contacting the catalytic domain (ED) of EYA tyrosine phosphatase with a compound from a library of compounds and evaluating the results; and b) contacting a full-length EYA tyrosine phosphatase with said compound and evaluating the results. In certain embodiments, the method further comprises: c) performing a) for each compound in said library of compounds; d) selecting one or more compounds from c) that inhibit the catalytic domain (ED) of EYA tyrosine phosphatase according to a user-selected level; e) performing b) for each compound selected in d); and f) selecting one or more compounds from e) that inhibit full-length EYA tyrosine phosphatase according to a user-selected level.

Some embodiments provide a method for identifying a compound that specifically inhibits EYA tyrosine phosphatase comprising: a) contacting EYA tyrosine phosphatase with a compound and evaluating the results; and b) contacting a cysteine catalysis-based protein tyrosine phosphatase with said compound and evaluating the results.

Some embodiments provide a method of evaluating a compound for inhibition of cell migration, comprising contacting an EYA tyrosine phosphatase with a compound and evaluating the results.

Some embodiments provide a method of evaluating a compound for inhibition of tumor angiogenesis, comprising contacting an EYA tyrosine phosphatase with a compound and evaluating the results.

Some embodiments provide a method of evaluating a compound for inhibition of tumor metastasis, comprising contacting an EYA tyrosine phosphatase with a compound and evaluating the results.

Some embodiments provide a method of evaluating a compound for inhibition of proliferative retinopathy, comprising contacting an EYA tyrosine phosphatase with a compound and evaluating the results.

Some embodiments provide a method of evaluating a compound for inhibition of retinopathy of prematurity, comprising contacting an EYA tyrosine phosphatase with a compound and evaluating the results.

Some embodiments provide a method of evaluating a compound for inhibition of diabetic retinopathy, comprising contacting an EYA tyrosine phosphatase with a compound and evaluating the results.

Some embodiments provide a method of evaluating a compound for inhibition of age related macular degeneration, comprising contacting an EYA tyrosine phosphatase with a compound and evaluating the results.

Some embodiments provide a method of evaluating a compound for inhibition of retinal vasculitis, comprising contacting an EYA tyrosine phosphatase with a compound and evaluating the results.

Some embodiments provide a method of evaluating a compound for inhibition of exudative vitreoretinopathy, comprising contacting an EYA tyrosine phosphatase with a compound and evaluating the results.

Some embodiments provide a method of evaluating a compound for inhibition of hemangiomas comprising contacting an EYA tyrosine phosphatase with a compound and evaluating the results.

Some embodiments provide a method of evaluating a compound for inhibition of breast cancer (including ductal carcinoma lobule carcinoma and breast epithelial cancer) comprising contacting an EYA tyrosine phosphatase with a compound and evaluating the results.

Some embodiments provide a method of evaluating a compound for inhibition of ovarian cancer (including epithelial ovarian cancer) comprising contacting an EYA tyrosine phosphatase with a compound and evaluating the results.

Some embodiments provide a method of evaluating a compound for inhibition of desmoid tumor comprising contacting an EYA tyrosine phosphatase with a compound and evaluating the results.

Some embodiments provide a method of evaluating a compound for inhibition of malignant peripheral nerve sheath cancer comprising contacting an EYA tyrosine phosphatase with a compound and evaluating the results.

Some embodiments provide a method of evaluating a compound for inhibition of acute leukemia, rhabdomyosarcoma comprising contacting an EYA tyrosine phosphatase with a compound and evaluating the results.

Some embodiments provide a method of evaluating a compound for inhibition of Ewing's sarcoma comprising contacting an EYA tyrosine phosphatase with a compound and evaluating the results.

Some embodiments provide a method of evaluating a compound for inhibition of extra-skeletal myxoid chondrosarcoma comprising contacting an EYA tyrosine phosphatase with a compound and evaluating the results.

Some embodiments provide a method of evaluating a compound for inhibition of endometrial cancer comprising contacting an EYA tyrosine phosphatase with a compound and evaluating the results.

Some embodiments provide a method of evaluating a compound for inhibition of Wilms' tumor comprising contacting an EYA tyrosine phosphatase with a compound and evaluating the results.

Some embodiments provide a method of evaluating a compound for inhibition of esophageal adenocarcinoma comprising contacting an EYA tyrosine phosphatase with a compound and evaluating the results.

Some embodiments provide a method of evaluating a compound for inhibition of colon cancer comprising contacting an EYA tyrosine phosphatase with a compound and evaluating the results.

Some embodiments provide a method of evaluating a compound for inhibition of colorectal cancer comprising contacting an EYA tyrosine phosphatase with a compound and evaluating the results.

Some embodiments provide a method of evaluating a compound for inhibition of esophageal squamous cell carcinoma comprising contacting an EYA tyrosine phosphatase with a compound and evaluating the results.

Some embodiments provide a method of evaluating a compound for inhibition of lung adenocarcinoma comprising contacting an EYA tyrosine phosphatase with a compound and evaluating the results.

Some embodiments provide a method of evaluating a compound for inhibition of Epstein-Barr virus-negative gastric cancer comprising contacting an EYA tyrosine phosphatase with a compound and evaluating the results.

Some embodiments provide a method of evaluating a compound for inhibition of pancreatic ductal adenocarcinoma comprising contacting an EYA tyrosine phosphatase with a compound and evaluating the results.

In some embodiments, the results are evaluated by determining the level of inhibition of an EYA protein or truncated version thereof, relative to no inhibitor or relative to a control. In some embodiments, the results are evaluated by determining the level of inhibition of a full-length EYA protein or relative to a truncated EYA protein. In some embodiments, the results are evaluated by determining the level of reduction in pathological neovascularization relative to no inhibitor or relative to a control. In some embodiments, the results are evaluated by determining the level of reduction in angiogenesis relative to no inhibitor or relative to a control. In some embodiments, the results are evaluated by determining the level of reduction in metastasis to no inhibitor or relative to a control. In some embodiments, the results are evaluated by determining the level of reduction in tumor size relative to no inhibitor or relative to a control.

In certain aspects any of the embodiments providing methods said compound comprises a compound of any of the embodiments as disclosed and described herein.

In certain embodiments evaluating comprises evaluating the level of inhibition of full-length EYA tyrosine phosphatase in comparison with the level of inhibition of a truncated EYA tyrosine phosphatase. In certain embodiments, said truncated EYA tyrosine phosphatase comprises the catalytic domain of EYA tyrosine phosphatase. In certain embodiments, said truncated EYA tyrosine phosphatase comprises the catalytic domain (ED) of Eya3. In certain embodiments, said truncated EYA tyrosine phosphatase comprises the catalytic domain (ED) of Eya2.

In certain embodiments evaluating comprises evaluating the level of inhibition of EYA tyrosine phosphatase in comparison with the level of inhibition of a cysteine catalysis-based protein tyrosine phosphatase. In certain embodiments, said EYA tyrosine phosphatase comprises full-length EYA tyrosine phosphatase. In certain embodiments, said EYA tyrosine phosphatase comprises a truncated EYA tyrosine phosphatase which comprises the catalytic domain (ED) of EYA tyrosine phosphatase. In certain embodiments, said truncated EYA tyrosine phosphatase comprises the catalytic domain (ED) of Eya3. In certain embodiments, said truncated EYA tyrosine phosphatase comprises the catalytic domain (ED) of Eya2. In certain embodiments, said cysteine catalysis-based protein tyrosine phosphatase comprises PTP1B. In certain embodiments, said cysteine catalysis-based protein tyrosine phosphatase comprises FCP1. In certain embodiments, said cysteine catalysis-based protein tyrosine phosphatase comprises SCP. In certain embodiments, said cysteine catalysis-based protein tyrosine phosphatase comprises SH-PTP2. In certain embodiments, said cysteine catalysis-based protein tyrosine phosphatase comprises SH-PTP1.

Definitions

Unless specific definitions are provided, the nomenclatures utilized in connection with, and the laboratory procedures and techniques of, analytical chemistry, synthetic organic chemistry, and medicinal and pharmaceutical chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, pharmaceutical preparation, formulation, and delivery, and treatment of patients.

As used herein, the following terms are defined with the following meanings, unless expressly stated otherwise.

The term "alkyl" refers to a branched or unbranched fully saturated acyclic aliphatic hydrocarbon group. An alkyl may be branched or straight chain. Alkyls may be substituted or unsubstituted. Alkyls include, but are not limited to, methyl, ethyl, propyl, isopropyl, butyl, isobutyl, tertiary butyl, pentyl, hexyl, and the like, each of which may be optionally substituted.

In certain embodiments, an alkyl comprises 1 to 20 carbon atoms (whenever it appears herein, a numerical range such as "1 to 20" refers to each integer in the given range; e.g., "1 to 20 carbon atoms" means that an alkyl group may comprise only 1 carbon atom, 2 carbon atoms, 3 carbon atoms, etc., up to and including 20 carbon atoms, although the term "alkyl" also includes instances where no numerical range of carbon atoms is designated). An alkyl may be designated as "$C_1$-$C_6$ alkyl" or similar designations. By way of example only, "$C_1$-$C_4$ alkyl" indicates an alkyl having one, two, three, or four carbon atoms, e.g., the alkyl is selected from methyl, ethyl, propyl, iso-propyl, butyl, iso-butyl, sec-butyl, and tert-butyl.

The term "alkenyl" used herein refers to a straight or branched chain aliphatic hydrocarbon of from two to twenty carbon atoms containing at least one carbon-carbon double bond including, but not limited to, 1-propenyl, 2-propenyl, 2-methyl-1-propenyl, 1-butenyl, 2-butenyl, and the like. In certain embodiments, an alkenyl comprises 2 to 20 carbon atoms (whenever it appears herein, a numerical range such as "2 to 20" refers to each integer in the given range; e.g., "2 to 20 carbon atoms" means that an alkenyl group may comprise only 2 carbon atoms, 3 carbon atoms, etc., up to and including 20 carbon atoms, although the term "alkenyl" also includes instances where no numerical range of carbon atoms is designated). An alkenyl may be designated as "$C_2$-$C_6$ alkenyl" or similar designations. By way of example only, "$C_2$-$C_4$ alkenyl" indicates an alkenyl having two, three, or four carbon atoms, e.g., the alkenyl is selected from ethenyl, propenyl, and butenyl.

The term "cycloalkyl" used herein refers to saturated aliphatic ring system having three to twenty carbon atoms. A cycloalkyl refers to monocyclic and polycyclic saturated aliphatic ring system including, but not limited to, cyclopropyl, cyclopentyl, cyclohexyl, cycloheptyl, bicyclo[4.4.0]decanyl, bicyclo[2.2.1]heptanyl, adamantyl, norbornyl, and the like. In certain embodiments, a cycloalkyl comprises 3 to 20 carbon atoms (whenever it appears herein, a numerical range such as "3 to 20" refers to each integer in the given range; e.g., "3 to 20 carbon atoms" means that a cycloalkyl group may comprise only 3 carbon atoms, etc., up to and including 20 carbon atoms, although the term "cycloalkyl" also includes instances where no numerical range of carbon atoms is designated). A cycloalkyl may be designated as "$C_3$-$C_7$ cycloalkyl" or similar designations. By way of example only, "$C_3$-$C_6$ cycloalkyl" indicates a cycloalkyl having two, three, four, five or six carbon atoms, e.g., the cycloalkyl is selected from cyclopropyl, cyclobutyl, cyclopentyl, and cyclohexyl.

The term "cycloalkenyl" used herein refers to aliphatic ring system having three to twenty carbon atoms having at least one carbon-carbon double bond in the ring. A cycloalkenyl refers to monocyclic and polycyclic unsaturated aliphatic ring system including, but are not limited to, cyclopropenyl, cyclopentenyl, cyclohexenyl, cycloheptenyl, bicyclo[3.1.0]hexyl, norbornylenyl, 1,1'-bicyclopentenyl, and the like. In certain embodiments, a cycloalkenyl comprises 3 to 20 carbon atoms (whenever it appears herein, a numerical range such as "3 to 20" refers to each integer in the given range; e.g., "3 to 20 carbon atoms" means that a cycloalkenyl group may comprise only 3 carbon atoms, etc., up to and including 20 carbon atoms, although the term "cycloalkenyl" also includes instances where no numerical range of carbon atoms is designated). A cycloalkenyl may be designated as "$C_3$-$C_7$ cycloalkenyl" or similar designations. By way of example only, "$C_3$-$C_6$ cycloalkenyl" indicates an alkenyl having two, three, four, five or six carbon atoms, e.g., the cycloalkyl is selected from cyclopropenyl, cyclobutenyl, cyclopentenyl, and cyclohexenyl.

The term "alkoxy" used herein refers to straight or branched chain alkyl covalently bonded to oxygen where the "alkoxy" is attached to the parent molecule through at least an oxygen linkage. Where an "alkoxy" substituent requires two points of attachment to the rest of the molecule the "alkoxy" is attached to the parent molecule through an oxygen linkage and a carbon linkage. Examples of alkoxy groups include, but are not limited to, methoxy, ethoxy, propoxy, isopropoxy, butoxy, n-butoxy, sec-butoxy, t-butoxy and the like. An alkoxy may be designated as "$C_1$-$C_6$ alkoxy" or similar designations. By way of example only, "$C_1$-$C_4$ alkoxy" indicates an alkyl having one, two, three, or four carbon atoms, e.g., the alkoxy is selected from methoxy, ethoxy, propoxy, iso-propoxy, butoxy, iso-butoxy, sec-butoxy, and tert-butoxy.

The term "heteroalkyl" refers to a group comprising at least one alkyl or alkenyl, and one or two heteroatoms. Where a "heteroalkyl" substituent requires two points of attachment to the rest of the molecule the "heteroalkyl" is attached to the parent molecule through a heteroatom linkage and a carbon linkage, a first carbon linkage and a second carbon linkage, or a first heteroatom linkage and a second heteroatom linkage. Examples of heteroalkyls include, but are not limited to, —CH$_2$OCH$_2$CH$_2$—, —CH$_2$OCH$_2$—, —CH$_2$CH$_2$OCH$_2$CH$_2$—, —CH$_2$OCH=CH—, —CH=CHOCH=CH—, —OCH$_2$O—, —CH$_2$NHCH$_2$CH$_2$—, —CH$_2$NHCH$_2$—, —CH$_2$CH$_2$NHCH$_2$CH$_2$—, —NHCH=CH—, —NHCH$_2$CH$_2$—, —N=CHCH$_2$—, —CH$_2$NHCH=CH—, —CH=CHNHCH=CH—, —NHCH$_2$NH—, and the like.

The term "heterocyclic" or "heterocyclyl" used herein refers to a cyclic ring system radical having at least one non-aromatic ring in which one or more ring atoms are not carbon, namely heteroatom. Monocyclic "heterocyclic" or "heterocyclyl" moieties are non-aromatic. Bicyclic "heterocyclic" or "heterocyclyl" moieties include one non-aromatic ring wherein at least one heteroatom is present in a ring. Tricyclic "heterocyclic" or "heterocyclyl" moieties include at least one non-aromatic ring wherein at least one heteroatom is present in a ring. Examples of heterocyclic groups include, but are not limited to, piperidinyl, piperazinyl, morpholinyl, tetrahydrofuranyl, dioxolanyl, tetrahydropyranyl, pyrrolidinyl, and the like.

The term "heteroatom" refers to an atom other than carbon or hydrogen. Heteroatoms are typically independently selected from oxygen, sulfur, nitrogen, and phosphorus, but are not limited to those atoms. In embodiments in which two or more heteroatoms are present, the two or more heteroatoms may all be the same as one another, or some or all of the two or more heteroatoms may each be different from the others.

The term "aryl" refers to an aromatic group wherein each of the atoms forming the ring is a carbon atom. Examples of aryl groups include, but are not limited to phenyl, and naphthalenyl. In certain embodiments, a phenyl group is substituted at one or more positions. Examples of aryl groups comprising substitutions include, but are not limited to, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, hydroxynaphthyl, hydroxymethylphenyl, (trifluoromethyl)phenyl, and 4-morpholin-4-ylphenyl.

The term "heteroaryl" refers to an aromatic mono-, bi- or tricyclic ring system wherein at least one atom forming the aromatic ring system is a heteroatom. Heteroaryl rings may be formed by three, four, five, six, seven, eight, nine, or more than nine atoms. Heteroaryl groups may be optionally substituted. Examples of heteroaryl groups include, but are not limited to, aromatic C$_{3-8}$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl groups are optionally substituted with one or more substituents, independently selected from halo, hydroxy, amino, cyano, nitro, alkylamido, acyl, C$_{1-6}$-alkoxy, C$_{1-6}$-alkyl, C$_{1-6}$-hydroxyalkyl, C$_{1-6}$-aminoalkyl, C$_{1-6}$-alkylamino, alkylsulfenyl, alkylsulfinyl, alkylsulfonyl, sulfamoyl, or trifluoromethyl. In some embodiments, the substituents are halo, hydroxy, cyano, O—C$_{1-6}$-alkyl, C$_{1-6}$-alkyl, hydroxy-C$_{1-6}$-alkyl, and amino-C$_{1-6}$-alkyl. Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline.

The term "arylalkyl" refers to a group comprising an aryl group bound to an alkyl group. Examples of arylalkyl groups include, but are not limited to, benzyl, phenethyl, phenpropyl, phenbutyl, and the like. In some embodiments, arylalkyls may be substituted or unsubstituted, and can be substituted on either the aryl or alkyl portion or on both. Where an "arylalkyl" substituent requires two points of attachment to the rest of the molecule the "arylalkyl" can be attached to the parent molecule through a carbon linkage in the aryl group and a carbon linkage in the alkyl group.

The term "heteroarylalkyl" used herein refers to one or more heteroaryl groups appended to an alkyl radical. Examples of heteroarylalkyl include, but are not limited to, pyridylmethyl, furanylmethyl, thiopheneylethyl, and the like. In some embodiments, heteroarylalkyls may be substituted or unsubstituted, and can be substituted on either the heteroaryl or alkyl portion or on both. Where an "heteroarylalkyl" substituent requires two points of attachment to the rest of the molecule the "heteroarylalkyl" can be attached to the parent molecule through a carbon linkage in the heteroaryl group and a carbon linkage in the alkyl group.

The term "heterocyclylalkyl" used herein refers to one or more heterocyclyl groups appended to an alkyl radical. Examples of heterocyclylalkyl include, but are not limited to, piperidinylmethyl, piperidinylethyl, morpholinylmethyl, morpholinylethyl, and the like.

The term "(cycloalkyl)alkyl" used herein refers to one or more cycloalkyl groups appended to an alkyl radical. Examples of (cycloalkyl)alkyl include, but are not limited to, cyclohexylmethyl, cyclohexylethyl, cyclopentylmethyl, cyclopentylethyl, and the like. In some embodiments, (cycloalkyl)alkyl may be substituted or unsubstituted.

Unless otherwise indicated, the term "optionally substituted," refers to a group in which none, one, or more than one of the hydrogen atoms has been replaced with one or more group(s) individually and independently selected from: alkyl, alkenyl, cycloalkenyl, cycloalkyl, aryl, arylalkyl, heteroaryl, heterocyclyl, hydroxy, alkoxy, cyano, halo, oxo, thiocarbonyl, ester, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, and amino, including mono- and di-substituted amino groups, and the protected derivatives of amino groups. Such protective derivatives (and protecting groups that may form such protective derivatives) are known to those of skill in the art and may be found in references such as Greene and Wuts, above. When the group contains a nitrogen, or a sulfur, an oxo as a substituent also includes oxides, for example pyridine-N-oxide, thiopyran sulfoxide and thiopyran-S,S-dioxide. In embodiments in which two or more hydrogen atoms have been substituted, the substituent groups may together form a ring.

The substituent "R" appearing by itself and without a number designation refers to a substituent selected from H (hydrogen), alkyl, cycloalkyl, aryl, heteroaryl (bonded through a ring carbon) and heterocyclyl (bonded through a ring carbon).

The term "O-carboxy" refers to the group consisting of formula RC(=O)O—.

The term "C-carboxy" refers to the group consisting of formula —C(=O)OR.

The term "cyano" refers to the group consisting of formula —CN.

The term "isocyanato" refers to the group consisting of formula —N=C=O.

The term "thiocyanato" refers to the group consisting of formula —CNS.

The term "isothiocyanato" refers to the group consisting of formula —N=C=S.

The term "sulfonyl" refers to the group consisting of formula —S(=O)—R.

The term "S-sulfonamido" refers to the group consisting of formula —S(=O)$_2$NR.

The term "N-sulfonamido" refers to the group consisting of formula RS(=O)$_2$NH—.

The term "O-carbamyl" refers to the group consisting of formula —OC(=O)—NR.

The term "N-carbamyl" refers to the group consisting of formula ROC(=O)NH—.

The term "O-thiocarbamyl" refers to the group consisting of formula —OC(=S)—NR.

The term "N-thiocarbamyl" refers to the group consisting of formula ROC(=S)NH—.

The term "C-amido" refers to the group consisting of formula —C(=O)—NR$_2$.

The term "N-amido" refers to the group consisting of formula RC(=O)NH—.

The term "oxo" refers to the group consisting of formula =O.

The term "ester" refers to a chemical moiety with formula —(R)$_n$—C(=O)OR', where R and R' are independently selected from alkyl, cycloalkyl, aryl, heteroaryl (bonded through a ring carbon) and non-aromatic heterocycle (bonded through a ring carbon), where n is 0 or 1.

The term "amino" refers to a chemical moiety with formula —NHR'R", where R' and R" are each independently selected from hydrogen, alkyl, cycloalkyl, aryl, heteroaryl (bonded through a ring carbon) and heteroalicyclic (bonded through a ring carbon).

The term "stereoisomers" as used herein means isomers that possess identical constitution, but which differ in the arrangement of their atoms in space. Including, for example, all enantiomers, diastereomers, geometric isomers, and atropisomers.

Wherever a substituent as depicted as a di-radical (i.e., has two points of attachment to the rest of the molecule), it is to be understood that the substituent can be attached in any directional configuration unless otherwise indicated. Thus, for example, a substituent depicted as -AE- or

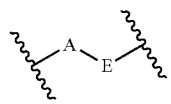

includes the substituent being oriented such that the A is attached at the leftmost attachment point of the molecule as well as attached at the rightmost attachment point of the molecule.

It is to be understood that certain radical naming conventions can include either a mono-radical or a di-radical, depending on the context. For example, where a substituent requires two points of attachment to the rest of the molecule, it is understood that the substituent is a di-radical. A substituent identified as alkyl, that requires two points of attachment, includes di-radicals such as —CH$_2$—, —CH$_2$CH$_2$—, —CH$_2$CH(CH$_3$)CH$_2$—, and the like; a substituent depicted as alkoxy that requires two points of attachment, includes di-radicals such as —OCH$_2$—, —OCH$_2$CH$_2$—, —OCH$_2$CH(CH$_3$)CH$_2$—, and the like: and a substituent identified as arylalkyl that requires two points of attachment, includes di-radicals such as

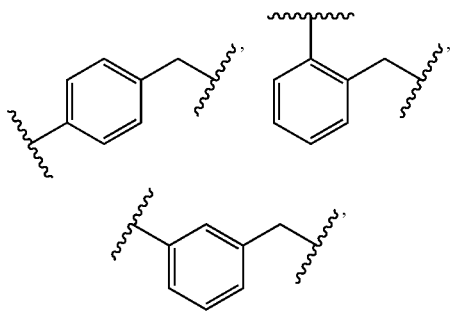

and the like.

Throughout the specification, groups and substituents thereof can be chosen by one skilled in the field to provide stable moieties and compounds.

The term "pharmaceutical agent" refers to a chemical compound or composition capable of inducing a desired therapeutic effect in a patient. In certain embodiments, a pharmaceutical agent comprises an active agent, which is the agent that induces the desired therapeutic effect. In certain embodiments, a pharmaceutical agent comprises a prodrug. In certain embodiments, a pharmaceutical agent comprises inactive ingredients such as carriers, excipients, and the like.

The term "therapeutically effective amount" refers to an amount of a pharmaceutical agent sufficient to achieve a desired therapeutic effect.

The term "pharmaceutically acceptable" refers to a formulation of a compound that does not significantly abrogate the biological activity, a pharmacological activity and/or other properties of the compound when the formulated compound is administered to a patient. In certain embodiments, a pharmaceutically acceptable formulation does not cause significant irritation to a patient.

The term "co-administer" refers to administering more than one pharmaceutical agent to a patient. In certain embodiments, co-administered pharmaceutical agents are administered together in a single dosage unit. In certain embodiments, co-administered pharmaceutical agents are administered separately. In certain embodiments, co-administered pharmaceutical agents are administered at the same time. In certain embodiments, co-administered pharmaceutical agents are administered at different times.

The term "patient" includes human and animal subjects.

The term "substantially pure" means an object species (e.g., compound) is the predominant species present (i.e., on a molar basis it is more abundant than any other individual species in the composition). In certain embodiments, a substantially purified fraction is a composition wherein the object species comprises at least about 50 percent (on a molar basis) of all species present. In certain embodiments, a substantially pure composition will comprise more than about 80%, 85%, 90%, 95%, or 99% of all species present in the composition. In certain embodiments, the object species is purified to essential homogeneity (contaminant species cannot be detected in the composition by conventional detection methods) wherein the composition consists essentially of a single species.

Certain Compounds

Certain compounds that modulate EYA tyrosine phosphatase and/or bind to EYA tyrosine phosphatase play a role in health. In certain embodiments, compounds are useful for treating diseases or conditions as provided elsewhere herein.

One of skill in the art will recognize that analogous synthesis schemes may be used to synthesize similar compounds. One of skill will recognize that compounds of the present embodiments may be synthesized using other synthesis schemes. In certain embodiments, a salt corresponding to any of the compounds provided herein is provided.

In certain embodiments, a salt corresponding to a compound as disclosed and described herein is provided. In certain embodiments, a salt is obtained by reacting a compound with an acid, such as hydrochloric acid, hydrobromic acid, sulfuric acid, nitric acid, phosphoric acid, methanesulfonic acid, ethanesulfonic acid, p-toluenesulfonic acid, salicylic acid, and the like. In certain embodiments, a salt is obtained by reacting a compound with a base to form a salt such as an ammonium salt, an alkali metal salt, such as a sodium or a potassium salt, an alkaline earth metal salt, such as a calcium or a magnesium salt, a salt of organic bases such as choline, dicyclohexylamine, N-methyl-D-glucamine, tris(hydroxymethyl)methylamine, 4-(2-hydroxyethyl)-morpholine, 1-(2-hydroxyethyl)-pyrrolidine, ethanolamine and salts with amino acids such as arginine, lysine, and the like. In certain embodiments, a salt is obtained by reacting a free acid form of a compound as disclosed and described herein with multiple molar equivalents of a base, such as bis-sodium, bis-ethanolamine, and the like.

In certain embodiments, a salt corresponding to a compound of the present embodiments is selected from acetate, ammonium, benzenesulfonate, benzoate, bicarbonate, bisulfate, bitartrate, borate, bromide, calcium edetate, camsylate, carbonate, chloride, cholinate, clavulanate, citrate, dihydrochloride, diphosphate, edetate, edisylate, estolate, esylate, fumarate, gluceptate, gluconate, glutamate, glycollylarsanilate, hexylresorcinate, hydrabanine, hydrobromide, hydrochloride, hydroxynaphthoate, iodide, isethionate, lactate, lactobionate, laurate, magnesium, malate, maleate, mandelate, mucate, napsylate, nitrate, N-methylglucamine, oxalate, pamoate (embonate), palmitate, pantothenate, phosphate, polygalacturonate, potassium, salicylate, sodium, stearate, subaceatate, succinate, sulfate, tannate, tartrate, teoclate, tosylate, triethiodide, tromethamine, trimethylammonium, and valerate salts.

Methods of Screening for EYA Tyrosine Phosphatase Inhibition

Also provided herein are methods of screening compounds for EYA tyrosine phosphatase inhibition. These methods can include methods of evaluating inhibitory properties of a compound, such as, but not limited to, a member of the set of compounds provided herein. In certain embodiments, the methods can comprise contacting EYA tyrosine phosphatase with a compound, and evaluating the level of EYA tyrosine phosphatase inhibition. In certain embodiments, the compound is a compound as disclosed herein.

The EYA tyrosine phosphatase can be from any organism that expresses EYA tyrosine phosphatases, such as those that are known in the art. In some embodiments, the EYA tyrosine phosphatase is from a mammalian organism, such as human, primate, bovine, equine, porcine, ovine, murine, canine or feline EYA tyrosine phosphatase. In some embodiments the EYA tyrosine phosphatase is from a non-mamalian organism, such as avian or zebrafish EYA tyrosine phosphatase. In typical embodiments, the EYA tyrosine phosphatase is from human or primate EYA tyrosine phosphatase. In some embodiments, the EYA tyrosine phosphatase is from a non-mammalian organism, such as zebrafish and the like. Cloning and expression of EYA tyrosine phosphatases from various organisms can be performed as described herein or as otherwise known in the art.

In some embodiments, the EYA tyrosine phosphatase is a full-length EYA tyrosine phosphatase. Thus, in some embodiments, full-length EYA tyrosine phosphatase can comprise a full-length isoform of EYA tyrosine phosphatase. The full-length EYA tyrosine phosphatase can be full-length Eya1, Eya2, Eya3, and Eya4, or an isoform thereof. As will be appreciated by those of skill in the art, a full-length EYA tyrosine phosphatase can comprise the entire encoded amino acid sequence, or can be a known isoform, such as isoform 2 of Eya 3, comprising residues 127-573 of Eya3, in Genbank accession number NM_001990. Isoforms of Eya1, Eya2 and Eya4 can be used in the methods provided herein. Thus, for example, in one embodiment, the method can comprise contacting an EYA tyrosine phosphatase with a compound, wherein the EYA tyrosine phosphatase consists of residues 127-573 of Genbank accession number NM_001990, and evaluating the level of EYA tyrosine phosphatase inhibition.

In some embodiments, the EYA tyrosine phosphatase is a truncated EYA tyrosine phosphatase. In some embodiments, the truncated EYA tyrosine phosphatase comprises one or more of N-terminal, C-terminal, or internal deletions from a full-length isoform of EYA tyrosine phosphatase. In some embodiments, the truncated EYA tyrosine phosphatase comprises a truncated Eya1, Eya2, Eya3, and Eya4, or an isoform thereof. For example, in certain embodiments, the EYA tyrosine phosphatase comprises the catalytic domain (ED) of EYA tyrosine phosphatase. As will be understood by those of skill in the art, the catalytic domain (ED) of EYA tyrosine phosphatase can be at least 80%, 85%, 90%, 91%, 92%, 93%, 94%, 95%, 96%, 97%, 98%, 99%, or 100% identical to the ED of Eya3, as can be identified by those of skill in the art. For example, the ED of Eya3 can be least 80%, 85%, 90%, 91%, 92%, 93%, 94%, 95%, 96%, 97%, 98%, 99%, or 100% identical to residues 223-510 of mouse Eya3, or to an art-understood aligned corresponding ED for Eya1, Eya2, Eya3 or Eya4. It will be appreciated by those of skill in the art that corresponding ED sequences can be found using software known in the art, for example, ClustalW.

In certain embodiments, the methods can comprise evaluating the level of EYA tyrosine phosphatase inhibition using a cell-free assay as described herein or otherwise known in the art. For example, in certain embodiments, the method comprises measuring inhibition of phosphatase activity using a p-nitrophenylphosphate (pNPP) assay as described herein or otherwise known in the art. In certain embodiments, the method comprises a peptide-based phosphatase assay as described herein or otherwise known in the art. Inhibition can be determined by whether tyrosine phosphatase activity is reduced according to a user-selected level, as described herein or otherwise known in the art. Thus, in some embodiment, a user-selected level of inhibition can be, for example, at least 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% inhibition of tyrosine phosphatase activity. In some embodiments, a user-selected level of inhibition can be an $IC_{50}$ value that is, for example, less than 10 mM, 1 mM, 100 µM, 90 µM, 80 µM, 70 µM, 60 µM, 50 µM, 40 µM, 30 µM, 20 µM, 10 µM, 1 µM, 0.1 µM, 0.01 µM, or less than 0.001 µM, as described herein or otherwise known in the art.

The results of the methods of evaluating the inhibitory properties of the compounds provided herein can be reported in terms understood in the art including, for example, $IC_{50}$, $EC_{50}$, $K_i$, or other standard terms known in the art. Thus, the evaluation methods provided herein can include evaluating the results where evaluating the results includes determining the inhibitory properties of the compound(s) being tested. In some embodiments evaluating the results also includes comparing the inhibitory properties of a compound being tested to the inhibitory properties of one or more reference compounds.

In certain embodiments, the methods can comprise an in vitro assay on whole cells as described herein or otherwise known in the art. For example, in certain embodiments, the method comprises measuring inhibition of cell migration using a cell migration assay as described herein or otherwise known in the art. In some embodiments, the method comprises measuring inhibition of tubulogenesis as described herein or otherwise known in the art. In some embodiments, the method comprises measuring inhibition of angiogenesis as described herein or otherwise known in the art.

In certain embodiments, the methods can comprise an in vivo assay as described herein or otherwise known in the art. For example, in certain embodiments, the method comprises treating an animal with a compound provided herein, and evaluating the effects of treating the animal with the compound. In certain embodiments, the method comprises using an animal model for proliferative retinopathy, retinopathy of prematurity, diabetic retinopathy, age related macular degeneration, retinal vasculitis, exudative vitreoretinopathy, tumor angiogenesis, hemangiomas or tumor metastasis. For example, in some embodiments, the method comprises measuring inhibition of vasculature formation in vivo as described herein or otherwise known in the art. For example, the method can comprise measurement of angiogenesis in zebrafish embryos as described herein or otherwise known in the art. In some embodiments, the method can comprise measurement of angiogenesis in a retinal angiogenesis model in postnatal mice as described herein or otherwise known in the art. For example, the method can comprise measurement of angiogenesis in a mouse model of oxygen-induced retinopathy as described herein or otherwise known in the art. In some embodiments, the method can comprise measurement of tumor growth. For example, the method can comprise measurement of tumor growth in a xenograft mouse model as described herein or otherwise known in the art.

Methods of Comparing Inhibition of Full-length EYA Inhibition to ED Inhibition

Also presented herein is a method for evaluating the inhibition of EYA tyrosine phosphatase comprising contacting a full-length EYA tyrosine phosphatase with a compound from a library of compounds and evaluating the results; wherein the compound has a user selected relative level of inhibitory activity compared to the inhibitory activity of the same compound when it contacts the catalytic domain (ED) of EYA tyrosine phosphatase. In some embodiments, the user-selected relative level of inhibition of full-length EYA tyrosine phosphatase at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 100%, 110%, 115%, 120%, 125%, 130%, 135%, 140%, 145%, 150%, 155%, 160%, 165%, 170%, 175%, 180%, 185%, 190%, 200%, 300%, 400% or at least 500% as much inhibitory activity as the same compound when it contacts the catalytic domain (ED) of EYA tyrosine phosphatase.

The full-length or ED form of EYA tyrosine phosphatase can be from any organism that expresses EYA tyrosine phosphatases, such as those that are known in the art. In some embodiments, the EYA tyrosine phosphatase is from a mammalian organism, such as human, primate, bovine, equine, porcine, ovine, murine, canine or feline EYA tyrosine phosphatase. In some embodiments the EYA tyrosine phosphatase is from a non-mamalian organism, such as avian or zebrafish EYA tyrosine phosphatase. In typical embodiments, the EYA tyrosine phosphatase is from human or primate EYA tyrosine phosphatase. In some embodiments, the EYA tyrosine phosphatase is from a non-mammalian organism, such as zebrafish and the like. Cloning and expression of EYA tyrosine phosphatases from various organisms can be performed as described herein or as otherwise known in the art.

The full-length EYA tyrosine phosphatase can comprise a full-length isoform of EYA tyrosine phosphatase. The full-length EYA tyrosine phosphatase can be full-length Eya1, Eya2, Eya3, and Eya4, or an isoform thereof. As will be appreciated by those of skill in the art, a full-length EYA tyrosine phosphatase can comprise the entire encoded amino acid sequence, or can be a known isoform, such as isoform 2 of Eya 3, comprising residues 127-573 of Eya3, in Genbank accession number NM_001990. Isoforms of Eya1, Eya2 and Eya4 can be used in the methods provided herein. Thus, for example, in one embodiment, the method can comprise contacting an EYA tyrosine phosphatase with a compound, wherein the EYA tyrosine phosphatase consists of residues 127-573 of Genbank accession number NM_001990, and evaluating the level of EYA tyrosine phosphatase inhibition.

As will be understood by those of skill in the art, the catalytic domain (ED) of EYA tyrosine phosphatase can be at least 80%, 85%, 90%, 91%, 92%, 93%, 94%, 95%, 96%, 97%, 98%, 99%, or 100% identical to the ED of Eya3, as can be identified by those of skill in the art. For example, the ED of Eya3 can be least 80%, 85%, 90%, 91%, 92%, 93%, 94%, 95%, 96%, 97%, 98%, 99%, or 100% identical to residues 223-510 of mouse Eya3, or to an art-understood aligned corresponding ED for Eya1, Eya2, Eya3 or Eya4. It will be appreciated by those of skill in the art that corresponding ED sequences can be found using software known in the art, for example, ClustalW.

In certain embodiments, the methods can comprise evaluating the level of EYA tyrosine phosphatase inhibition using a cell-free assay as described herein or otherwise known in the art. For example, in certain embodiments, the method comprises measuring inhibition of phosphatase activity using a p-nitrophenylphosphate (pNPP) assay as described herein or otherwise known in the art. In certain embodiments, the method comprises a peptide-based phosphatase assay as described herein or otherwise known in the art. Inhibition can be determined by whether tyrosine phosphatase activity is reduced according to a user-selected level, as described herein or otherwise known in the art. Thus, in some embodiment, a user-selected level of inhibition can be, for example, at least 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% inhibition of tyrosine phosphatase activity. In some embodiments, a user-selected level of inhibition can be an $IC_{50}$ value that is, for example, less than 10 mM, 1 mM, 100 µM, 90 µM, 80 µM, 70 µM, 60 µM, 50 µM, 40 µM, 30 µM, 20 µM, 10 µM, 1 µM, 0.1 µM, 0.01 µM, or less than 0.001 µM, as described herein or otherwise known in the art.

The results of the methods of evaluating the inhibitory properties of the compounds provided herein can be reported in terms understood in the art including, for example, $IC_{50}$, $EC_{50}$, $K_i$, or other standard terms known in the art. Thus, the evaluation methods provided herein can include evaluating the results where evaluating the results includes determining the inhibitory properties of the compound(s) being tested. In some embodiments evaluating the results also includes comparing the inhibitory properties of a compound being tested to the inhibitory properties of one or more reference compounds.

Also presented herein is a method for evaluating the inhibition of EYA tyrosine phosphatase comprising: a) contacting the catalytic domain (ED) of EYA tyrosine phosphatase with a compound from a library of compounds and evaluating the results; and b) contacting a full-length EYA tyrosine phosphatase with the compound and evaluating the results. The method can further comprise: c) performing a) for each compound in the library of compounds; d) selecting one or more compounds from c) that inhibit the catalytic domain (ED) of EYA tyrosine phosphatase according to a user-selected level; e) performing b) for each compound selected in d); and f) selecting one or more compounds from e) that inhibit full-length EYA tyrosine phosphatase according to a user-selected level.

The full-length or ED form of EYA tyrosine phosphatase can be from any organism that expresses EYA tyrosine phosphatases, such as those that are known in the art. In some embodiments, the EYA tyrosine phosphatase is from a mammalian organism, such as human, primate, bovine, equine, porcine, ovine, murine, canine or feline EYA tyrosine phosphatase. In some embodiments the EYA tyrosine phosphatase is from a non-mamalian organism, such as avian or zebrafish EYA tyrosine phosphatase. In typical embodiments, the EYA tyrosine phosphatase is from human or primate EYA tyrosine phosphatase. In some embodiments, the EYA tyrosine phosphatase is from a non-mammalian organism, such as zebrafish and the like. Cloning and expression of EYA tyrosine phosphatases from various organisms can be performed as described herein or as otherwise known in the art.

The full-length EYA tyrosine phosphatase can comprise a full-length isoform of EYA tyrosine phosphatase. The full-length EYA tyrosine phosphatase can be full-length Eya1, Eya2, Eya3, and Eya4, or an isoform thereof. As will be appreciated by those of skill in the art, a full-length EYA tyrosine phosphatase can comprise the entire encoded amino acid sequence, or can be a known isoform, such as isoform 2 of Eya 3, comprising residues 127-573 of Eya3, in Genbank accession number NM_001990. Isoforms of Eya1, Eya2 and Eya4 can be used in the methods provided herein. Thus, for example, in one embodiment, the method can comprise contacting an EYA tyrosine phosphatase with a compound, wherein the EYA tyrosine phosphatase consists of residues 127-573 of Genbank accession number NM_001990, and evaluating the level of EYA tyrosine phosphatase inhibition.

As will be understood by those of skill in the art, the catalytic domain (ED) of EYA tyrosine phosphatase can be at least 80%, 85%, 90%, 91%, 92%, 93%, 94%, 95%, 96%, 97%, 98%, 99%, or 100% identical to the ED of Eya3, as can be identified by those of skill in the art. For example, the ED of Eya3 can be least 80%, 85%, 90%, 91%, 92%, 93%, 94%, 95%, 96%, 97%, 98%, 99%, or 100% identical to residues 223-510 of mouse Eya3, or to an art-understood aligned corresponding ED for Eya1, Eya2, Eya3 or Eya4. It will be appreciated by those of skill in the art that corresponding ED sequences can be found using software known in the art, for example, ClustalW.

In certain embodiments, the methods can comprise evaluating the level of EYA tyrosine phosphatase inhibition using a cell-free assay as described herein or otherwise known in the art. For example, in certain embodiments, the method comprises measuring inhibition of phosphatase activity using a p-nitrophenylphosphate (pNPP) assay as described herein or otherwise known in the art. In certain embodiments, the method comprises a peptide-based phosphatase assay as described herein or otherwise known in the art. Inhibition can be determined by whether tyrosine phosphatase activity is reduced according to a user-selected level, as described herein or otherwise known in the art. Thus, in some embodiment, a user-selected level of inhibition can be, for example, at least 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% inhibition of tyrosine phosphatase activity. In some embodiments, a user-selected level of inhibition can be an $IC_{50}$ value that is, for example, less than 10 mM, 1 mM, 100 µM, 90 µM, 80 µM, 70 µM, 60 µM, 50 µM, 40 µM, 30 µM, 20 µM, 10 µM, 1 µM, 0.1 µM, 0.01 µM, or less than 0.001 µM, as described herein or otherwise known in the art.

The results of the methods of evaluating the inhibitory properties of the compounds provided herein can be reported in terms understood in the art including, for example, $IC_{50}$, $EC_{50}$, $K_i$, or other standard terms known in the art. Thus, the evaluation methods provided herein can include evaluating the results where evaluating the results includes determining the inhibitory properties of the compound(s) being tested. In some embodiments evaluating the results also includes comparing the inhibitory properties of a compound being tested to the inhibitory properties of one or more reference compounds.

In any of the above methods, the inhibitory activity of a compound towards full-length EYA tyrosine phosphatase can be compared to the inhibitory activity of a compound towards the catalytic domain (ED) of EYA tyrosine phosphatase. The comparison can be based on any measure of inhibition as described herein or as otherwise known in the art. For example, in some embodiments, a comparison is made based on the inhibition of full-length EYA tyrosine phosphatase versus inhibition of a the catalytic domain (ED) of EYA tyrosine phosphatase at a given concentration of a compound. The comparison can be expressed in terms as described herein or otherwise known in the art, such as percent difference or fold difference. For example, a compound at a given concentration may inhibit an full-length EYA tyrosine phosphatase with 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 100%, 110%, 115%, 120%, 125%, 130%, 135%, 140%, 145%, 150%, 155%, 160%, 165%, 170%, 175%, 180%, 185%, 190%, 200%, 300%, 400% or greater than 500% as much inhibitory activity as compared to its inhibition of catalytic domain (ED) of EYA tyrosine phosphatase at the same concentration of the compound. Likewise, a compound at a given concentration may inhibit full-length EYA tyrosine phosphatase with 0.01 fold, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, or greater than 1000 fold as much inhibitory activity as compared to its inhibition of catalytic domain (ED) of EYA tyrosine phosphatase at the same concentration of the compound. Similarly, the comparison may be made by comparing the $IC_{50}$ of a compound towards full-length EYA tyrosine phosphatase with the $IC_{50}$ of the same compound towards the catalytic domain (ED) of EYA tyrosine phosphatase. For example, a compound may inhibit full-length EYA tyrosine phosphatase with the $IC_{50}$ that is 2 fold, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or greater than 100 fold of the $IC_{50}$ of the compound towards the catalytic domain (ED) of EYA tyrosine phosphatase.

In some embodiments, the method further comprises selecting a compound based on a comparison of on the inhibition of full-length EYA tyrosine phosphatase versus inhibition of the catalytic domain (ED) of EYA tyrosine phosphatase. Typically, the compound will be selected as a specific inhibitor of an EYA tyrosine phosphatase when it exhibits inhibition of full-length EYA tyrosine phosphatase that shows greater selectivity compared to the catalytic domain (ED) of EYA tyrosine phosphatase. Thus, for example, in some embodiments, a compound may be selected as an EYA tyrosine phosphatase inhibitor if the $IC_{50}$ towards full-length EYA tyrosine phosphatase that is 2 fold, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 fold lower than the $IC_{50}$ of that compound towards the catalytic domain (ED) of EYA tyrosine phosphatase.

Methods of Comparing EYA Tyrosine Phosphatase Inhibition with Inhibition of Other Classes of Tyrosine Phosphatases.

Also presented herein is a method for identifying a compound that specifically inhibits EYA tyrosine phosphatase comprising: a) contacting EYA tyrosine phosphatase with a compound and evaluating the results; and b) contacting a cysteine catalysis-based protein tyrosine phosphatase or an FCP/SCP family protein tyrosine phosphatase with the compound and evaluating the results.

In some embodiments, the results of contacting EYA tyrosine phosphatase are compared to the results of contacting a cysteine catalysis-based protein tyrosine phosphatase with a compound. Cysteine catalysis-based protein tyrosine phosphatases are a class of protein tyrosine phosphatases as described by Alonso et al. ((2004) Cell. 117:699-711, hereby incorporated by reference in its entirety) or otherwise known in the art. While not intending to be limited to the following, it is postulated that that the EYA tyrosine phosphatase domain differs mechanistically from other protein tyrosine phosphatases such as cysteine catalysis-based protein tyrosine phosphatases, which utilize a cysteine residue in catalysis. Instead, it is postulated that the EYAs employ an aspartate as a nucleophile and another conserved aspartate two residues downstream as an acid catalyst. Thus, a comparison of EYA tyrosine phosphatase inhibition with the inhibition of a protein tyrosine phosphatase from another class can define specificity for the EYA tyrosine phosphatase active site, for example. In some embodiments, the cysteine catalysis-based protein tyrosine phosphatase is PTP1B. In some embodiments, the cysteine catalysis-based protein tyrosine phosphatase is SH-PTP1. In some embodiments, the cysteine catalysis-based protein tyrosine phosphatase is SH-PTP2. In some embodiments, the cysteine catalysis-based protein tyrosine phosphatase is another cysteine catalysis-based protein tyrosine phosphatase, as are known in the art.

In some embodiments, the results of contacting EYA tyrosine phosphatase with a compound are compared to the results of contacting a FCP/SCP family protein tyrosine phosphatase with a compound. While not intending to be limited to the following, it is postulated that that FCP/SCP family protein tyrosine phosphatases are a family of aspartate-based protein tyrosine phophatases. Thus, a comparison of EYA tyrosine phosphatase inhibition with the inhibition of a protein tyrosine phosphatase from another protein tyrosine phosphatase family can define specificity for the EYA tyrosine phosphatase active site, for example. In some embodiments, the FCP/SCP family protein tyrosine phosphatase is FCP1. In some embodiments, the FCP/SCP family protein tyrosine phosphatase is SCP.

In some embodiments, the results of contacting EYA tyrosine phosphatase are compared to the results of contacting a cysteine catalysis-based protein tyrosine phosphatase or a FCP/SCP family protein tyrosine phosphatase with a compound. The comparison can be based on any measure of inhibition as described herein or as otherwise known in the art. For example, in some embodiments, a comparison is made based on the inhibition of EYA tyrosine phosphatase versus inhibition of a cysteine catalysis-based protein tyrosine phosphatase or a FCP/SCP family protein tyrosine phosphatase at a given concentration of a compound. The comparison can be expressed in terms as described herein or otherwise known in the art, such as percent difference or fold difference. For example, a compound at a given concentration may inhibit an EYA tyrosine phosphatase with 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 100%, 110%, 115%, 120%, 125%, 130%, 135%, 140%, 145%, 150%, 155%, 160%, 165%, 170%, 175%, 180%, 185%, 190%, 200%, 300%, 400% or greater than 500% as much inhibitory activity as compared to its inhibition of a cysteine catalysis-based protein tyrosine phosphatase or a FCP/SCP family protein tyrosine phosphatase at the same concentration of the compound. Likewise, a compound at a given concentration may inhibit an EYA tyrosine phosphatase with 0.01 fold, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, or greater than 1000 fold as much inhibitory activity as compared to its inhibition of a cysteine catalysis-based protein tyrosine phosphatase or a FCP/SCP family protein tyrosine phosphatase at the same concentration of the compound. Similarly, the comparison may be made by comparing the $IC_{50}$ of a compound towards an EYA tyrosine phosphatase with the $IC_{50}$ of the same compound towards a cysteine catalysis-based protein tyrosine phosphatase or a FCP/SCP family protein tyrosine phosphatase. For example, a compound may inhibit an EYA tyrosine phosphatase with the $IC_{50}$ that is 2 fold, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or greater than 100 fold of the $IC_{50}$ of the compound towards a cysteine catalysis-based protein tyrosine phosphatase or a FCP/SCP family protein tyrosine phosphatase. In some embodiments, the inhibition of EYA tyrosine phosphatase is tested first, followed by testing the inhibition of a cysteine catalysis-based protein tyrosine phosphatase or a FCP/SCP family protein tyrosine phosphatase.

In some embodiments, the method further comprises selecting a compound based on a comparison of on the inhibition of EYA tyrosine phosphatase versus inhibition of a cysteine catalysis-based protein tyrosine phosphatase or a FCP/SCP family protein tyrosine phosphatase. Typically, the compound will be selected as a specific inhibitor of an EYA tyrosine phosphatase when it exhibits inhibition of EYA tyrosine phosphatase that shows greater selectivity compared to another class or family of protein tyrosine phosphatases. Thus, for example, in some embodiments, a compound may be selected as an EYA tyrosine phosphatase inhibitor if the $IC_{50}$ towards EYA tyrosine phosphatase that is 2 fold, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 fold lower than the $IC_{50}$ of that compound towards a cysteine catalysis-based protein tyrosine phosphatase or a FCP/SCP family protein tyrosine phosphatase. An example of such a comparison and selection is set forth in Table 1 in Examples below.

Methods of Screening for Inhibition of Disease States.

Also presented herein is a method of evaluating a compound for inhibition of cell migration, proliferative retinopathy, retinopathy of prematurity, diabetic retinopathy, age related macular degeneration, retinal vasculitis, exudative vitreoretinopathy, tumor angiogenesis, hemangiomas or tumor metastasis, comprising contacting an EYA tyrosine phosphatase with a compound and evaluating the results. In some embodiments, the compound comprises a compound as disclosed herein.

Also presented herein is a method of evaluating a compound for inhibition of breast cancer (including ductal carcinoma lobule carcinoma and breast epithelial cancer), ovarian cancer (including epithelial ovarian cancer), desmoid tumor, malignant peripheral nerve sheath cancer, acute leukemia, rhabdomyosarcoma, Ewing's sarcoma, extra-skeletal myxoid chondrosarcoma, or endometrial cancer, comprising contacting an EYA tyrosine phosphatase with a compound and evaluating the results. In some embodiments, the compound comprises a compound as disclosed herein.

Also presented herein is a method of evaluating a compound for inhibition of Wilms' tumor, esophageal adenocarcinoma, colon cancer, colorectal cancer, esophageal squamous cell carcinoma, lung adenocarcinoma, Epstein-Barr virus-negative gastric cancer, or pancreatic ductal adenocarcinoma, comprising contacting an EYA tyrosine phosphatase with a compound and evaluating the results. In some embodiments, the compound comprises a compound as disclosed herein.

In some embodiments, the results are evaluated by determining the level of inhibition of an EYA protein or truncated version thereof, relative to no inhibitor or relative to a control. In some embodiments, the results are evaluated by determining the level of inhibition of a full-length EYA protein or relative to a truncated EYA protein. In some embodiments, the results are evaluated by determining the level of reduction in pathological neovascularization relative to no inhibitor or relative to a control. In some embodiments, the results are evaluated by determining the level of reduction in angiogenesis relative to no inhibitor or relative to a control. In some embodiments, the results are evaluated by determining the level of reduction in metastasis to no inhibitor or relative to a control. In some embodiments, the results are evaluated by determining the level of reduction in tumor size relative to no inhibitor or relative to a control.

In some embodiments, the method comprises evaluating the level of inhibition of full-length EYA tyrosine phosphatase in comparison with the level of inhibition of a truncated EYA tyrosine phosphatase. The full-length or truncated form of EYA tyrosine phosphatase can be from any organism that expresses EYA tyrosine phosphatases, such as those that are known in the art. In some embodiments, the EYA tyrosine phosphatase is from a mammalian organism, such as human, primate, bovine, equine, porcine, ovine, murine, canine or feline EYA tyrosine phosphatase. In some embodiments the EYA tyrosine phosphatase is from a non-mamalian organism, such as avian or zebrafish EYA tyrosine phosphatase. In typical embodiments, the EYA tyrosine phosphatase is from human or primate EYA tyrosine phosphatase. In some embodiments, the EYA tyrosine phosphatase is from a non-mammalian organism, such as zebrafish and the like. Cloning and expression of EYA tyrosine phosphatases from various organisms can be performed as described herein or as otherwise known in the art.

The full-length EYA tyrosine phosphatase can comprise a full-length isoform of EYA tyrosine phosphatase. The full-length EYA tyrosine phosphatase can be full-length Eya1, Eya2, Eya3, and Eya4, or an isoform thereof. As will be appreciated by those of skill in the art, a full-length EYA tyrosine phosphatase can comprise the entire encoded amino acid sequence, or can be a known isoform, such as isoform 2 of Eya 3, comprising residues 127-573 of Eya3, in Genbank accession number NM_001990. Isoforms of Eya1, Eya2 and Eya4 can be used in the methods provided herein. Thus, for example, in one embodiment, the method can comprise contacting an EYA tyrosine phosphatase with a compound, wherein the EYA tyrosine phosphatase consists of residues 127-573 of Genbank accession number NM_001990, and evaluating the level of EYA tyrosine phosphatase inhibition.

In some embodiments, the truncated EYA tyrosine phosphatase comprises one or more of N-terminal, C-terminal, or internal deletions from a full-length isoform of EYA tyrosine phosphatase. In some embodiments, the truncated EYA tyrosine phosphatase comprises a truncated Eya1, Eya2, Eya3, and Eya4, or an isoform thereof. For example, in certain embodiments, the EYA tyrosine phosphatase comprises the catalytic domain (ED) of EYA tyrosine phosphatase. As will be understood by those of skill in the art, the catalytic domain (ED) of EYA tyrosine phosphatase can be at least 80%, 85%, 90%, 91%, 92%, 93%, 94%, 95%, 96%, 97%, 98%, 99%, or 100% identical to the ED of Eya3, as can be identified by those of skill in the art. For example, the ED of Eya3 can be least 80%, 85%, 90%, 91%, 92%, 93%, 94%, 95%, 96%, 97%, 98%, 99%, or 100% identical to residues 223-510 of mouse Eya3, or to an art-understood aligned corresponding ED for Eya1, Eya2, Eya3 or Eya4. It will be appreciated by those of skill in the art that corresponding ED sequences can be found using software known in the art, for example, ClustalW.

In certain embodiments, the methods can comprise evaluating the level of EYA tyrosine phosphatase inhibition using a cell-free assay as described herein or otherwise known in the art. For example, in certain embodiments, the method comprises measuring inhibition of phosphatase activity using a p-nitrophenylphosphate (pNPP) assay as described herein or otherwise known in the art. In certain embodiments, the method comprises a peptide-based phosphatase assay as described herein or otherwise known in the art. Inhibition can be determined by whether tyrosine phosphatase activity is reduced according to a user-selected level, as described herein or otherwise known in the art. Thus, in some embodiment, a user-selected level of inhibition can be, for example, at least 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% inhibition of tyrosine phosphatase activity. In some embodiments, a user-selected level of inhibition can be an $IC_{50}$ value that is, for example, less than 10 mM, 1 mM, 100 µM, 90 µM, 80 µM, 70 µM, 60 µM, 50 µM, 40 µM, 30 µM, 20 µM, 10 µM, 1 µM, 0.1 µM, 0.01 µM, or less than 0.001 µM, as described herein or otherwise known in the art.

The results of the methods of evaluating the inhibitory properties of the compounds provided herein can be reported in terms understood in the art including, for example, $IC_{50}$, $EC_{50}$, $K_i$, or other standard terms known in the art. Thus, the evaluation methods provided herein can include evaluating the results where evaluating the results includes determining the inhibitory properties of the compound(s) being tested. In some embodiments evaluating the results also includes comparing the inhibitory properties of a compound being tested to the inhibitory properties of one or more reference compounds.

In some embodiments, the method comprises evaluating the level of inhibition of EYA tyrosine phosphatase in comparison with the level of inhibition of a cysteine catalysis-based protein tyrosine phosphatase or an FCP/SCP family protein tyrosine phosphatase. In some embodiments, the cysteine catalysis-based protein tyrosine phosphatase is PTP1B. In some embodiments, the cysteine catalysis-based protein tyrosine phosphatase is SH-PTP1. In some embodiments, the cysteine catalysis-based protein tyrosine phosphatase is SH-PTP2. In some embodiments, the cysteine catalysis-based protein tyrosine phosphatase is another cysteine catalysis-based protein tyrosine phosphatase, as are known in the art. In some embodiments, the results of contacting EYA tyrosine phosphatase with a compound are compared to the results of contacting a FCP/SCP family protein tyrosine phosphatase with a compound. As is known in the art, FCP/SCP family protein tyrosine phosphatases are a family of aspartate-based protein tyrosine phophatases. Thus, a comparison of EYA tyrosine phosphatase inhibition with the inhibition of a protein tyrosine phosphatase from another protein tyrosine phosphatase family can define specificity for the EYA tyrosine phosphatase active site, for example. In some embodiments, the FCP/SCP family protein tyrosine phosphatase is FCP1. In some embodiments, the FCP/SCP family protein tyrosine phosphatase is SCP.

Certain Pharmaceutical Agents

In certain embodiments, at least one compound as disclosed and described herein, or pharmaceutically acceptable salt, ester, amide, and/or prodrug thereof, either alone or combined with one or more pharmaceutically acceptable carriers, forms a pharmaceutical agent. Techniques for formulation and administration of compounds of the present embodiments may be found for example, in "Remington's Pharmaceutical Sciences," Mack Publishing Co., Easton, Pa., 18th edition, 1990, which is incorporated herein by reference in its entirety.

In certain embodiments, a pharmaceutical agent comprising one or more compounds of the present embodiments is prepared using known techniques, including, but not limited to mixing, dissolving, granulating, dragee-making, levigating, emulsifying, encapsulating, entrapping or tabletting processes.

In certain embodiments, a pharmaceutical agent comprising one or more compounds of the present embodiments is a liquid (e.g., a suspension, elixir and/or solution). In certain of such embodiments, a liquid pharmaceutical agent comprising one or more compounds of the present embodiments is prepared using ingredients known in the art, including, but not limited to, water, glycols, oils, alcohols, flavoring agents, preservatives, and coloring agents.

In certain embodiments, a pharmaceutical agent comprising one or more compounds of the present embodiments is a solid (e.g., a powder, tablet, and/or capsule). In certain of such embodiments, a solid pharmaceutical agent comprising one or more compounds of the present embodiments is prepared using ingredients known in the art, including, but not limited to, starches, sugars, diluents, granulating agents, lubricants, binders, and disintegrating agents.

In certain embodiments, a pharmaceutical agent comprising one or more compounds of the present embodiments is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical agent comprising one or more compounds of the present embodiments comprises a delivery system. Examples of delivery systems include, but are not limited to, liposomes and emulsions. Certain delivery systems are useful for preparing certain pharmaceutical agents including those comprising hydrophobic compounds. In certain embodiments, certain organic solvents such as dimethylsulfoxide are used.

In certain embodiments, a pharmaceutical agent comprising one or more compounds of the present embodiments comprises one or more tissue-specific delivery molecules designed to deliver the pharmaceutical agent to specific tissues or cell types. For example, in certain embodiments, pharmaceutical agents include liposomes coated with a tissue-specific antibody.

In certain embodiments, a pharmaceutical agent comprising one or more compounds of the present embodiments comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate80™, and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical agent comprising one or more compounds of the present embodiments comprises a sustained-release system. A non-limiting example of such a sustained-release system is a semipermeable matrix of solid hydrophobic polymers. In certain embodiments, sustained-release systems may, depending on their chemical nature, release compounds over a period of hours, days, weeks or months.

Certain compounds used in pharmaceutical agent of the present embodiments may be provided as pharmaceutically acceptable salts with pharmaceutically compatible counterions. Pharmaceutically compatible salts may be formed with many acids, including but not limited to hydrochloric, sulfuric, acetic, lactic, tartaric, malic, succinic, etc.

In certain embodiments, a pharmaceutical agent comprising one or more compounds of the present embodiments comprises an active ingredient in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, a pharmaceutical agent comprising one or more compounds of the present embodiments is useful for treating a conditions or disorder in a mammalian, and particularly in a human patient. Suitable administration routes include, but are not limited to, oral, rectal, transmucosal, intestinal, enteral, topical, suppository, through inhalation, intrathecal, intraventricular, intraperitoneal, intranasal, intraocular and parenteral (e.g., intravenous, intramuscular, intramedullary, and subcutaneous). In certain embodiments, pharmaceutical intrathecals are administered to achieve local rather than systemic exposures. For example, pharmaceutical agents may be injected directly in the area of desired effect (e.g., in the renal or cardiac area).

In certain embodiments, a pharmaceutical agent comprising one or more compounds of the present embodiments is administered in the form of a dosage unit (e.g., tablet, capsule, bolus, etc.). In certain embodiments, such dosage units comprise a compound as disclosed and described herein in a dose from about 1 µg/kg of body weight to about 50 mg/kg of body weight. In certain embodiments, such dosage units comprise a compound as disclosed and described herein in a dose from about 2 µg/kg of body weight to about 25 mg/kg of body weight. In certain embodiments, such dosage units comprise a compound as disclosed and described herein in a dose from about 10 µg/kg of body weight to about 5 mg/kg of body weight. In certain embodiments, pharmaceutical agents are administered as needed, once per day, twice per day, three times per day, or four or more times per day. It is recognized by those skilled in the art that the particular dose, frequency, and duration of administration depends on a number of factors, including, without limitation, the biological activity desired, the condition of the patient, and tolerance for the pharmaceutical agent.

In certain embodiments, a pharmaceutical agent comprising a compound of the present embodiments is prepared for oral administration. In certain of such embodiments, a pharmaceutical agent is formulated by combining one or more compounds of the present embodiments with one or more pharmaceutically acceptable carriers. Certain of such carriers enable compounds of the present embodiments to be formulated as tablets, pills, dragees, capsules, liquids, gels, syrups, slurries, suspensions and the like, for oral ingestion by a patient. In certain embodiments, pharmaceutical agents for oral use are obtained by mixing one or more compounds of the present embodiments and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical agents are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain of such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical agents for oral administration are push-fit capsules made of gelatin. Certain of such push-fit capsules comprise one or more compounds of the present embodiments in admixture with one or more filler such as lactose, binders such as starches, and/or lubricants such as talc or magnesium stearate and, optionally, stabilizers. In certain embodiments, pharmaceutical agents for oral administration are soft, sealed capsules made of gelatin and a plasticizer, such as glycerol or sorbitol. In certain soft capsules, one or more compounds of the present embodiments are be dissolved or suspended in suitable liquids, such as fatty oils, liquid paraffin, or liquid polyethylene glycols. In addition, stabilizers may be added.

In certain embodiments, pharmaceutical agents are prepared for buccal administration. Certain of such pharmaceutical agents are tablets or lozenges formulated in conventional manner.

In certain embodiments, a pharmaceutical agent is prepared for administration by injection (e.g., intravenous, subcutaneous, intramuscular, etc.). In certain of such embodiments, a pharmaceutical agent comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical agents for injection are presented in unit dosage form, e.g., in ampoules or in multidose containers. Certain pharmaceutical agents for injection are suspensions, solutions or emulsions in oily or aqueous vehicles, and may contain formulatory agents such as suspending, stabilizing and/or dispersing agents. Certain solvents suitable for use in pharmaceutical agents for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the compounds to allow for the preparation of highly concentrated solutions.

In certain embodiments, a pharmaceutical agent is prepared for transmucosal administration. In certain of such embodiments penetrants appropriate to the barrier to be permeated are used in the formulation. Such penetrants are generally known in the art.

In certain embodiments, a pharmaceutical agent is prepared for administration by inhalation. Certain of such pharmaceutical agents for inhalation are prepared in the form of an aerosol spray in a pressurized pack or a nebulizer. Certain of such pharmaceutical agents comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a compound of the present embodiments and a suitable powder base such as lactose or starch.

In certain embodiments, a pharmaceutical agent is prepared for rectal administration, such as a suppositories or retention enema. Certain of such pharmaceutical agents comprise known ingredients, such as cocoa butter and/or other glycerides.

In certain embodiments, a pharmaceutical agent is prepared for topical administration. Certain of such pharmaceutical agents comprise bland moisturizing bases, such as ointments or creams. Exemplary suitable ointment bases include, but are not limited to, petrolatum, petrolatum plus volatile silicones, lanolin and water in oil emulsions such as Eucerin™, available from Beiersdorf (Cincinnati, Ohio). Exemplary suitable cream bases include, but are not limited to, Nivea™ Cream, available from Beiersdorf (Cincinnati, Ohio), cold cream (USP), Purpose Cream™, available from Johnson & Johnson (New Brunswick, N.J.), hydrophilic ointment (USP) and Lubriderm™, available from Pfizer (Morris Plains, N.J.).

In certain embodiments, the formulation, route of administration and dosage for a pharmaceutical agent of the present embodiments can be chosen in view of a particular patient's condition. (See e.g., Fingl et al. 1975, in "The Pharmacological Basis of Therapeutics", Ch. 1 p. 1, which is incorporated herein by reference in its entirety). In certain embodiments, a pharmaceutical agent is administered as a single dose. In certain embodiments, a pharmaceutical agent is administered as a series of two or more doses administered over one or more days.

In certain embodiments, a pharmaceutical agent of the present embodiments is administered to a patient between about 0.1% and 500%, 5% and 200%, 10% and 100%, 15% and 85%, 25% and 75%, or 40% and 60% of an established human dosage. Where no human dosage is established, a suitable human dosage may be inferred from $ED_{50}$ or $ID_{50}$ values, or other appropriate values derived from in vitro or in vivo studies.

In certain embodiments, a daily dosage regimen for a patient comprises an oral dose of between 0.1 mg and 2000 mg, 5 mg and 1500 mg, 10 mg and 1000 mg, 20 mg and 500 mg, 30 mg and 200 mg, or 40 mg and 100 mg of a compound of the present embodiments. In certain embodiments, a daily dosage regimen is administered as a single daily dose. In certain embodiments, a daily dosage regimen is administered as two, three, four, or more than four doses.

In certain embodiments, a pharmaceutical agent of the present embodiments is administered by continuous intravenous infusion. In certain of such embodiments, from 0.1 mg to 500 mg of a composition of the present embodiments is administered per day.

In certain embodiments, a pharmaceutical agent of the present embodiments is administered for a period of continuous therapy. For example, a pharmaceutical agent of the present embodiments may be administered over a period of days, weeks, months, or years.

Dosage amount, interval between doses, and duration of treatment may be adjusted to achieve a desired effect. In certain embodiments, dosage amount and interval between doses are adjusted to maintain a desired concentration on compound in a patient. For example, in certain embodiments, dosage amount and interval between doses are adjusted to provide plasma concentration of a compound of the present embodiments at an amount sufficient to achieve a desired effect. In certain of such embodiments the plasma concentration is maintained above the minimal effective concentration (MEC). In certain embodiments, pharmaceutical agents of the present embodiments are administered with a dosage regimen designed to maintain a concentration above the MEC for 10-90% of the time, between 30-90% of the time, or between 50-90% of the time.

In certain embodiments in which a pharmaceutical agent is administered locally, the dosage regimen is adjusted to achieve a desired local concentration of a compound of the present embodiments.

In certain embodiments, a pharmaceutical agent may be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the present embodiments formulated in a compatible pharmaceutical carrier may also be prepared, placed in an appropriate container, and labeled for treatment of an indicated condition.

In certain embodiments, a pharmaceutical agent is in powder form for constitution with a suitable vehicle, e.g., sterile pyrogen-free water, before use.

Methods of Treatment

Based on the teachings provided herein, the compounds provided herein can be used in methods of treating or relieving the symptoms of diseases such as neutrophil infiltration, hemorrhagic shock, inflammatory bowel disease, or lung inflammation. In many embodiments, the compounds as described herein can be administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. The EYA tyrosine phosphatase inhibitor compounds as described herein can be administered 5 times per day, 4 times per day, 3 times per day or 2 times per day. In other embodiments, the EYA tyrosine phosphatase inhibitor compound is administered as a continuous infusion.

In many embodiments, an compounds as described herein of the embodiments can be administered orally.

In connection with the above-described methods for the treatment of neutrophil infiltration, hemorrhagic shock, inflammatory bowel disease, or lung inflammation in a patient, a compound as described herein may be administered to the patient at a dosage from about 0.01 mg to about 100 mg/kg patient bodyweight per day, in 1 to 5 divided doses per day. In some embodiments, the compounds as described herein can be administered at a dosage of about 0.5 mg to about 75 mg/kg patient bodyweight per day, in 1 to 5 divided doses per day.

In some embodiments, based on the teachings provided herein, the compounds provided herein can be used in methods of treating or relieving the symptoms of diseases such as proliferative retinopathy, retinopathy of prematurity, diabetic retinopathy, age related macular degeneration, retinal vasculitis, exudative vitreoretinopathy, tumor angiogenesis, hemangiomas or tumor metastasis. In many embodiments, the compounds as described herein can be administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. The EYA tyrosine phosphatase inhibitor compounds as described herein can be administered 5 times per day, 4 times per day, 3 times per day or 2 times per day. In other embodiments, the EYA tyrosine phosphatase inhibitor compound is administered as a continuous infusion.

In many embodiments, an compounds as described herein of the embodiments can be administered orally.

In connection with the above-described methods for the treatment of proliferative retinopathy, retinopathy of prematurity, diabetic retinopathy, age related macular degeneration, retinal vasculitis, exudative vitreoretinopathy, tumor angiogenesis, hemangiomas or tumor metastasis in a patient, a compound as described herein may be administered to the patient at a dosage from about 0.01 mg to about 100 mg/kg patient bodyweight per day, in 1 to 5 divided doses per day. In some embodiments, the compounds as described herein can be administered at a dosage of about 0.5 mg to about 75 mg/kg patient bodyweight per day, in 1 to 5 divided doses per day.

In some embodiments, based on the teachings provided herein, the compounds provided herein can be used in methods of treating or relieving the symptoms of diseases such as breast cancer (including ductal carcinoma lobule carcinoma and breast epithelial cancer), ovarian cancer (including epithelial ovarian cancer), desmoid tumor, malignant peripheral nerve sheath cancer, acute leukemia, rhabdomyosarcoma, Ewing's sarcoma, extra-skeletal myxoid chondrosarcoma, or endometrial cancer. In many embodiments, the compounds as described herein can be administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. The EYA tyrosine phosphatase inhibitor compounds as described herein can be administered 5 times per day, 4 times per day, 3 times per day or 2 times per day. In other embodiments, the EYA tyrosine phosphatase inhibitor compound is administered as a continuous infusion.

In many embodiments, an compounds as described herein of the embodiments can be administered orally.

In connection with the above-described methods for the treatment of breast cancer (including ductal carcinoma lobule carcinoma and breast epithelial cancer), ovarian cancer (including epithelial ovarian cancer), desmoid tumor, malignant peripheral nerve sheath cancer, acute leukemia, rhabdomyosarcoma, Ewing's sarcoma, extra-skeletal myxoid chondrosarcoma, or endometrial cancer in a patient, a compound as described herein may be administered to the patient at a dosage from about 0.01 mg to about 100 mg/kg patient bodyweight per day, in 1 to 5 divided doses per day. In some embodiments, the compounds as described herein can be administered at a dosage of about 0.5 mg to about 75 mg/kg patient bodyweight per day, in 1 to 5 divided doses per day.

In some embodiments, based on the teachings provided herein, the compounds provided herein can be used in methods of treating or relieving the symptoms of diseases such as Wilms' tumor, esophageal adenocarcinoma, colon cancer, colorectal cancer, esophageal squamous cell carcinoma, lung adenocarcinoma, Epstein-Barr virus-negative gastric cancer, or pancreatic ductal adenocarcinoma. In many embodiments, the compounds as described herein can be administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. The EYA tyrosine phosphatase inhibitor compounds as described herein can be administered 5 times per day, 4 times per day, 3 times per day or 2 times per day. In other embodiments, the EYA tyrosine phosphatase inhibitor compound is administered as a continuous infusion.

In many embodiments, an compounds as described herein of the embodiments can be administered orally.

In connection with the above-described methods for the treatment of Wilms' tumor, esophageal adenocarcinoma, colon cancer, colorectal cancer, esophageal squamous cell carcinoma, lung adenocarcinoma, Epstein-Barr virus-negative gastric cancer, or pancreatic ductal adenocarcinoma in a patient, a compound as described herein may be administered to the patient at a dosage from about 0.01 mg to about 100 mg/kg patient bodyweight per day, in 1 to 5 divided doses per day. In some embodiments, the compounds as described herein can be administered at a dosage of about 0.5 mg to about 75 mg/kg patient bodyweight per day, in 1 to 5 divided doses per day.

The amount of active ingredient that may be combined with carrier materials to produce a dosage form can vary depending on the host to be treated and the particular mode of administration. A typical pharmaceutical preparation can contain from about 5% to about 95% active ingredient (w/w). In other embodiments, the pharmaceutical preparation can contain from about 20% to about 80% active ingredient.

Those of skill will readily appreciate that dose levels can vary as a function of the specific compound, the severity of the symptoms and the susceptibility of the subject to side effects. Preferred dosages for a given compound as described herein can be readily determinable by those of skill in the art by a variety of means.

In certain embodiments, multiple doses of EYA tyrosine phosphatase inhibitor compound are administered. For example, an EYA tyrosine phosphatase inhibitor compound is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid), over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

EXAMPLES

The following examples are set forth merely to assist in understanding the embodiments and should not be construed as limiting the embodiments described and claimed herein in any way. Variations of the invention, including the substitution of all equivalents now known or later developed, which would be within the purview of those skilled in the art, and changes in formulation or minor changes in experimental design, are to be considered to fall within the scope of the embodiments incorporated herein.

The compounds of Formulae I, II, III and IV can be prepared according to methods known in the art. For example, the compounds of Formulae I, II, III and IV can be prepared according to the general method shown in Scheme 1 using the appropriate chemical reagents to obtain the desired compounds.

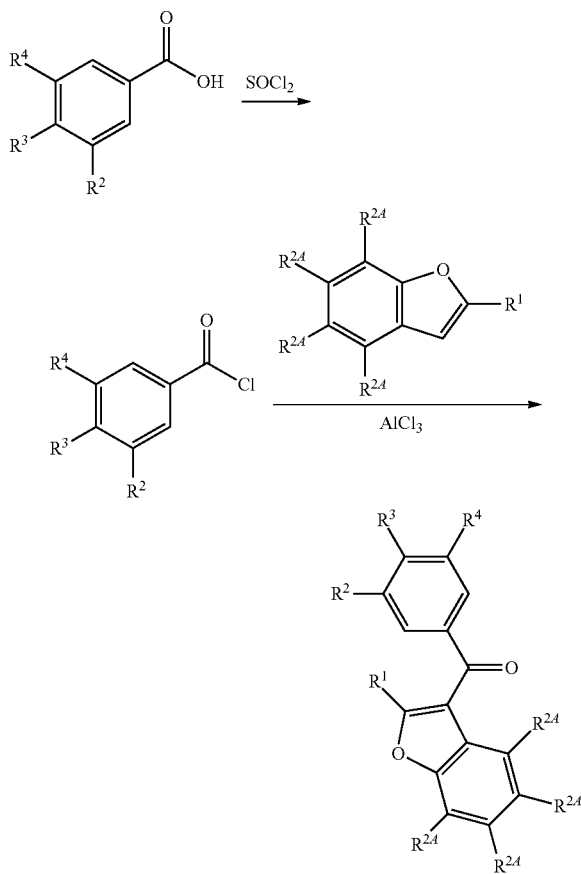

$R^1$-$R^4$, and $R^{2A}$ may be defined as disclosed for the compounds of Formulae I, II, III and IV described herein with appropriate selection in view of the synthetic protocol.

Examples of reaction conditions and specific synthetic procedures for the preparation of compounds of Formulae I, II, III and IV can be found in the methods described in Hu et al., "A Convergent Synthetic Study of Biologically Active Benzofuran Derivatives," *Arch Pharm Res*, 2006, 29(6): 476-478 and McDonald et al., "Warfarin-Amiodarone Drug-Drug Interactions: Determination of $[I]_u/K_{I,u}$ for Amiodarone and Its Plasma Metabolites," *Clin Pharmacol Ther*, 2012, 91(4): 709-717 modified using the appropriate chemical reagents to obtain the desired compounds.

Example 1

Inhibition of Eya 3 Catalytic Activity

The following experiments were performed to evaluate the inhibition of Eya3 catalytic activity.

Purification of Recombinant Proteins. The catalytic domain of mouse Eya3 ("ED", comprising residues 223-510 of Eya3) was purified as described by Rayapureddi, J. P. et al. (*FEBS Lett* 580, 3853-3859 (2006), incorporated by reference in its entirety). For full-length Eya3 ("hEYA3"), human Eya3 isoform 2 (representing the major species identified in human cell lines by mass spectrometry, expressed as residues 127-573 of NM_001990, isoform 1) was sub-cloned into pDEST565 to express a poly-histidine-Glutathione-S-transferase (His-GST) tagged fusion protein with a TVMV protease site. The protein was purified by glutathione-S-transferase affinity chromatography followed by TVMV cleavage, Ni-NTA chromatography, and finally size exclusion chromatography.

The catalytic domain of human Eya2 ("hEYA2(ED)") was similarly sub-cloned as a polyhistidine fusion construct in the vector pDEST-527. Fusion protein was purified by NiNTA chromatography and followed by size-exclusion chromatography over a Superdex-75 column. The relative purity of protein samples was determined using SDS-PAGE. PTP1B was purified as described previously (Rayapureddi, J. P. et al. *Nature* 426, 295-298 (2003), incorporated by reference in its entirety).

Screening Methods. An inhibitory assay was conducted using the previously described p-nitrophenylphosphate assay (Rayapureddi, J. P. et al. *Nature* 426, 295-298 (2003)). Briefly, ED was incubated in a reaction mixture containing 20 mM MES pH 6, 2 mM $MgCl_2$, 125 µM inhibitor, 3.4 mM para-nitrophenol phosphate (pNPP) and 0.01 µg/L enzyme. The amount of 4-nitrophenol (pNP) produced was monitored at 405 nM on a BioTek EL808 plate reader. A similar protocol was used to screen for inhibitor activity using hEYA3 and hEYA2(ED).

The compounds were then tested using full-length human recombinant, purified EYA3 and pNPP as a substrate. Compounds were dissolved in DMSO and diluted as needed. $IC_{50}$ values were determined by adding varying amounts of inhibitor (0-400 µM) to reaction mixtures containing 20 mM MES pH 6, 2 mM $MgCl_2$, 2% DMSO, 3.4 mM pNPP, and 0.01 µg/L enzyme. Reactions were incubated at 30° C. for 30 minutes and quenched with 100 mM EDTA pH 10. $IC_{50}$ values were then calculated directly from regression curves using PRISM software. All reported values are the mean of two independent experiments.

These results were mirrored when an alternate substrate, a 10 amino acid phosphopeptide representing the C-terminus of the known EYA substrate γ-H2AX (Cook, P. J. et al. *Nature* 458, 591-596, (2009); Krishnan, N. et al. *J. Biol. Chem.* (2009), the contents of which are incorporated by reference in their entireties). The phospho-peptide KKATQASQEpY (SEQ. ID 5) was obtained from Genscript. Peptide assays were conducted in 20 mM MES pH 6, 2 mM $MgCl_2$, and a range of peptide concentrations from 0 to 300 µM as previously described in the incorporated materials of Rayapureddi, J. P. (2003). $IC_{50}$ values were then calculated using PRISM software.

The compounds of Table 1 were examined for their ability to inhibit the catalytic activity of Eya3(ED) and full-length EYA3. The compounds listed in Table 1 can be prepared according to methods know in the art. For example, the following compounds listed in Table 1 can be prepared according to the method described in Hu et al., "A Convergent Synthetic Study of Biologically Active Benzofuran Derivatives," *Arch Pharm Res,* 2006, 29(6): 476-478 and McDonald et al., "Warfarin-Amiodarone Drug-Drug Interactions: Determination of $[I]_u/K_{I,u}$ for Amiodarone and Its Plasma Metabolites," *Clin Pharmacol Ther,* 2012, 91(4): 709-717 modified using the appropriate chemical reagents to obtain the desired compounds. Compound 1a was obtained from Sigma-Aldrich (cat. no. L129305) and compound 1b from ChemDiv (cat. no. 3039-0682).

Compounds 1a and 1b, which retain the basic scaffold of a phenol and a benzofuran linked by a carbonyl group, had $IC_{50}$ values comparable to those of compound 1. Deletion of the two bromine atoms or increasing the length of the aliphatic substituent on the benzofuran did not significantly affect the inhibition.

Exemplary results are set forth in FIG. 1a. The inhibitory effect was retained in the presence of 0.01% Triton X-100, a non-ionic detergent, indicating that compound 1 was not non-specifically self-aggregating and sequestering enzyme as has been observed with other known drugs.

Figure 1B:
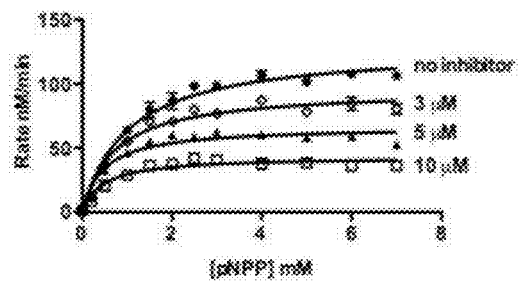
Figure 1C:
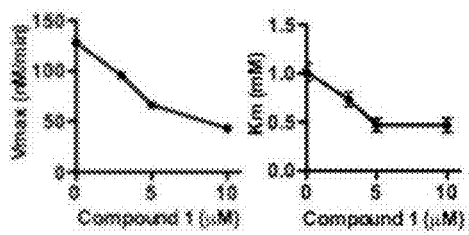

As shown in FIG. 1b, substrate titration shows that compound 1 is not a competitive inhibitor of EYA3. Increasing concentration of substrate does not overcome inhibition. Each point represents the mean and standard deviation of two independent readings. As shown in FIG. 1c, plots of Vmax and Km as a function of inhibitor concentration show that both values decrease with increased inhibitor concentration. Values for Vmax and Km were derived from non-linear regression analyses of curves in FIG. 1b using PRISM (GraphPad Software).

Figure 1D:
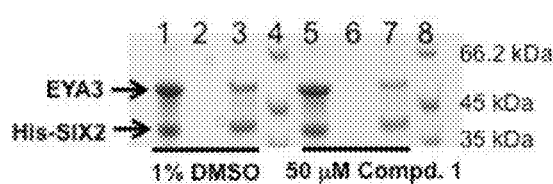

One function of the catalytic domain of the EYAs is to mediate its interaction with the SIX proteins. This complex then translocates to the nucleus where the SIX-EYA complex can activate transcription. To determine whether this series of compounds might disrupt a representative EYA-SIX interaction, tests were performed to determine the ability of His-tagged SIX2 to pull down EYA3 in the presence and absence of compound 1, using Ni-NTA agarose. The interaction appeared to be unaffected by the presence of the EYA inhibitor (FIG. 1d).

These results demonstrate that compound 1 specifically inhibits the phosphatase activity of Eya3.

A summary of the results is shown in Table 1.

TABLE 1

| Compound | Structure | IC50 (pNPP) | | |
|---|---|---|---|---|
| | | Eya3(ED) | EYA3 | PTP1B |
| 1 | 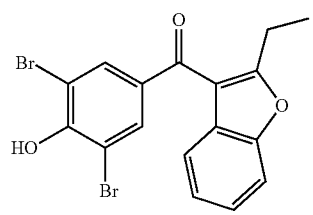 [SMILES: CCc1oc2ccccc2c1C(=O)c1cc(Br)c(O)c(Br)c1] | 11 | 8.3 | 53.8 |
| 1a | 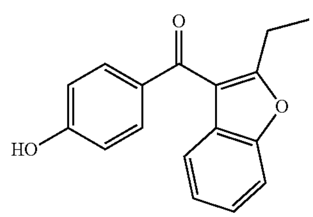 [SMILES: CCc1oc2ccccc2c1C(=O)c1ccc(O)cc1] | 19.2 | 17.0 | >150 |
| 1b | 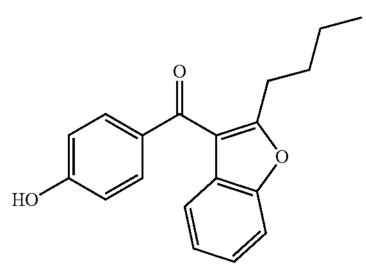 [SMILES: CCCCc1oc2ccccc2c1C(=O)c1ccc(O)cc1] | 10.1 | 15.2 | 71.4 |
| 1c | 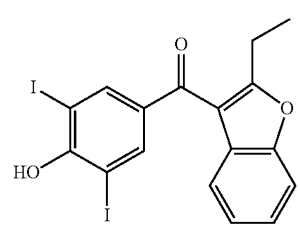 [SMILES: CCc1oc2ccccc2c1C(=O)c1cc(I)c(O)c(I)c1] | | | 3.4 |

TABLE 1-continued

| Compound | Structure | IC50 (pNPP) Eya3(ED) | EYA3 | PTP1B |
|---|---|---|---|---|
| 1d | 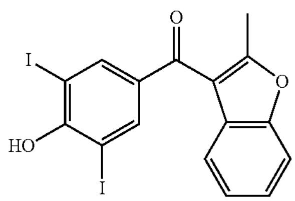 [SMILES: Cc1oc2ccccc2c1C(=O)c1cc(I)c(O)c(I)c1] | 8.3 | | |
| 1e | 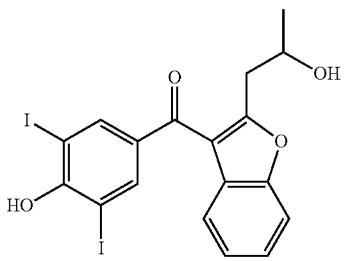 [SMILES: CC(O)Cc1oc2ccccc2c1C(=O)c1cc(I)c(O)c(I)c1] | 13.8 | | |
| 1f | 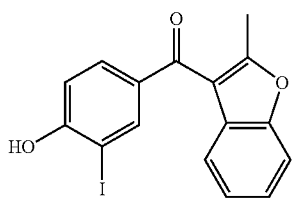 [SMILES: Cc1oc2ccccc2c1C(=O)c1ccc(O)c(I)c1] | 17.5 | | |
| 1g | 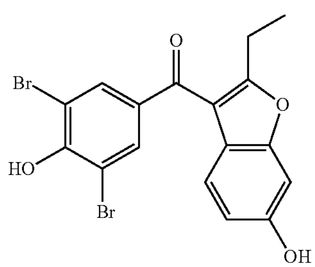 [SMILES: CCc1oc2cc(O)ccc2c1C(=O)c1cc(Br)c(O)c(Br)c1] | 27.2 | | |
| 1h | 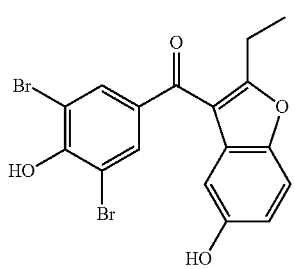 [SMILES: CCc1oc2ccc(O)cc2c1C(=O)c1cc(Br)c(O)c(Br)c1] | 40.8 | | |
| 1i | 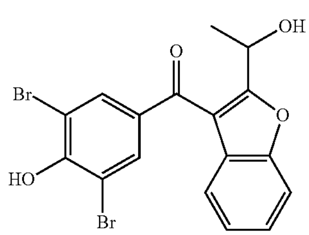 [SMILES: CC(O)c1oc2ccccc2c1C(=O)c1cc(Br)c(O)c(Br)c1] | 41.9 | | |

TABLE 1-continued

| Compound | Structure | IC50 (pNPP) Eya3(ED) | EYA3 | PTP1B |
|---|---|---|---|---|
| 1j | 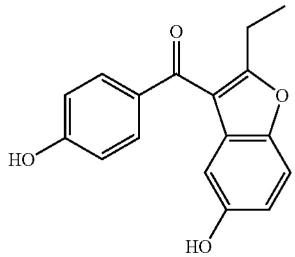 [SMILES: CCc1oc2ccc(O)cc2c1C(=O)c1ccc(O)cc1] | 73.1 | | |
| 1k | 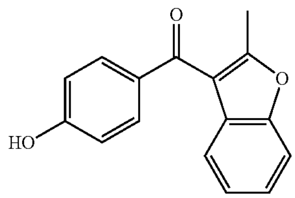 [SMILES: Cc1oc2ccccc2c1C(=O)c1ccc(O)cc1] | 81.1 | | |

Compounds 1, 1a and 1b were assayed for their effect on PTP1B-catalyzed pNPP hydrolysis. PTP1B is a classical Cys-based tyrosine phosphatase. Compounds 1 and 1b showed 4.7-6.5 fold greater activity towards EYA3 than PTP1B, while compound 1a was over 100-fold more specific towards EYA3.

Example 2

Eya Inhibitors Attenuate Cell Migration but not Cell Proliferation

Figure 2A:
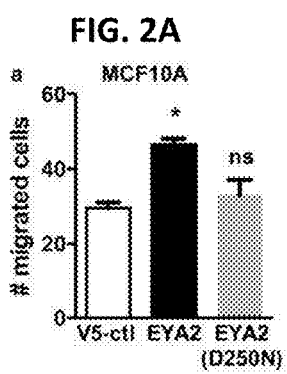
FIGS. 2A-F show that EYA2 overexpression in MCF10A cells increases cell motility, which in turn is inhibited by EYA inhibitors.
Figure 2B:
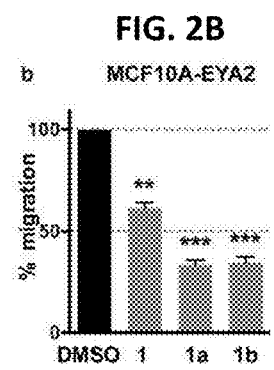
Figure 2C:
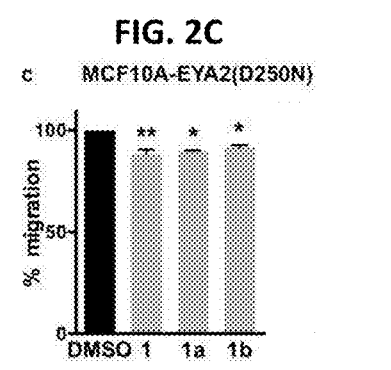
Figure 2D:
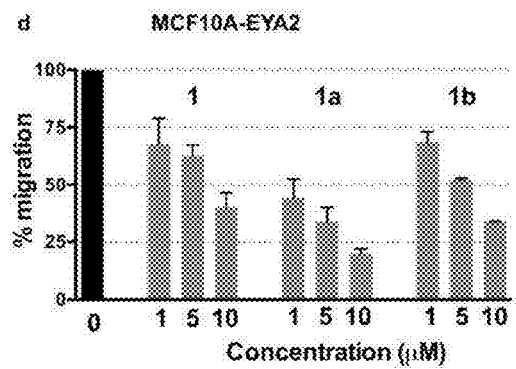

The tyrosine phosphatase activity of Eya3 and Eya2 promotes single cell motility in breast cancer cells (Pandey, R. N. et al. *Oncogene* (2010) 29:3715-3722, incorporated by reference in its entirety). EYA2 is over-expressed in breast cancers and is associated with increased metastasis and a poorer outcome (Farabaugh, et al. *Oncogene* (2011) 259). The migration of immortalized, non-transformed mammary epithelial cells (MCF10A) stably transfected with EYA2 or EYA2(D250N) (in which the nucleophilic Asp is replaced by an Asn rendering the enzyme inactive) was measured using transwell inserts. Overexpression of EYA2, but not the tyrosine-phosphatase dead mutant, promoted cell motility (FIG. 2a). Next, the migration of MCF10A(EYA2) cells in the presence of 7.5 µM of compounds 1, 1a and 1b was measured (FIG. 2b). Each of the three compounds significantly inhibited cell migration. This effect was dose-dependent (FIG. 2d) and compound (1a) was able to reduce cell motility by over 50% at the lowest concentration (1 µM) tested. Furthermore, the EYA inhibitors reduced the motility of cells over-expressing the phosphatase-dead mutant EYA2 (D250N) by less than 10%, comparable to that observed with control MCF10A cells (FIG. 2c).

Figure 2E:
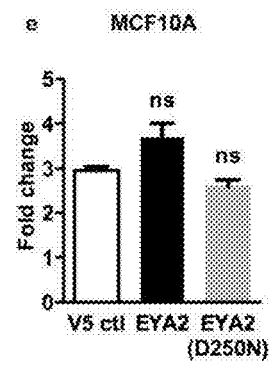
Figure 2F:
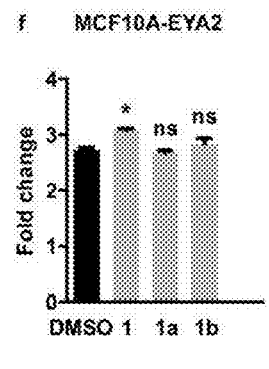

To assess the cellular toxicity of the compounds and their effect on cell proliferation the colorimetric tetrazolium salt MTT assay, which monitors the metabolic activity of cultured cells, was used. Over-expression of EYA2 or the mutant EYA2(D250N) had insignificant effect on MCF10A cell proliferation (FIG. 2e), and none of the EYA inhibitors led to any significant change in proliferation of MCF10A-EYA2 cells (FIG. 2f). Together, these data demonstrate that the EYA tyrosine phosphatase inhibitors in Table 1 inhibit the motility of mammary epithelial cells over-expressing EYA2 at concentrations that are not cytotoxic.

Example 3

Eya3 Promotes Endothelial Cell Migration and Capillary Tubule Formation

Figure 3A:
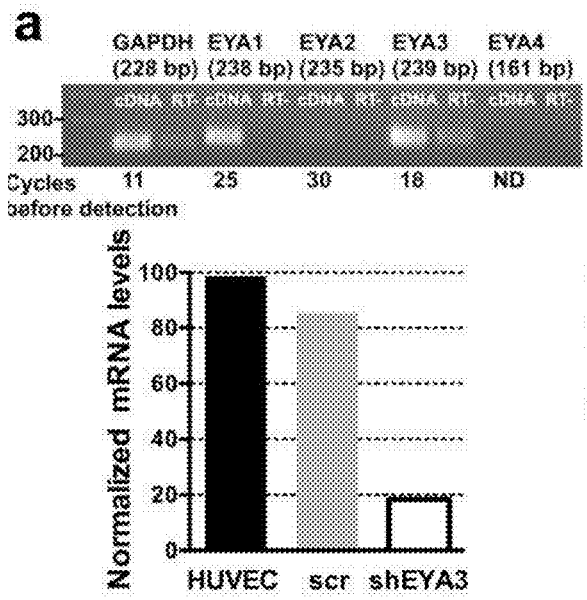
FIGS. 3A-D show migration and tube formation in HUVEC cells treated with shEYA3.

The following experiments were conducted to determine whether EYA3 has a role in endothelial cell migration and in tubule formation. First, using RT-PCR, mRNA for EYA1 and EYA3 were strongly detected in human umbilical vein endothelial cells (HUVECs) (FIG. 3a). Thus, to determine whether EYA3 played a role in endothelial cell migration, EYA3 was knocked down using short hairpin RNAs (shRNA) as follows. Briefly, HUVECs were incubated overnight with shEYA3 or scramble control lentiviral suspension in the presence of 8 µg/ml polybrene. The next day, viral suspension was replaced by fresh medium. 24 hrs later, cells were selected with 2 µg/ml puromycin until control cells were all dead (after 72 hrs of selection). Quantitative real-time PCR (qRT-PCR) showed nearly 75% reduction relative to the scramble control (FIG. 3a).

Figure 3B:
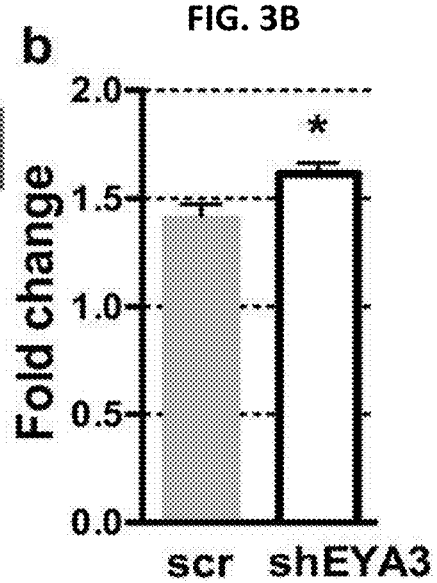

Next, cell proliferation was measured in cells with EYA3 knock down. Briefly, HUVEC cells were plated at 2,000 cells/100 µl/well in a collagen I coated 96-well plate and cultured at 37° C. in a humidified incubator in the presence of 5% $CO_2$. For each condition and time point, the culture was set up in triplicate. After the desired incubation time, the number of viable cells was estimated using the cell counting kit-8 (Oojindo Molecular Technologies, Rockville, Md.). The cell density was expressed as the mean absorbance at 450 nm. Cell proliferation was unaltered in these cells, as shown in FIG. 3b.

Figure 3C:
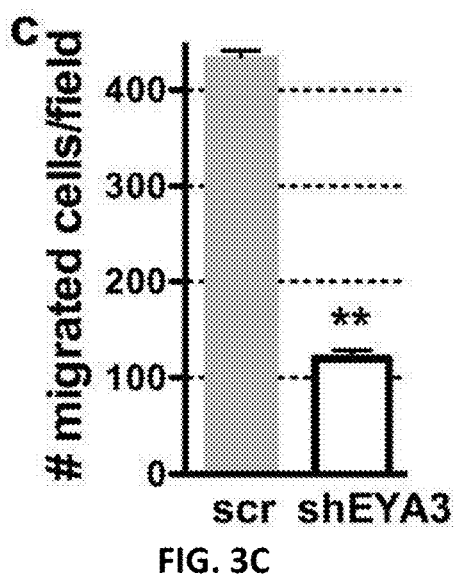

In order to determine whether EYA3 knock down would affect cell migration, a modified Boyden chamber assay was used to measure HUVEC migration. Briefly, human umbilical vein endothelial cells (HUVECs) were purchased from Lonza (Walkersville, Md.) and maintained in the endothelial cell growth medium (PromoCell, Heidelberg, Germany), under a 5% $CO_2$ atmosphere. MCF10A cells from ATCC were stably transfected with either pcDNA 3.2N5-DEST (vector control), V5-EYA2 or V5-EYA2(D250N). Transwell migration experiments were performed as previously described (Pandey, R. N. et al. *Oncogene* 29, 3715-3722, (2010)). These transwell migration assays demonstrated that a significant attenuation upon knockdown of EYA3 was detected, as shown in FIG. 3c.

Additionally, a cell viability assay was conducted over 3 days of exposure to test compounds 1, 1a and 1g in order to assess both the possibility of immediate cellular toxicity as well as any effect on cell proliferation. HUVECs were seeded and equilibrated for 24 hours before addition of the test compounds. Cellular metabolic activity was measured at defined time-points using the tetrazolium dye WST-8 to quantify NAD(P)H-dependent cellular oxidoreductase enzyme activity. Compound 1g showed over 50% reduction in cell proliferation. Treatment with compounds 1 and 1a also reduced cell viability.

Figure 3D:
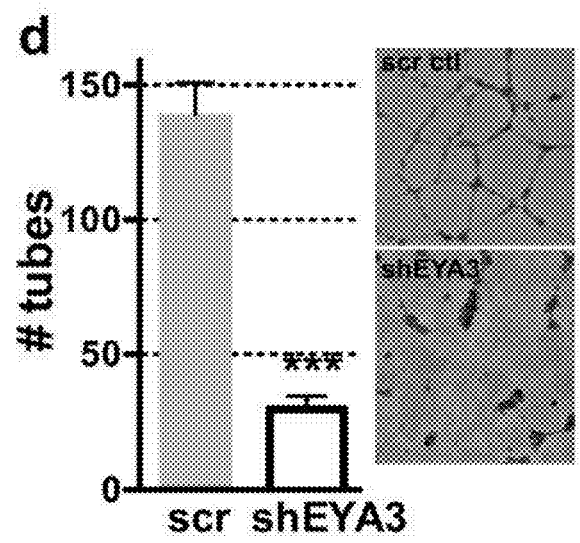

Because cell migration plays a key role in angiogenesis, an in vitro angiogenesis assay was next conducted. Knockdown of EYA3 significantly reduced the ability of HUVECs to form capillary tubes on Matrigel, as shown in FIG. 3d. Together these data indicate that EYA3 plays a role in endothelial cell remodeling, most likely by promoting cell migration.

Additionally, the effect of compounds 1, 1a, 1b, 1d, 1f, 1h, 1g, 2 and 2a on cell migration was assessed using a scratch wound healing assay and HUVEC cells. Cells were plated and grown to confluency. Scratch wounds were made using a sterile pipette tip, the medium changed to remove any cellular debris, and fresh medium with either vehicle or test compound was introduced. The number of cells that migrated into the cleared space was counted 22 hours later. Compound 1g was the most effective inhibitor reducing cell migration by nearly 80%.

Primary endothelial cells (ECs) on basement membrane rapidly attach, align themselves and form capillary-like tubules with lumens and tight cell-cell contacts. HUVECs seeded on Matrigel form relatively short tubes (no more than 2-3 ECs) and it has been suggested that these tubes represent the meeting of ECs that are pushing out or migrating from aggregates of ECs observed after a few hours of plating on Matrigel. Compound 1 and 1a inhibit EYA3 protein in cell migration and tubulogenesis. However, compound 1g has a much stronger inhibitory effect than compound 1a. Compounds 1d, 1f, 1h, 2 and 2a did not show significant attenuation of tube formation. Compound 1g treated cells formed EC aggregates that did not migrate out and form tubes. To better understand the stage in matrigel tube-formation affected by compound 1g cells plated on growth-factor reduced matrigel and treated with either vehicle or compound 1g were followed. Differences become apparent within the first two hours and were clearly visible at the 6-hour time-point. The ECs are much less organized in the presence of compound 1g. By 20 hours they form cellular aggregates but there are no tubules interconnecting the aggregates to form the characteristic microvascular network, supporting the suggestion that the inhibitor affects EC migration. The effect of compound 1g on tube formation was attenuated in the presence of high concentrations of fetal bovine serum (FBS), likely reflecting non-specific protein binding.

Additionally, the effect of compounds 1d, 1f, 1h, 1i, 1g, 2 and 2a on cell proliferation, migration, tube formation, micro-vessel branching, and perivascular recruitment using an aortic ring sprouting assay. When slices of mouse aorta are cultured in collagen gels there is typically a lag phase for the first 4 days followed by linear sprouting of endothelial cells. By day 6, branching is observed. All the test compounds were initially assayed at 7.5 µM and the number of branch-points counted. When there was a severe effect (no visible sprouting), or when there was no apparent effect, other doses were tested to establish a dose-dependence. All of the compounds assayed were able to attenuate aortic ring sprouting. There was a strong reduction in initial sprouting and some attenuation of branching. With the exception of 2a, in all cases where there was sprouting, the length of sprouts was shorter than in the controls. These observations suggest that the effect of the compounds on angiogenesis was likely due to inhibition of endothelial cell migration. As in the previous assays compound 1g was the most potent inhibitor.

Example 4

Eya Inhibitors have Anti-Angiogenic Activity

Figures 4A, 4B, 4C, 4D:
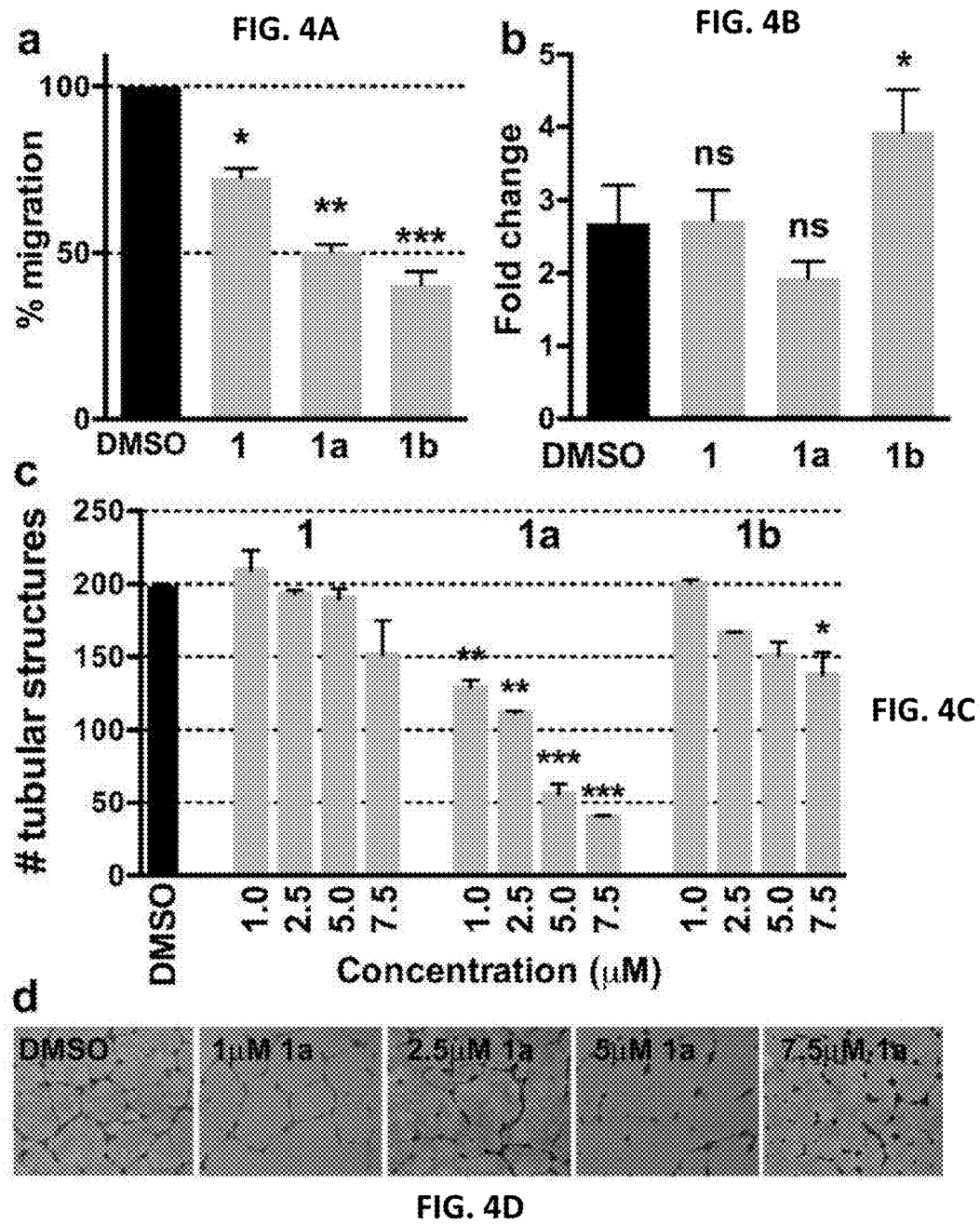

To specifically query the role of the EYA tyrosine phosphatase activity in endothelial cell migration and angiogenesis, the EYA inhibitors 1, 1a and 1b were used. As in the case of MCF10A-EYA2 cells, all of these compounds attenuated HUVEC cell motility, as shown in FIG. 4a. In parallel experiments using MTT, no effect on cell proliferation was measured, as shown in FIG. 4b.

The EYA inhibitors were also tested in tubulogenesis assays. The tubulogenesis assays were performed in 15-well micro-slide (ibidi LLC, Verona Wis.), using growth factor-reduced matrigel (BD Bioscience, Billerica, Mass.). The matrix was prepared by loading 10 µl of matrigel in each micro-slide well and allowing it to solidify for 30 minutes at 37° C. HUVECs were trypsinized and resuspended at 100,000 cell/ml in EBM+2.5% FBS. 50 µl (5,000 cell) were loaded on top of the solidified matrigel and the preparation was incubated for 20 hours at 37° C. in a humidified incubator in a 5% $CO_2$ atmosphere. Bright field images were taken using an inverted microscope at 2.5× magnification, which allowed imaging of the whole well in two pictures that were later merged in Photoshop. Tubular structures were traced and counted using NeuroJ (NIH, USA). In experiments with inhibitor, the inhibitor was added to the cell suspension before loading. Each sample was loaded in triplicate, and each treatment was repeated for reproducibility. As shown in FIG. 4c, compound 1a potently inhibited tubulogenesis in a dose-dependent fashion, showing nearly 50% reduction in tube formation at 2.5 µM. Compounds 1 and 1b were effective at the highest concentrations tested (7.5 µM).

Endothelial cell migration can also be studied ex vivo using the aortic ring assay in which sprouting angiogenesis is monitored by the formation of vascular sprouts outside the wall of mouse aortic rings incubated in collagen matrix and stimulated by VEGF (Gerhardt, H., et al. *EXS*, 3-15 (2005), hereby incorporated by reference in its entirety). Briefly, mice were obtained from the Cincinnati Children's veterinary service and handled according to the institutional animal care and use protocol. The preparation of rat collagen and the aortic ring assay were carried out as previously described (Aplin, A. C., et al., *Methods Enzymo*/443, 119-136, (2008); Reed, M. J., Damodarasamy, M. & Vernon, R. B. *The open circulation & vascular journal* 4, 12-17 (2011), each of which is hereby incorporated by reference in its entirety). Mice were 4 to 6 weeks old female C57BL16, and aortic ring explants were cultured at 37° C. in a humidified incubator under a 5% $CO_2$ atmosphere.

Figure 7:
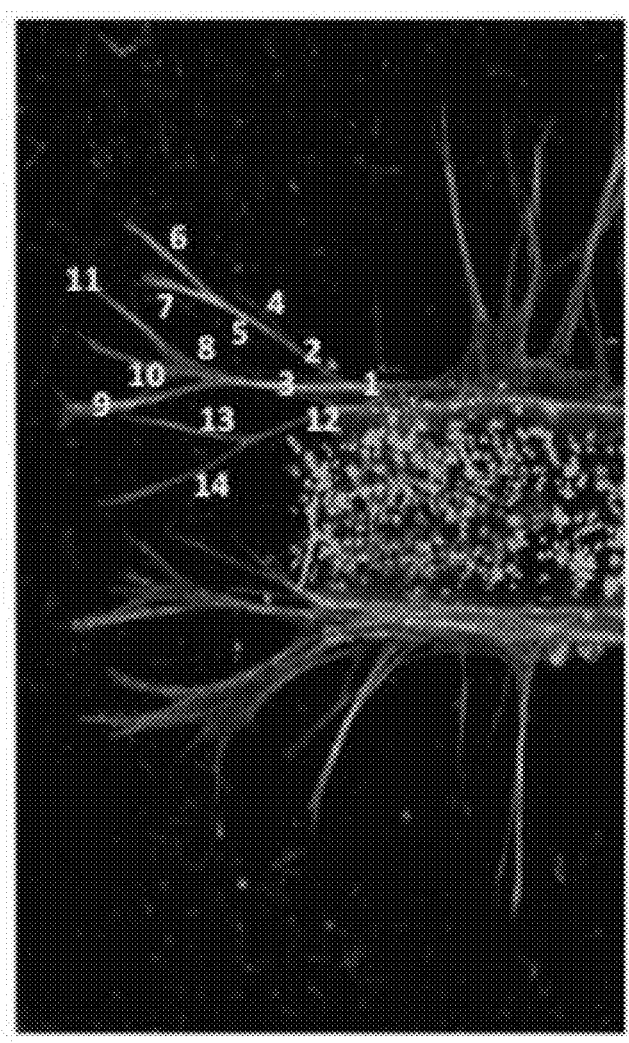
FIG. 7 shows scoring of sprouting in aortic rings. Vessel branching was counted from the ring to the tip of each vessel, and each split (branching point) is counted as two additional branches as shown.

Each inhibitor was serially diluted (between 0.25 mM and 7.5 mM) to stocks of 1000× the working concentrations in sterile 100% DMSO in order to achieve an equal final concentration of DMSO (0.1% v/v) in all culture conditions. For the experiments, the compounds were diluted in EBM containing 2.5% FBS, penicillin/streptomycin and 20 ng/ml VEGF165 (R&D Systems, Minneapolis, Minn.). Each compound was applied from the first day of culture over a 10-day period with medium change every two days. In all experiments, the vehicle (DMSO, 0.1%) was used as control. The sprouting density was derived from counting the number of branches per ring, and the extent of angiogenic sprouting was estimated by measuring the total surface area covered by the vessels as illustrated in FIG. 7.

Figure 5A:
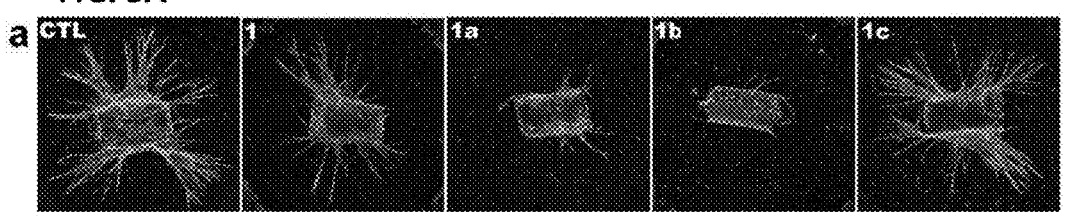
FIGS. 5A-C show that EYA inhibitors attenuate sprouting angiogenesis.
Figure 5B:
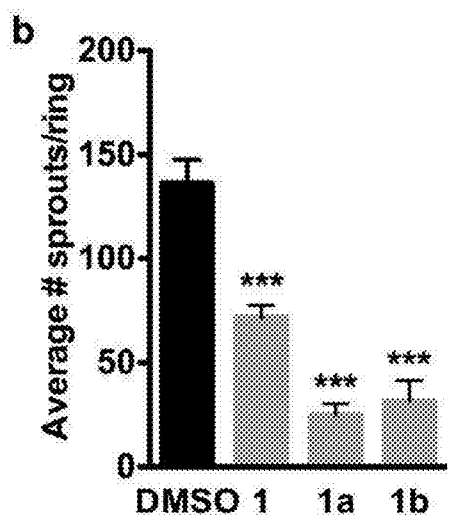
Figure 5C:
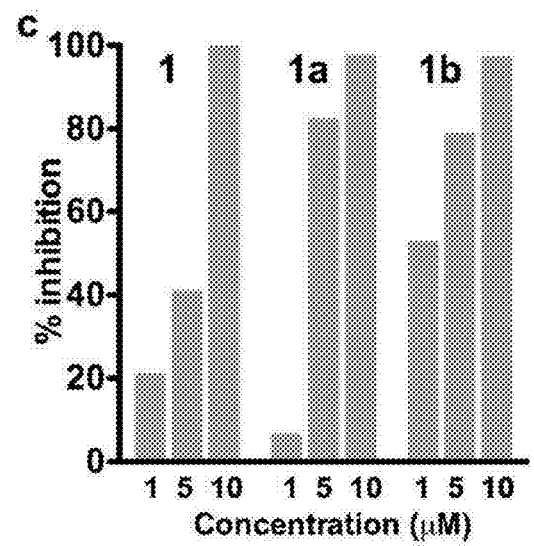

As shown in FIG. 5a, vehicle-treatment (0.1% DMSO) of mouse aortic rings resulted in an extensive microvascular network with an average maximal sprout length of 900 μM after 10 days. In contrast, aortic rings treated with 5 μM of compounds 1, 1a, and 1b exhibited shorter sprouts and significantly lower microvascular density (FIG. 5a). This inhibition was dose-dependent (FIG. 5c). The observations described here thus support a role for the EYA tyrosine phosphatase activity in endothelial cell motility and angiogenesis, but not cell proliferation.

Example 5

Eya Tyrosine Phosphatase Inhibition has an Anti-Angiogenic Effect in a Zebrafish Model In order to test the possibility that the EYAs are angiogenic in the more complex, context-driven environment encountered by blood vessels in vivo we used the well-characterized zebrafish model of angiogenesis (See, e.g., Langheinrich, U. *BioEssays: news and reviews in molecular, cellular and developmental biology* 25, 904-912, (2003); Staton, C. A., et al. *International journal of experimental pathology* 90, 195-221, (2009), each of which is hereby incorporated by reference in its entirety).

Embryos (FLK1-GFP trangenic) were maintained in fish water until the 50% epiboly stage (5.25 hpf) and were transferred into wells of 24-well plate containing the inhibitors in fish water. The analysis for vascular defects was performed after the 24 hpf stage, and embryos were imaged using a fluorescence microscope.

Transgenic fish expressing EGFP in endothelial cells (Tg(flk1:EGFP)) were used to facilitate visualization of the developing vasculature. In control experiments embryos were treated with 0.1% DMSO (vehicle). At the time of analyses (24 hpf) developing vessels normally migrated from the lateral plate mesoderm to the midline and formed the vascular cord, subsequently forming the dorsal aorta and the posterior cardinal vein and followed by the formation of intersegmental vessels at designated branch points (FIG. 6b). Experimental embryos were exposed to varying doses of compounds 1, 1a and 1b (FIG. 6c). Dose-dependent defects in the developing vasculature were observed in all cases (FIG. 6a), ranging from a reduction in intersegmental vessel number and extension at lower doses to changes in the dorsal aorta and cardinal vein at higher doses. Representative images are shown in FIG. 6c. Compound 1 (Benzbromarone) was the most potent showing significant reduction of intersegmental vessels even at the lowest dose tested (0.25 μM). Compounds 1a and 1b also reduced the number of intersegmental vessels, but were less potent.

When embryos were exposed to the compounds starting at a later stage (20 hpf) no defects in the vasculature or general morphology were observed.

This analysis confirms that Eya has an important role in promoting developmental angiogenesis and that the Eya inhibitors are effective in an in vivo experimental system.

Example 6

Eya3 is Required for Normal Retinal Angiogenesis

Retinal angiogenesis was used as a model to further characterize the role of Eya3 in angiogenesis. First, endpoint PCR was performed to assess the expression of Eya1-4 in hyaloid vessels and MVECs. The results, shown in FIG. 8a, confirmed expression of Eya1 and Eya3 in hyaloid vessels and MVECs.

Next, retinal blood vessel density and angiogenic extension were studied using induced deletion of Eya3 in mice by PDGFB-icreERT2 starting at the day of birth. Isolectin labeled retinal blood vessels at postnatal day 5 in control Eya3fl/fl (FIGS. 8b and 8d) and experimental Eya3fl/fl; PDGFB-icreERT2 (FIGS. 8c and 8c) mice. FIGS. 8d and 8e are magnified images of the regions indicated in 8b and 8c, respectively. These results show that induced deletion of Eya3 in mice by PDGFB-icreERT2 starting at the day of birth results in quantifiable defects in angiogenic extension (FIG. 8f) and vessel density (FIG. 8g).

Figure 9:
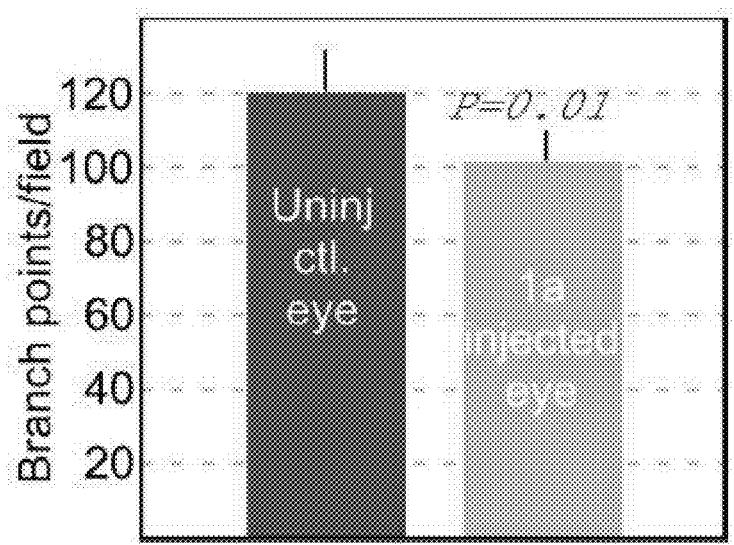
FIG. 9 is a bar graph showing the effect of injection of compound 1a on post-natal retinal angiogenesis.

Next, treatment with an inhibitor of Eya3 was performed to test the effect on post-natal retinal angiogenesis. Briefly, 100 μM of compound 1a was injected into the eyes of post-natal mice, at P0.5 and P3. P5 retinas were then analyzed for effects on the retinal vasculature. The results are set forth in FIG. 9, which shows a quantifiable decrease in branch points in the treated mice.

Using the VEC-specific Eya3 knockout model discussed above, injection of compound 1a resulted in an additional significant reduction in retinal angiogenesis under normal oxygen conditions.

While the present embodiments have been described in connection with what is presently considered to be practical exemplary embodiments, it is to be understood that the invention is not limited to the disclosed embodiments and is intended to cover various modifications and equivalent arrangements included within the spirit and scope of the appended claims.

Example 7

Eya Inhibitors Inhibit Proliferative Retinopathy in Animal Model

Figure 11A:
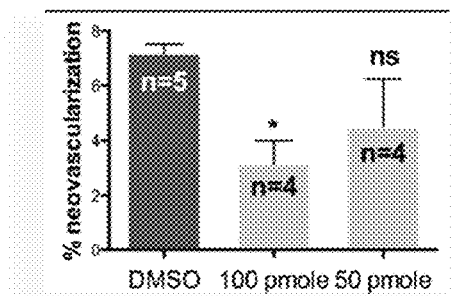
FIGS. 11A and B show the effect of administration of an EYA inhibitor on an animal model of proliferative retinopathy.
Figure 11B:
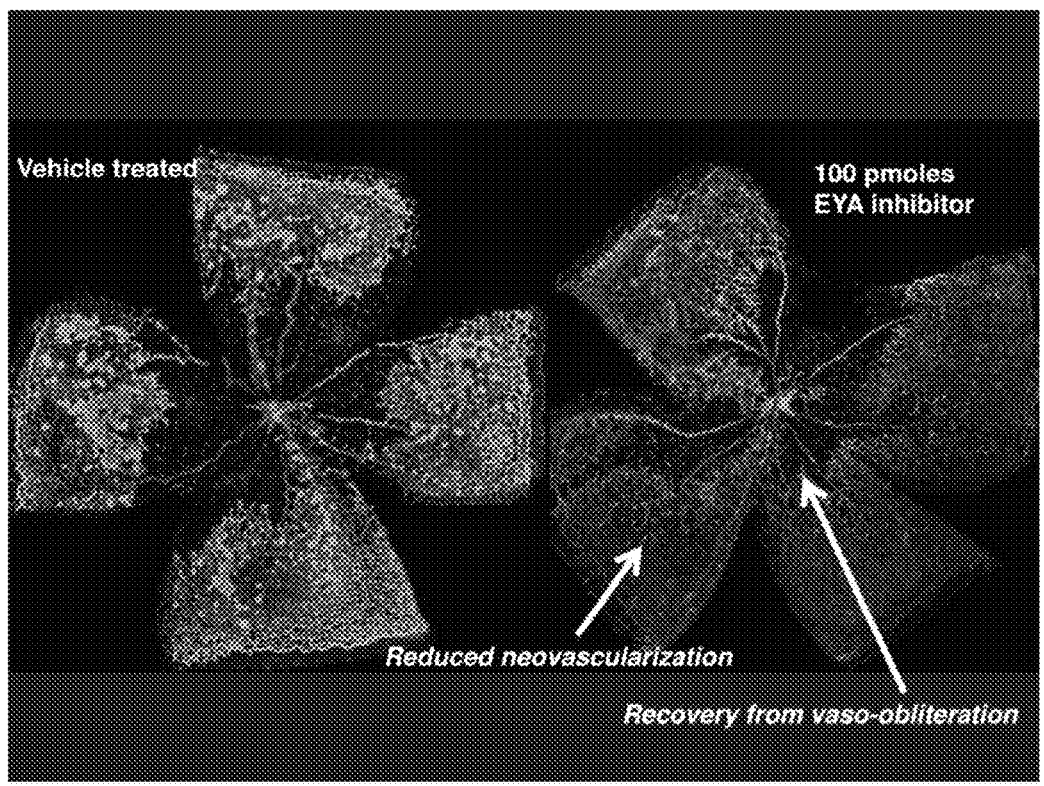
FIG. 11B shows isolectin labeled retinal blood vessels at postnatal day 16 in control (vehicle treated) and experimental (100 pmoles EYA inhibitor) mice.

The mouse model of oxygen-induced retinopathy mimics the retinopathy characteristic of proliferative retiopathy conditions such as retinopathy of prematurity and diabetic retinopathy. Experiments were performed by exposing of 7 day old pups to 75% $O_2$ for 5 days or 85% $O_2$ for 3 days, which resulted in obliteration of the developing retinal vascular network. The resulting retinal hypoxia after day 12, when pups were brought back to 20% $O_2$, induced excessive hypoxia-driven angiogenesis. A characteristic large avascular area at the center of the retina and excessive regrowth of superficial vessels (pre-retinal neovascular tufts) in the mid-peripheral region was observed. As an initial assessment of the effect of EYA inhibition either 100 or 50 pmoles of compound 1, 1a, 1b (see Table 1), and blank negative control was injected at P12 in mice subject to the 3-day hyperoxia protocol, and retinal vasculature analyzed at P16 (at least 4 mice were used in each group, three independent experiments). Significant reduction in the formation of neovascular tufts and revascularization into the vaso-obliterated area were similar to the untreated eye (see FIGS. 11a and 11b). In contrast, inhibition of either Vegf or Vegfr2 in OIR experiments suppresses both neovascular tuft formation and revascularization. These experiments demonstrate that EYA inhibitors reduced pathological neovascularization in an in vivo model for proliferative retinopathy.

Example 8

Eya Inhibitors Inhibit Tumors in Animal Model

Figure 12:
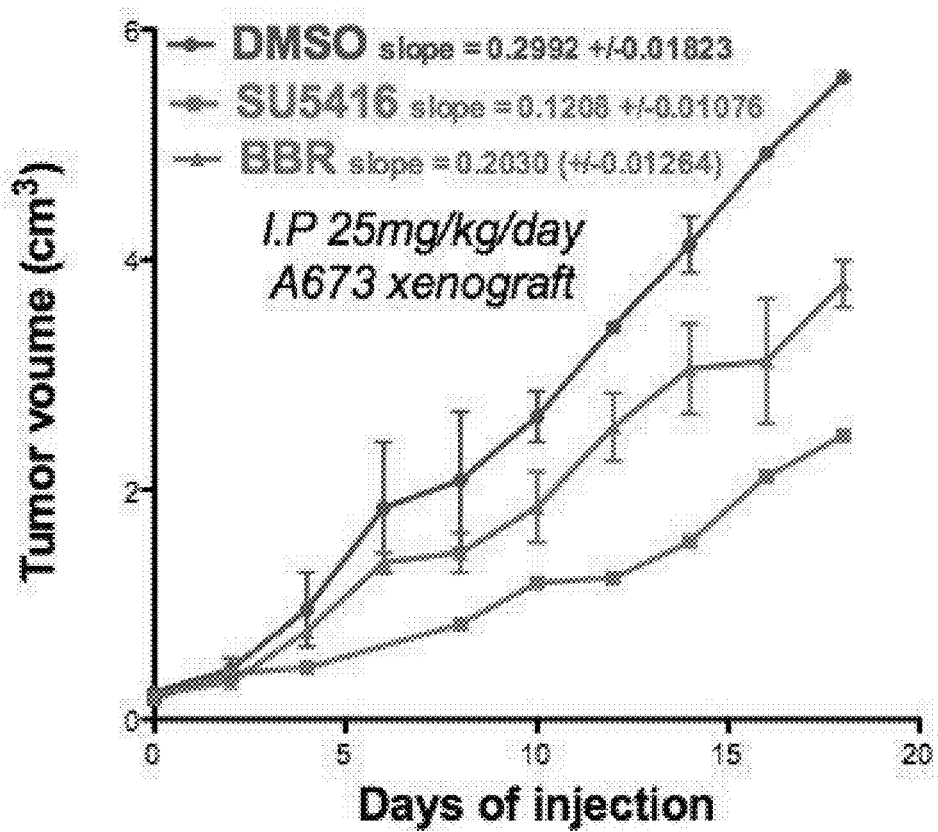
FIG. 12 shows the effect of administration of an EYA inhibitor on an animal model of Ewing sarcoma. The graph shows quantitative analysis of inhibition of tumor growth by an EYA inhibitor (BBR), compared to negative control (DMSO) and positive control (SU5416).

The affect of EYA inhibitors on a mouse xenograft model of Ewings sarcoma was tested. 5×10⁶ A673 (Ewings sarcoma) cells in 0.1 ml sterile matrigel were injected subcutaneously into the dorsal flank region of nude mice. Approximately 5 days after injection, the tumors were about 100-300 mm³. Either intra-peritoneal or intra-tumor injections of compounds 1, 1a and 1b (see Table 1), Vegf inhibitor SU5416 (positive control), and vehicle (negative control) were initiated using DMSO as the vehicle. The dose for intra-peritoneal injections was 25 mg/kg/day. The tumor size was monitored every other day. Animals were sacrificed after 2 weeks, or when tumor volume approached 10% of animal weight. FIG. 12 shows an example of the results where compound 1 (BBR) was able to reduce tumor growth.

Example 9

Inhibition of Eya 3 Catalytic Activity

Compounds 2 and 2a were assayed as described in Example 1. These results demonstrate that compound 2 and 2a inhibit the phosphatase activity of Eya3.

A summary of the results is shown in Table 2.

TABLE 2

| Compound | Structure | IC50 (pNPP) Eya3(ED) | EYA3 | PTP1B |
|---|---|---|---|---|
| 2 | (structure) | | | 3.1 |
| 2a | (structure) | | | 16.4 |

What is claimed is:

1. A compound having the structure of Formula I:

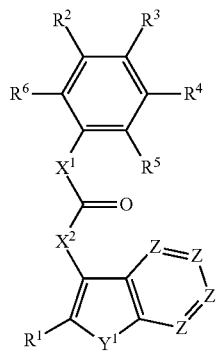

or a pharmaceutically acceptable salt thereof,
wherein:

$R^1$ is selected from the group consisting of $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, (cyclolalkyl)alkyl, and amino, said $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, and (cyclolalkyl)alkyl are each optionally substituted with one or more $R^{1A}$;

each $R^{1A}$ is independently selected from the group consisting of hydroxy, halo, cyano, nitro, $C_{1-6}$ alkyl optionally substituted with up to 5 fluoro, $C_{1-6}$ alkoxy optionally substituted with up to 5 fluoro;

$R^2$ is selected from the group consisting of H (hydrogen), halo, hydroxy, and $C_{1-6}$ alkyl substituted with one or more hydroxy;

$R^3$ is selected from the group consisting of halo, hydroxy, and $C_{1-6}$ alkyl substituted with one or more hydroxy;

$R^4$ is H (hydrogen) or halo;

$R^5$ and $R^6$ are each independently selected from the group consisting of H (hydrogen), halo, cyano, $C_{1-6}$ alkyl, aryl, heteroaryl, heterocyclyl, and amino, said $C_{1-6}$ alkyl, aryl, heteroaryl, and heterocyclyl each optionally substituted with one or more $R^{1A}$;

$X^1$ is $[C(R^{2A})_2]_n$, O (oxygen), or $NR^{2A}$, or $X^1$ is absent;

$X^2$ is $[C(R^{2A})_2]_n$, O (oxygen), or $NR^{2A}$, or $X^2$ is absent;

each $R^{2A}$ is independently selected from the group consisting of H (hydrogen), halo, O-carbamyl, N-carbamyl, C-amido, S-sulfonamido, N-sulfonamido, C-carboxy, amino, aryl, heteroaryl, heterocyclyl, arylalkyl, heteroarylalkyl, heterocyclylalkyl, cycloalkyl, cycloalkenyl, (cyclolalkyl)alkyl, $C_{1-6}$ alkyl substituted with one or more hydroxyl, and $C_{1-6}$ alkyl optionally substituted with up to 5 fluoro;

each n is independently 1 or 2;

$Y^1$ is O (oxygen); and each Z is independently selected from the group consisting $CR^{2A}$, and N (nitrogen), with the proviso that the compound is not:

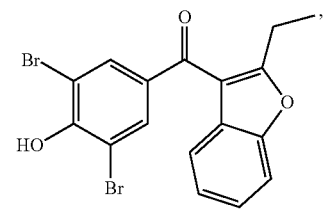

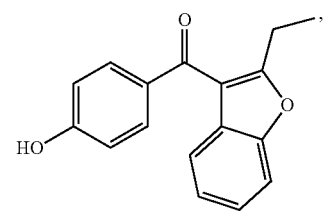

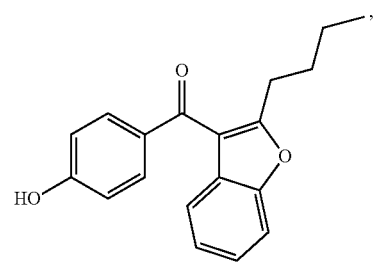

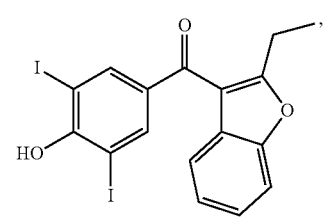

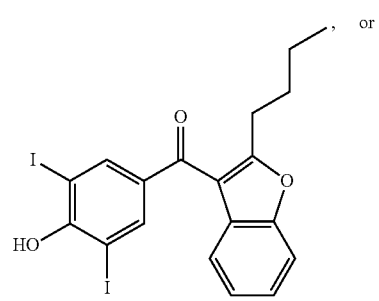

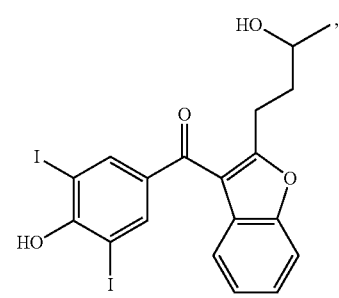

or a pharmaceutically acceptable salt thereof.

2. The compound of claim 1, wherein the compound having the structure of Formula I has the structure of Formula Ia, or Ib,

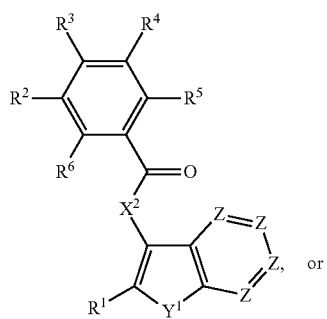

(Ia)

or

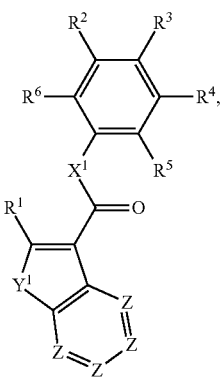

(Ib)

or a pharmaceutically acceptable salt thereof.

5. The compound of claim 1, wherein the compound of Formula I has the structure of Formula II:

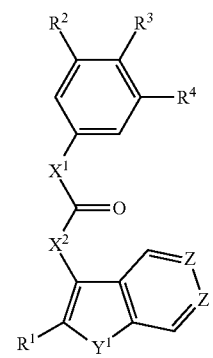

II or a pharmaceutically acceptable salt thereof, wherein:
X$^1$ is O (oxygen), or NR$^{2A}$, or X$^1$ is absent;
X$^2$ is O (oxygen), or NR$^{2A}$, or X$^2$ is absent;
each R$^{2A}$ is independently selected from the group consisting of H (hydrogen), halo, C$_{1-6}$ alkyl substituted with one or more hydroxyl, and C$_{1-6}$ alkyl optionally substituted with up to 5 fluoro; and
Y$^1$ is O (oxygen), or S (sulfur).

6. The compound of claim 5, wherein the compound having the structure of Formula II has the structure of Formula IIa, or IIb,

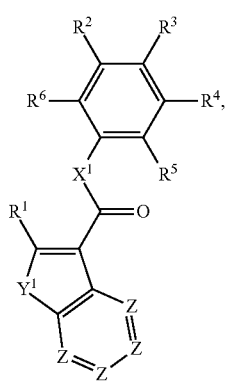

(Ib)

or a pharmaceutically acceptable salt thereof.

3. The compound of claim 2, wherein the compound having the structure of Formula I has the structure of Formula Ia,

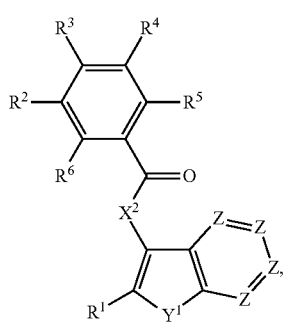

(Ia)

or a pharmaceutically acceptable salt thereof.

4. The compound of claim 2, wherein the compound having the structure of Formula I has the structure of Formula Ib,

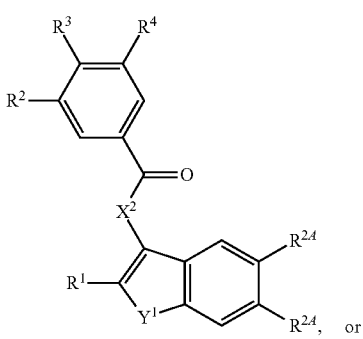

(IIa)

or

-continued

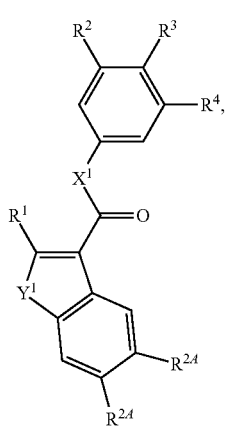

(IIb)

or a pharmaceutically acceptable salt thereof, wherein $R^2$ and $R^4$ are each independently H (hydrogen) or halo; and each $R^{2A}$ is independently hydrogen, or halo.

7. The compound of claim 6, wherein the compound having the structure of Formula II has the structure of Formula IIa,

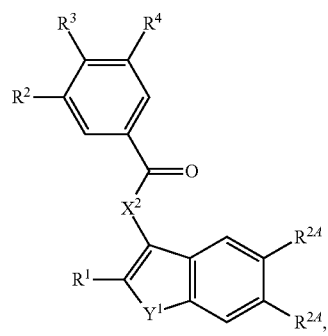

(IIa)

or a pharmaceutically acceptable salt thereof.

8. The compound of claim 6, wherein the compound having the structure of Formula II has the structure of Formula IIb,

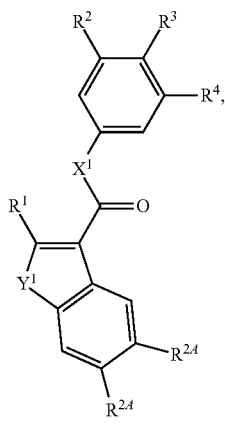

(IIb)

or a pharmaceutically acceptable salt thereof.

9. A compound having the structure of Formula III:

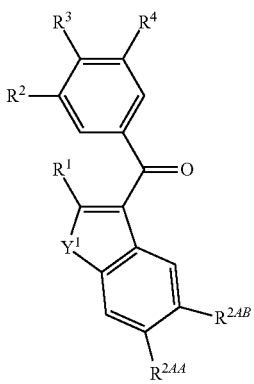

III or a pharmaceutically acceptable salt thereof, wherein:

$R^1$ is selected from the group consisting of $C_{1-6}$ alkyl, $C_{2-6}$ alkenyl, $C_{2-6}$ alkynyl, aryl, heteroaryl, heterocyclyl, arylalkyl, heteroarylalkyl, heterocyclylalkyl, cycloalkyl, cycloalkenyl, (cyclolalkyl)alkyl, and amino, said $C_{1-6}$ alkyl, $C_{2-6}$ alkenyl, $C_{1-6}$ alkynyl, aryl, heteroaryl, heterocyclyl, arylalkyl, heteroarylalkyl, heterocyclylalkyl, cycloalkyl, cycloalkenyl, and (cyclolalkyl)alkyl are each optionally substituted with one or more $R^{1A}$;

each $R^{1A}$ is independently selected from the group consisting of hydroxy, halo, cyano, nitro, $C_{1-6}$ alkyl optionally substituted with up to 5 fluoro, $C_{1-6}$ alkoxy optionally substituted with up to 5 fluoro;

$R^2$ is selected from the group consisting of iodo, hydroxy, and $C_{1-6}$ alkyl substituted with one or more hydroxy;

$R^3$ is halo or hydroxy;

$R^4$ is H (hydrogen) or halo;

$R^{2AA}$ is H (hydrogen) or hydroxyl;

$R^{2AB}$ is H (hydrogen) or hydroxyl; and $Y^1$ is O (oxygen), or S (sulfur)), with the proviso that the compound is not:

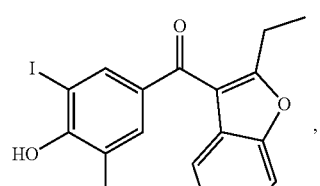

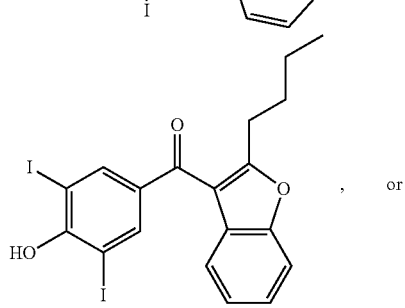

-continued

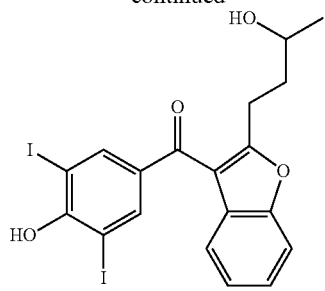

or a pharmaceutically acceptable salt thereof.

10. The compound of claim 9, wherein $R^{2AA}$ is hydroxyl.

11. The compound of claim 9, wherein $R^{2AB}$ is H (hydrogen).

12. The compound of claim 1, wherein $R^1$ is $C_{1-6}$ alkyl optionally substituted with one or more $R^{1A}$.

13. The compound of claim 1, wherein $R^1$ is ethyl.

14. The compound of claim 1, wherein $R^2$ is iodo or bromo.

15. The compound of claim 1, wherein $R^4$ is iodo or bromo.

16. A composition comprising a pharmaceutically acceptable excipient, and a compound of claim 1.

17. The composition of claim 16, wherein the compound is:

-continued or a pharmaceutically acceptable salt thereof.

18. The composition of claim 16 for use in treating proliferative retinopathy, retinopathy of prematurity, diabetic retinopathy, age related macular degeneration, retinal vasculitis, exudative vitreoretinopathy, tumor angiogenesis, hemangiomas, tumor metastasis, treating breast cancer, ductal carcinoma lobule carcinoma, breast epithelial cancer, ovarian cancer, including epithelial ovarian cancer, desmoid tumor, malignant peripheral nerve sheath cancer, acute leukemia, rhabdomyosarcoma, Ewing's sarcoma, extra-skeletal myxoid chondrosarcoma, or endometrial cancer.

19. The composition of claim 18, wherein the compound is:

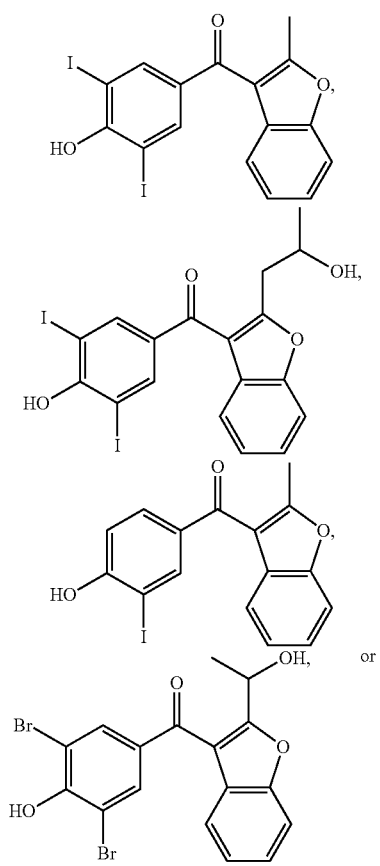

or a pharmaceutically acceptable salt thereof.

20. The composition of claim 18, wherein the compound is:
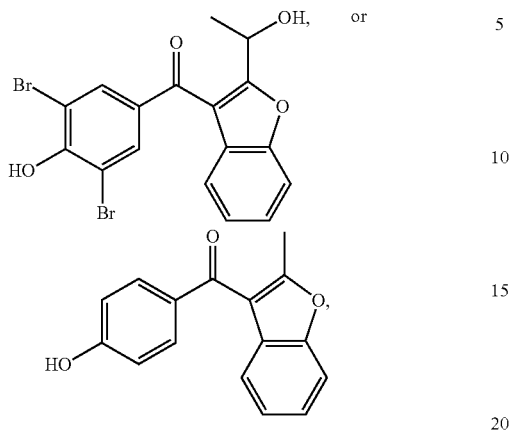
or a pharmaceutically acceptable salt thereof.
* * * * *

```
                        SEQUENCE LISTING

<160> NUMBER OF SEQ ID NOS: 5

<210> SEQ ID NO 1
<211> LENGTH: 273
<212> TYPE: PRT
<213> ORGANISM: Homo sapiens

<400> SEQUENCE: 1

Asp Leu Glu Arg Val Phe Ile Trp Asp Leu Asp Glu Thr Ile Ile Val
 1               5                  10                  15

Phe His Ser Leu Leu Thr Gly Ser Tyr Ala Ser Arg Tyr Gly Arg Asp
                20                  25                  30

Pro Pro Thr Ser Val Ser Leu Gly Leu Arg Met Glu Glu Met Ile Phe
            35                  40                  45

Asn Leu Ala Asp Thr His Leu Phe Phe Asn Asp Leu Glu Glu Cys Asp
        50                  55                  60

Gln Val His Ile Asp Asp Val Ser Ser Asp Asp Asn Gly Gln Asp Leu
 65                  70                  75                  80

Ser Thr Tyr Asn Phe Gly Thr Asp Gly Phe Pro Ala Ala Ala Thr Ser
                85                  90                  95

Ala Asn Leu Cys Leu Ala Thr Gly Val Arg Gly Gly Val Asp Trp Met
                100                 105                 110

Arg Lys Leu Ala Phe Arg Tyr Arg Arg Val Lys Glu Ile Tyr Asn Thr
            115                 120                 125

Tyr Lys Asn Asn Val Gly Gly Leu Leu Gly Pro Ala Lys Arg Glu Ala
```

```
                130                 135                 140
Trp Leu Gln Leu Arg Ala Glu Ile Glu Ala Leu Thr Asp Ser Trp Leu
145                 150                 155                 160

Thr Leu Ala Leu Lys Ala Leu Ser Leu Ile His Ser Arg Thr Asn Cys
                165                 170                 175

Val Asn Ile Leu Val Thr Thr Thr Gln Leu Ile Pro Ala Leu Ala Lys
            180                 185                 190

Val Leu Leu Tyr Gly Leu Gly Ile Val Phe Pro Ile Glu Asn Ile Tyr
            195                 200                 205

Ser Ala Thr Lys Ile Gly Lys Glu Ser Cys Phe Glu Arg Ile Ile Gln
            210                 215                 220

Arg Phe Gly Arg Lys Val Val Tyr Val Val Ile Gly Asp Gly Val Glu
225                 230                 235                 240

Glu Glu Gln Gly Ala Lys Lys His Ala Met Pro Phe Trp Arg Ile Ser
                245                 250                 255

Ser His Ser Asp Leu Met Ala Leu His His Ala Leu Glu Leu Glu Tyr
                260                 265                 270

Leu

<210> SEQ ID NO 2
<211> LENGTH: 273
<212> TYPE: PRT
<213> ORGANISM: Homo sapiens

<400> SEQUENCE: 2

Glu Ile Glu Arg Val Phe Val Trp Asp Leu Asp Glu Thr Ile Ile Ile
1               5                   10                  15

Phe His Ser Leu Leu Thr Gly Thr Phe Ala Ser Arg Tyr Gly Lys Asp
                20                  25                  30

Thr Thr Thr Ser Val Arg Ile Gly Leu Met Met Glu Glu Met Ile Phe
            35                  40                  45

Asn Leu Ala Asp Thr His Leu Phe Phe Asn Asp Leu Glu Asp Cys Asp
        50                  55                  60

Gln Ile His Val Asp Asp Val Ser Ser Asp Asp Asn Gly Gln Asp Leu
65                  70                  75                  80

Ser Thr Tyr Asn Phe Ser Ala Asp Gly Phe His Ser Ser Ala Pro Gly
                85                  90                  95

Ala Asn Leu Cys Leu Gly Ser Gly Val His Gly Val Asp Trp Met
                100                 105                 110

Arg Lys Leu Ala Phe Arg Tyr Arg Arg Val Lys Glu Met Tyr Asn Thr
            115                 120                 125

Tyr Lys Asn Asn Val Gly Gly Leu Ile Gly Thr Pro Lys Arg Glu Thr
130                 135                 140

Trp Leu Gln Leu Arg Ala Glu Leu Glu Ala Leu Thr Asp Leu Trp Leu
145                 150                 155                 160

Thr His Ser Leu Lys Ala Leu Asn Leu Ile Asn Ser Arg Pro Asn Cys
                165                 170                 175

Val Asn Val Leu Val Thr Thr Thr Gln Leu Ile Pro Ala Leu Ala Lys
            180                 185                 190

Val Leu Leu Tyr Gly Leu Gly Ser Val Phe Pro Ile Glu Asn Ile Tyr
            195                 200                 205

Ser Ala Thr Lys Thr Gly Lys Glu Ser Cys Phe Glu Arg Ile Met Gln
            210                 215                 220

Arg Phe Gly Arg Lys Ala Val Tyr Val Val Ile Gly Asp Gly Val Glu
```

```
                225                 230                 235                 240
Glu Glu Gln Gly Ala Lys Lys His Asn Met Pro Phe Trp Arg Ile Ser
                245                 250                 255
Cys His Ala Asp Leu Glu Ala Leu Arg His Ala Leu Glu Leu Glu Tyr
            260                 265                 270
Leu

<210> SEQ ID NO 3
<211> LENGTH: 273
<212> TYPE: PRT
<213> ORGANISM: Homo sapiens

<400> SEQUENCE: 3

Glu Leu Glu Arg Val Phe Leu Trp Asp Leu Asp Glu Thr Ile Ile Ile
1               5                   10                  15
Phe His Ser Leu Leu Thr Gly Ser Tyr Ala Gln Lys Tyr Gly Lys Asp
            20                  25                  30
Pro Thr Val Val Ile Gly Ser Gly Leu Thr Met Glu Glu Met Ile Phe
        35                  40                  45
Glu Val Ala Asp Thr His Leu Phe Phe Asn Asp Leu Glu Glu Cys Asp
    50                  55                  60
Gln Val His Val Glu Asp Val Ala Ser Asp Asp Asn Gly Gln Asp Leu
65                  70                  75                  80
Ser Asn Tyr Ser Phe Ser Thr Asp Gly Phe Ser Gly Ser Gly Gly Ser
                85                  90                  95
Gly Ser His Gly Ser Ser Val Gly Val Gln Gly Gly Val Asp Trp Met
            100                 105                 110
Arg Lys Leu Ala Phe Arg Tyr Arg Lys Val Arg Glu Ile Tyr Asp Lys
        115                 120                 125
His Lys Ser Asn Val Gly Gly Leu Leu Ser Pro Gln Arg Lys Glu Ala
    130                 135                 140
Leu Gln Arg Leu Arg Ala Glu Ile Glu Val Leu Thr Asp Ser Trp Leu
145                 150                 155                 160
Gly Thr Ala Leu Lys Ser Leu Leu Leu Ile Gln Ser Arg Lys Asn Cys
                165                 170                 175
Val Asn Val Leu Ile Thr Thr Thr Gln Leu Val Pro Ala Leu Ala Lys
            180                 185                 190
Val Leu Leu Tyr Gly Leu Gly Glu Ile Phe Pro Ile Glu Asn Ile Tyr
        195                 200                 205
Ser Ala Thr Lys Ile Gly Lys Glu Ser Cys Phe Glu Arg Ile Val Ser
    210                 215                 220
Arg Phe Gly Lys Lys Val Thr Tyr Val Val Ile Gly Asp Gly Arg Asp
225                 230                 235                 240
Glu Glu Ile Ala Ala Lys Gln His Asn Met Pro Phe Trp Arg Ile Thr
                245                 250                 255
Asn His Gly Asp Leu Val Ser Leu His Gln Ala Leu Glu Leu Asp Phe
            260                 265                 270
Leu

<210> SEQ ID NO 4
<211> LENGTH: 273
<212> TYPE: PRT
<213> ORGANISM: Homo sapiens

<400> SEQUENCE: 4
```

```
Asp Leu Glu Arg Val Phe Val Trp Asp Leu Asp Glu Thr Ile Ile Val
  1               5                  10                  15

Phe His Ser Leu Leu Thr Gly Ser Tyr Ala Gln Lys Tyr Gly Lys Asp
             20                  25                  30

Pro Pro Met Ala Val Thr Leu Gly Leu Arg Met Glu Glu Met Ile Phe
         35                  40                  45

Asn Leu Ala Asp Thr His Leu Phe Phe Asn Asp Leu Glu Glu Cys Asp
 50                  55                  60

Gln Val His Ile Asp Asp Val Ser Ser Asp Asn Gly Gln Asp Leu
 65                  70                  75                  80

Ser Thr Tyr Ser Phe Ala Thr Asp Gly Phe His Ala Ala Ala Ser Ser
                 85                  90                  95

Ala Asn Leu Cys Leu Pro Thr Gly Val Arg Gly Gly Val Asp Trp Met
                100                 105                 110

Arg Lys Leu Ala Phe Arg Tyr Arg Arg Val Lys Glu Leu Tyr Asn Thr
            115                 120                 125

Tyr Lys Asn Asn Val Gly Gly Leu Leu Gly Pro Ala Lys Arg Asp Ala
        130                 135                 140

Trp Leu Gln Leu Arg Ala Glu Ile Glu Gly Leu Thr Asp Ser Trp Leu
145                 150                 155                 160

Thr Asn Ala Leu Lys Ser Leu Ser Ile Ile Ser Thr Arg Ser Asn Cys
                165                 170                 175

Ile Asn Val Leu Val Thr Thr Thr Gln Leu Ile Pro Ala Leu Ala Lys
                180                 185                 190

Val Leu Leu Tyr Ser Leu Gly Gly Ala Phe Pro Ile Glu Asn Ile Tyr
            195                 200                 205

Ser Ala Thr Lys Ile Gly Lys Glu Ser Cys Phe Glu Arg Ile Met Gln
        210                 215                 220

Arg Phe Gly Arg Lys Val Val Tyr Val Val Ile Gly Asp Gly Val Glu
225                 230                 235                 240

Glu Glu Gln Ala Ala Lys Lys His Asn Met Pro Phe Trp Arg Ile Ser
                245                 250                 255

Ser His Ser Asp Leu Leu Ala Leu His Gln Ala Leu Glu Leu Glu Tyr
                260                 265                 270

Leu
```

<210> SEQ ID NO 5
<211> LENGTH: 10
<212> TYPE: PRT
<213> ORGANISM: Artificial Sequence
<220> FEATURE:
<223> OTHER INFORMATION: Artificially synthesized peptide
<220> FEATURE:
<221> NAME/KEY: VARIANT
<222> LOCATION: 10
<223> OTHER INFORMATION: Xaa = O-Phosphotyrosine

<400> SEQUENCE: 5

```
Lys Lys Ala Thr Gln Ala Ser Gln Glu Xaa
 1               5                  10
```